United States Patent
Mach et al.

(10) Patent No.: US 8,329,686 B2
(45) Date of Patent: Dec. 11, 2012

(54) ISATIN ANALOGUES AND USES THEREFOR

(75) Inventors: Robert H. Mach, Eureka, MO (US);
Michael Welch, St. Louis, MO (US);
Wenhua Chu, St. Louis, MO (US);
Justin Rothfuss, St. Louis, MO (US)

(73) Assignee: Washington University, St. Louis, MO (US)

( * ) Notice: Subject to any disclaimer, the term of this patent is extended or adjusted under 35 U.S.C. 154(b) by 685 days.

(21) Appl. No.: 11/847,330

(22) Filed: Aug. 29, 2007

(65) Prior Publication Data
US 2009/0068105 A1 Mar. 12, 2009

Related U.S. Application Data

(60) Provisional application No. 60/840,747, filed on Aug. 29, 2006, provisional application No. 60/825,635, filed on Sep. 14, 2006.

(51) Int. Cl.
*A61K 31/4439* (2006.01)
*A61K 31/404* (2006.01)
*C07D 401/14* (2006.01)
*C07D 403/12* (2006.01)

(52) U.S. Cl. .................. 514/210.21; 514/414; 514/337; 546/277.7; 548/467; 548/486

(58) Field of Classification Search ................. 548/484, 548/485, 486, 454, 467; 514/210.21, 414, 514/337; 546/277.7
See application file for complete search history.

(56) References Cited

U.S. PATENT DOCUMENTS

| | | | | |
|---|---|---|---|---|
| 4,186,132 A | * | 1/1980 | Gassman et al. | 548/485 |
| 5,840,719 A | * | 11/1998 | Rubin et al. | 514/180 |
| 7,071,332 B2 | * | 7/2006 | Tang et al. | 544/144 |
| 2009/0041664 A1 | * | 2/2009 | Kopka et al. | 424/1.89 |

OTHER PUBLICATIONS

Yoon et al. Nuclear Medicine and Biology 2003, 30, 521-527.*
Lee et al. J. Med. Chem. 2001, 44, 2015-2026.*
Jones et al. Tetrahedron, 1966, 22, 3021-3026.*
Kopka et al. J. Med. Chem. 2006, 49, 6704-6715.*
Chu et al. J. Med. Chem. 2005, 48, 7637-7647.*
Zhou et al. Biorg. Med. Chem. Let. 2006, 16, 5041-5046.*
Registry entry for CAS Registry No. 607699-84-3, which entered STN on Oct. 22, 2003.*
Merriam-Webster online definition for "analogue", obtained from http://www.merriam-webster.com/dictionary/analogue on Jun. 14, 2012.*
Chapman et al, A novel nonpeptidic caspase 3/7 inhibitor (S)-(+)-5-[1-(2-methoxymethylpyrrolidinyl)sulfonyl]-isatin reduces myocardial ischemic injury, Eur J Pharmacol, 2002, 456:59-68.
Choong et al, Identification of potent and selective small-molecule inhibitors of caspase-3 through the use of extended tethering and structure-based drug design, J Med Chem, 2002, 45:5005-5022.
Chu et al, N-benzylisatin sulfonamide analogues as potent caspase-3 inhibitors: synthesis, in vitro activity and molecular modeling studies, J Med Chem, 2005, 48:7637-7647.
Denault and Salvesen, Caspases: Keys in the ignition of cell death, Chem Rev, 2002, 102:4489-4500.
Ekici et al, Aza-peptide Michael acceptors: a new class of inhibitors specific for caspases and other clan CD cysteine proteases, J Med Chem, 2004, 47:1889-1892.
Wagner et al, Synthesis of (R)- and (S)-(S)-[O-methyl-11C]N-[2[3-(2-cyano-phenoxy)-2-hydroxy-propylamino]-ethyl]N0-(4-methoxy-phenyl)-urea as candidate high affinity b1-adrenoceptor PET radioligands, J Labelled Comp Radiopharm, 2005, 48:721-733.
Lahorte et al, Apoptosis-detecting radioligands: current state of the art and future perspectives, Eur J Nucl Med Mol Imaging, 2004, 31:887-919.
Lee et al, Potent and selective nonpeptide inhibitors of caspases 3 and 7 inhibit apoptosis and maintain cell functionality, J Biol Chem, 2000, 275:16007-16014.
Lee et al, Potent and selective nonpeptide inhibitors of caspases 3 and 7, J Med Chem, 2001, 44:2015-2026.
O'Brien and Lee, Prospects for caspase inhibitors, Mini Rev Med Chem, 2004, 4:153-165.
Reed, Apoptosis-based therapies, Nat Rev Drug Discov, 2002, 1:111-121.
Sullivan et al, Alpha-fluoro and alpha-hydroxypyridylalanines, J Med Chem, 1971, 14:211-214.
Yagle et al, Evaluation of 18F annexin V as a PET imaging agent in an animal model of apoptosis, J Nucl Med, 2005, 46:658-66.
Yoo et al, Synthesis of an estrogen receptor beta-selective radioligand: 5-18F]fluoro-(2R,3S)-2,3-bis(4-hydroxyphenyl)pentanenitrile and comparison of in vivo distribution with 16alpha-[18F]fluoro-17beta-estradiol, J Med Chem, 2005, 48:6366-6378.

* cited by examiner

*Primary Examiner* — Rebecca Anderson
*Assistant Examiner* — Matthew Coughlin
(74) *Attorney, Agent, or Firm* — Zackson Law LLC; Saul L Zackson

(57) ABSTRACT

Novel isatin analogues, including isatin analogues comprising Michael Acceptors (IMAs) are disclosed. Further disclosed are methods of synthesis of the isatin analogues, and uses of the analogues, including inhibition of caspase-3 and caspase-7, and in vivo imaging of apoptosis by Positron emission tomography (PET) or Single Photon Emission Computed Tomography (SPECT).

7 Claims, 26 Drawing Sheets

1
IC$_{50}$: 44 nM

2
IC$_{50}$: 2.8 nM

3
IC$_{50}$: 2,800 nM

4
IC$_{50}$: 170 nM previously published

Scheme 1[a]

[a] Reagents: (a) POCl₃; (b) p-toluenesulfonyl chloride, pyridine; (c) phenol, NaH, THF; (d) (1) TFA, CH₂Cl₂, (2) 6, triethylamine; (e) NaH, DMF, R-CH₂X (X = Cl, Br, I).

WC-II-89        WC-II-100

WC-II-101        WC-II-126

WC-II-127

MicroPET IMAGING STUDY: [18F]WC—II-89

FOCUS 120 SCANNER

CONTROL

FOCUS 220 SCANNER

CYCLOHEXIMIDE

SPRAGUE DAWLEY RATS
SUMMED IMAGE

Reagents: (a) NaH, THF (b) BrCH$_2$CH$_2$F (c) LiAlH$_4$, Ethyl Ether (d) CBr$_4$, Ph$_3$P, CH$_2$Cl$_2$ (e) NBS, CCl$_4$ (f) TFA, CH$_2$Cl$_2$ (g) 5-Sulfonylisatin Chloride, Et$_3$N (h) NaH, DMF (i) 4 or 6 (j) AgOMs, Acetonitrile (k) [$^{18}$F]KF, Kryptofix[2,2,2]

Reagents: (a) TFA, CH$_2$Cl$_2$, (b) 5-sulfonylisatin chloride, Et$_3$N, (c) NaH, DMF, (d) R-C$_6$H$_4$-CH$_2$Br, (e) malononitrile, MeOH.

ISATIN ANALOGUES AND USES THEREFOR

RELATED APPLICATIONS

The present application claims priority to U.S. Provisional Patent Application 60/840,747 filed Aug. 29, 2006, and U.S. Provisional Patent Application 60/825,635 filed Sep. 14, 2006. These applications are incorporated herein in their entireties.

REFERENCE TO GOVERNMENT SUPPORT

The invention was developed at least in part with the support of NIH grants HL13851, EB1729 and CA121952. The government may have certain rights in the invention.

BACKGROUND

Apoptosis, or programmed cell death, is a conserved process that is mediated by the activation of a series of cysteine aspartyl-specific proteases termed caspases. Apoptosis plays an important role in a wide variety of normal cellular processes including fetal development, tissue homeostasis, and maintenance of the immune system (1). However, abnormal apoptosis can be involved with diseases such as ischemia-reperfusion injury (stroke and myocardial infarction), cardiomyopathy, neurodegeneration (Alzheimer's Disease, Parkinson's Disease, Huntington's Disease, ALS), sepsis, Type I diabetes, fulminant liver disease, and allograft rejection (2,3). The beneficial effect of many drugs, especially antitumor drugs, can be attributed to their activation of the apoptotic process (26-31).

There are two different classes of caspases involved in apoptosis, the initiator caspases and the executioner caspases (5). The initiator caspases, which include caspase-6, -8, -9, and -10, are located at the top of the signaling cascade; their primary function is to activate the executioner caspases, caspase-2, -3, and -7. The executioner caspases are responsible for the physiological (e.g., cleavage of the DNA repair enzyme PARP-1, nuclear laminins, and cytoskeleton proteins) and morphological changes (DNA strand breaks, nuclear membrane damage, membrane blebbing) that occur in apoptosis (2). A third class of caspases, caspases-1, -4, -5, and -13, are involved in cytokine maturation and are not believed to play an active role in apoptosis.

Consequently, drugs targeting caspase-3 and caspase-7 have been important areas of pharmaceutical research. Most inhibitors of caspase-3 and caspase-7 are small peptides that inhibit caspase-3/7 by interacting either reversibly or irreversibly with cysteine-163 in the active site of the enzyme (6-13). However, peptide-based inhibitors typically have low bioavailability and are not effective in preventing apoptosis in vivo.

Ekici et al. described aza-peptide Michael Acceptors as inhibitors for cysteine proteases, including aza-Asp derivatives that were specific for caspases (40). A potential problems of peptide-based caspase inhibitors is their poor metabolic stability and poor cell penetration (12).

It was previously reported that isatin sulfonamides are potent and selective non-peptide-based inhibitors of the executioner caspases, caspase-3 and -7 (16). One compound, (S)-(+)-5-[1-(2-methoxymethyl-pyrrolidine)sulfonyl]isatin, 1 (FIG. 1) has been shown to reduce tissue damage in an isolated rabbit heart model of ischemic injury (14,15). Additional structure-activity relationship studies have revealed that replacement of the 2-methoxymethyl group with a phenoxymethyl moiety and the introduction of an alkyl group on the isatin nitrogen group results in improved potency for inhibiting caspase-3 activity (2) (FIG. 1) (16). An additional improvement in potency was also reported when the pyrrolidine ring of 3 (FIG. 1) was replaced with an azetidine ring to give compound 4 (FIG. 1) (16).

Positron emission tomography (PET) and Single Photon Emission Computed Tomography (SPECT) are in vivo imaging techniques that measure changes in tissue and cellular function at the molecular level. Most agents used for imaging apoptosis in vivo are based on detection of Annexin V (32) and propidium iodide exclusion test (33), is required to discriminate between apoptosis and necrosis in vitro. Although such tests are routinely used to distinguish apoptosis from necrosis using ex vivo techniques such as flow cytometry, they cannot be applied to in vivo techniques such as PET and SPECT due to the short half-life radionuclides used.

A previous study reported the synthesis and carbon-11 radiolabeling of an isatin analog having a modest potency for inhibiting caspase-3 (38). However, no in vivo data were reported in this meeting abstract, and the selectivity of this compound for caspase-3 versus other caspases was not mentioned.

A potential disadvantage of known isatin analogues described as caspase inhibitors is that they are reversible inhibitors of caspase-3/7 since they form a thio-hemiketal with Cys-163 in the active site of activated caspase-3/7 (FIG. 14). Because current isatin analogues are predicted to be reversible inhibitors of activated caspase-3/7, they provide only temporary inactivation of the enzyme.

SUMMARY

The present inventors have developed a series of isatin analogue compounds, and methods for imaging apoptosis in humans and animals using radiolabeled isatin analogues as probes for apoptotic cells. In some aspects, these methods can discriminate apoptosis from necrosis. In various aspects, the methods comprise imaging caspase-3 activity, which can serve as a marker for apoptotic cell death. The methods utilize imaging techniques such as positron emission tomography (PET) and single photon emission computed tomography (SPECT), in conjunction with radiolabeled isatin analogues as ligands for caspase-3. The present inventors further report the validation of both the compounds and the methods in an animal model of apoptosis. The lead compound for the current study was the isatin analog, 2 (FIG. 2), which was first reported by Lee et al. (16). Accordingly, the inventors describe herein the synthesis of a new isatin sulfonamide analogue, WC-II-89, that is suitable for radiolabeling with fluorine-18, and the biodistribution of [$^{18}$F]WC-II-89 in an animal model of apoptosis. The inventors furthermore report the first microPET imaging study directly measuring caspase-3 activation in tissues undergoing apoptosis using [$^{18}$F]WC-II-89.

In various aspects, the present inventors disclose: the synthesis and in vitro binding of a series of isatin analogues that can be radiolabeled with a positron-emitting nuclide such as fluorine-18 or bromine-76 for PET imaging studies; a novel method for preparing the labeled isatin analogs for PET imaging studies; and imaging of caspase-3 activation using the radiolabeled isatin analogs, demonstrated herein using in an animal model of apoptosis. The inventors show that WC-II-89 binds to caspase-3 and caspase-7 with high affinity and specificity versus caspase-1, -6, and -8. Biodistribution studies of [$^{18}$F]WC-II-89 reveal a higher uptake in the liver and spleen of rats treated with cycloheximide, a well-established murine model of chemically induced apoptosis. Western blot analysis confirms this uptake can be related to caspase-3 activation. The results demonstrate for the first time that apoptosis can be measured and imaged by PET using [$^{18}$]F-labeled caspase-3 inhibitors such as [$^{18}$F]WC-II-89.

In various aspects, some isatin analogs which can be used for PET imaging caspase-3 activation (e.g., in apoptosis) such as the compounds illustrated in FIG. 8. These compounds can function as inhibitors of caspase activity. In some aspects, the inventors disclose processes for preparing the corresponding fluorinated versions, including $^{18}$F-labeled versions of the isatin analogues. In particular, labeling of WC-II-89, WC-II-100, and WC-II-101 can be effected using the specific base catalyzed conditions outlined in the scheme depicted in FIG. 4. In the synthesis scheme, the function of the specific base (i.e., hydroxide ion) is to convert the ketone of the isatin precursor to the corresponding ketone hydrate, which promotes conversion to the radiolabeled compound.

In some aspects of the present teachings, a compound disclosed herein, such as [$^{18}$F]WC-II-89, can serve as a probe for imaging activated caspase-3 in tissues undergoing apoptosis.

In some aspects of the present teachings, the inventors disclose methods of preparation of isatin sulfonamide analogues. In other aspects, the inventors demonstrate inhibition properties of compounds of the present teachings towards various caspases, such as caspase-1, -3, -6, -7, and -8. In some aspects, compounds displaying nanomolar potency for inhibiting the executioner caspases, caspase-3 and caspase-7, are disclosed. These compounds were also observed to have a low potency for inhibiting the initiator caspases, caspase-1 and caspase-8, and caspase-6. In some aspects, molecular modeling studies provided further insight into the interaction of this class of compounds with activated caspase-3. The results of the current study revealed a number of non-peptide-based caspase inhibitors which can be used in assessing the role of inhibiting the executioner caspases in minimizing tissue damage in disease conditions which include apoptosis.

Compounds described herein have the potential to block cellular death in pathological conditions characterized by an increase in apoptosis. The importance of the methylenemalononitrile group is evident in the low potency of the corresponding mono-cyano analogue, WC(II)-99, and the oxime analogues WC(II)-51 and WC(II)-52 (FIG. 17; Table 2).

In other aspects, the present inventors disclose isatin analogue inhibitors of caspase-3/7 in which the keto carbonyl of the isatin ring is replaced with a Michael acceptor such as the methylenemalononitrile group. Without being limited by theory, these compounds are expected to be irreversible inhibitors of caspase-3/7, as this substitution is expected to result in the thioalkylation of Cys-163 in the active site of caspase-3/7, thereby resulting in the irreversible inactivation of the enzyme (FIG. 15). This class of compounds has been given the name Isatin Michael Acceptors (IMAs). Structures of various IMAs are provided in FIG. 16.

Accordingly, various aspects of the present teachings include: the synthesis and in vitro binding of a series of isatin Michael Acceptors that can irreversibly inhibit caspase-3/7; the synthesis and in vitro binding of a series of isatin Michael Acceptors that can be radiolabeled with $^{18}$F, $^{11}$C or $^{76}$Br; and methods for preparing the $^{18}$F-labeled analogues. In various configurations, these radiolabeled compounds can be used for PET imaging of caspase 3/7 activity, e.g., in apoptosis, and are therefore useful in clinical applications such as monitoring progress of cancer chemotherapy.

In various aspects of the present teachings, the inventors have investigated novel Michael Acceptor Isatin analogues. The inventors describe synthetic methods, and present results of in vitro studies of a series of Michael Acceptor isatin analogues having a high potency for inhibiting the executioner caspases, caspase-3, and caspase-7. The results extend the structure-activity relationships of this class of compounds and provide further insight into the development of non-peptide-based inhibitors of caspase-3 and caspase-7. The Michael Acceptor compounds described herein are useful probes for determining the effectiveness of inhibiting caspase-3 and caspase-7, and for minimizing tissue damage in pathological conditions characterized by unregulated apoptosis. In various aspects, the Isatin Michael Acceptors are as potent for inhibiting caspase-3/7 activity as the parent isatin analogues.

In some aspects of the present teachings, the corresponding radiolabeled versions of the IMAs can be used to image apoptosis using the functional imaging techniques, Positron Emission Tomography (PET and Single Photon Emission Computed Tomography (SPECT). An example of the synthesis of a $^{18}$F-labeled IMA is shown in FIG. 18 and consists on the simple conversion of the isatin to the corresponding IMA via condensation with dicyanomethane. The IMA-based radiotracers disclosed herein are capable of producing similar if not better imaging results compared to their non-Michael acceptor isatin-based counterparts. Furthermore, the Log P value of the IMA analogs are lower than the corresponding values of non-Michael acceptor isatin analogs (e.g., 25d vs. 27d, Log P 4.82 vs. 4.28; 28b vs. 30b, 2.25 vs. 1.77; and 28c vs. 30c, 3.76 vs. 3.22, respectively (FIG. 19, table 7)). This lower Log P value of the IMA caspase-3 inhibitor increases the drug's ability to penetrate the cell in vivo and label the target.

TABLE 2

In vitro assays of Michael Acceptor isatin analogues for inhibiting caspase activity. Data present IC$_{50}$ (nM) for each compound as tested against each caspase.

| # | Caspase 1 | Caspase 3 | Caspase 6 | Caspase 7 | Caspase 8 |
|---|---|---|---|---|---|
| WC-II-53 | 1,830 ± 127 | 272 ± 25 | 407 ± 15 | 1,585 ± 163 | >50,000 |
| WC-II-54 | 2,377 ± 716 | 283 ± 15 | 540 ± 44 | 2,385 ± 799 | >50,000 |
| WC-II-62 | 2,825 ± 248 | 119 ± 4 | 698 ± 94 | 785 ± 276 | >50,000 |
| WC-II-69 | 3,900 ± 530 | 7.8 ± 1.5 | 610 ± 113 | 29.6 ± 1.4 | >50,000 |
| WC-II-87 | 3,600 ± 640 | 6.0 ± 0.8 | 450 ± 43 | 50.0 ± 11.6 | >50,000 |
| WC-II-92 | 10,000 ± 1600 | 18.3 ± 0.4 | 927 ± 35 | 96.3 ± 20.7 | >50,000 |
| WC-II-103 | 3,500 ± 960 | 7.5 ± 0.2 | 770 ± 119 | 26.0 ± 5.2 | >50,000 |
| WC-II-104 | 2,900 ± 900 | 7.1 ± 0.6 | 580 ± 55 | 22.7 ± 3.1 | >50,000 |
| WC-II-128 | 3,400 ± 100 | 5.13 ± 0.70 | 515 ± 77 | 26.3 ± 0.8 | >50,000 |
| WC-II-129 | 5,700 ± 850 | 20.1 ± 1.3 | 840 ± 125 | 92.2 ± 11.8 | >50,000 |
| WC-II-142 | 2,300 ± 250 | 31.8 ± 6.2 | 744 ± 48 | 126 ± 19 | >50,000 |
| WC-III-49 | 6,220 ± 1250 | 27.8 ± 2.5 | 918 ± 151 | 51.7 ± 6.2 | >50,000 |
| WC-III-50 | 3,250 ± 450 | 7.6 ± 1.1 | 823 ± 86 | 32.8 ± 4.9 | >50,000 |
| WC-III-51 | 2,720 ± 580 | 7.8 ± 1.9 | 850 ± 21 | 28.3 ± 5.4 | >50,000 |
| WC-II-52 | >50,000 | >20,000 | >20,000 | >50,000 | >50,000 |
| WC-II-99 | — | >1,000 | — | — | — |
| Ac-YVAD-CHO | 8.1 ± 2.1 | | | | |
| Ac-DEVD-CHO | | 3.8 ± 0.8 | | 8.0 ± 1.0 | |

TABLE 2-continued

In vitro assays of Michael Acceptor isatin analogues for inhibiting caspase activity.
Data present IC$_{50}$ (nM) for each compound as tested against each caspase.

| # | Caspase 1 | Caspase 3 | Caspase 6 | Caspase 7 | Caspase 8 |
|---|---|---|---|---|---|
| Ac-VEID-CHO | | | 9.6 ± 2.1 | | |
| Ac-IETD-CHO | | | | | 4.0 ± 0.1 |

Data present IC$_{50}$ (nM) for each compound as tested against each caspase.

DETAILED DESCRIPTION

The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999, and textbooks such as Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004.

Chemistry. In some aspects of the present teachings, the inventors disclose preparation of isatin sulfonamide analogues and demonstrating their potencies for inhibiting caspase-1, -3, -6, -7, and -8. Several compounds displaying nanomolar potency for inhibiting the executioner caspases, caspase-3 and caspase-7 in vitro were identified. These compounds were also observed to have a low potency for inhibiting the initiator caspases, caspase-1 and caspase-8, and caspase-6. In some aspects, molecular modeling studies provided further insight into the interaction of this class of compounds with activated caspase-3. The present teachings therefore include a number of non-peptide-based caspase inhibitors which can be used in assessing the role of inhibiting the executioner caspases in minimizing tissue damage in disease conditions which include apoptosis.

Figure 5:
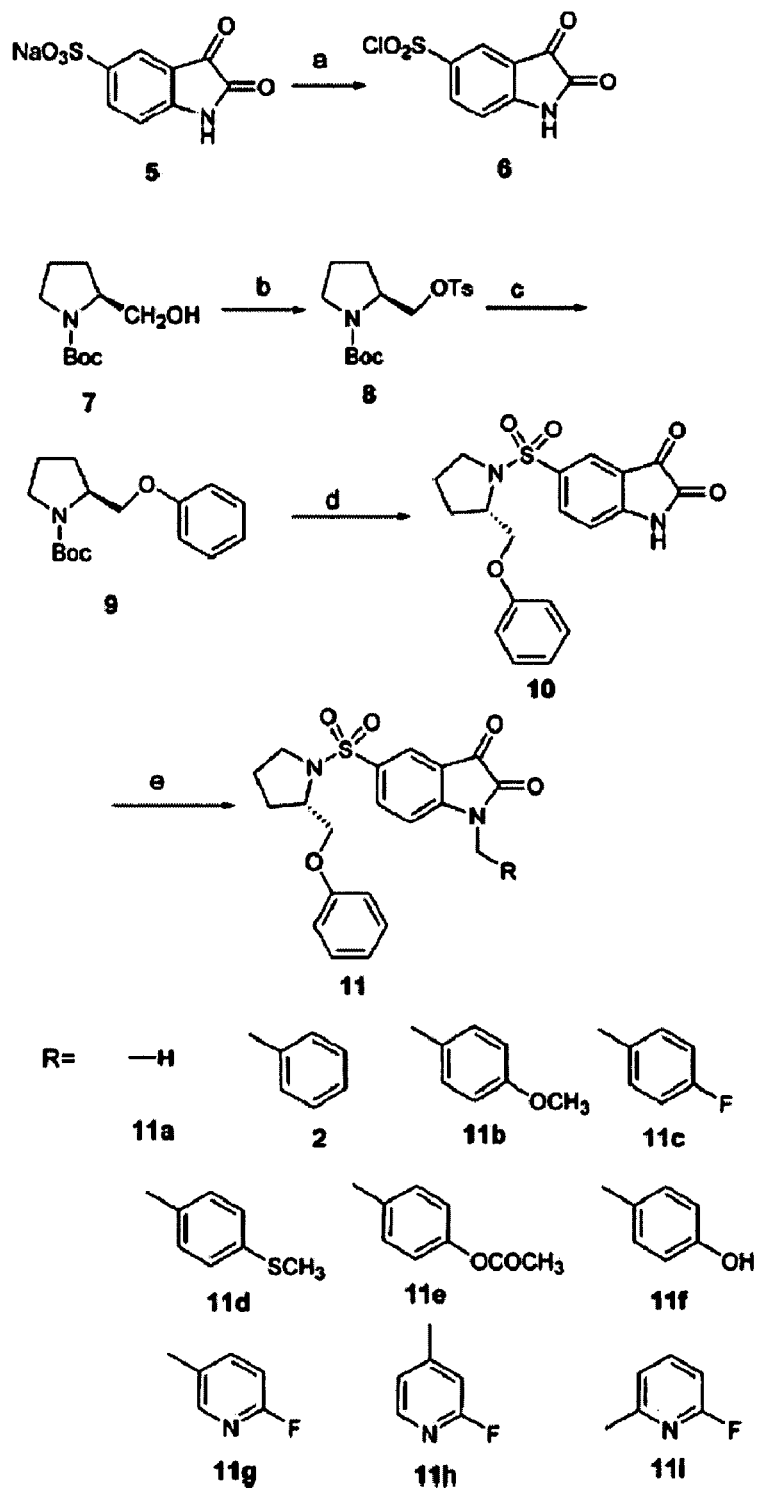
FIG. 5 illustrates scheme 1, for the synthesis of 5-(2-phenoxymethylpyrrolidine-1-sulfonyl)isatin analogues.

The synthesis of 5-(2-phenoxymethylpyrrolidine-1-sulfonyl)isatin analogues is shown in Scheme 1 (FIG. 5). The 5-chlorosulfonylisatin 6 was prepared by reaction of 5-isatinsulfonic acid, sodium salt hydrate (5) with phosphorus oxychloride in tetramethylene sulfone at 60° C. for 3 h. The hydroxyl group of N-Boc-2-pyrrolmethanol (7) was first tosylated with p-toluenesulfonyl chloride in pyridine to give compound 8, followed by displacement of the tosylate group by sodium phenoxide in DMF to afford N-Boc-2-(phenoxymethyl)pyrrolidine 9. The N-Boc group of 9 was removed with TFA, and the secondary amine was coupled with 6 in THF using triethylamine as an acid scavenger to afford the 5-(2-phenoxymethyl-pyrrolidinesulfonyl)-1H-2,3-dione 10 in 84% yield. The isatin nitrogen was alkylated by treatment of 10 with sodium hydride in DMF at 0° C. followed by addition of various alkyl halides to give compounds 2 and 11a-e,g-i. Compound 11f was prepared by hydrolysis of 11e with sodium hydroxide in aqueous methanol.

Figure 19:
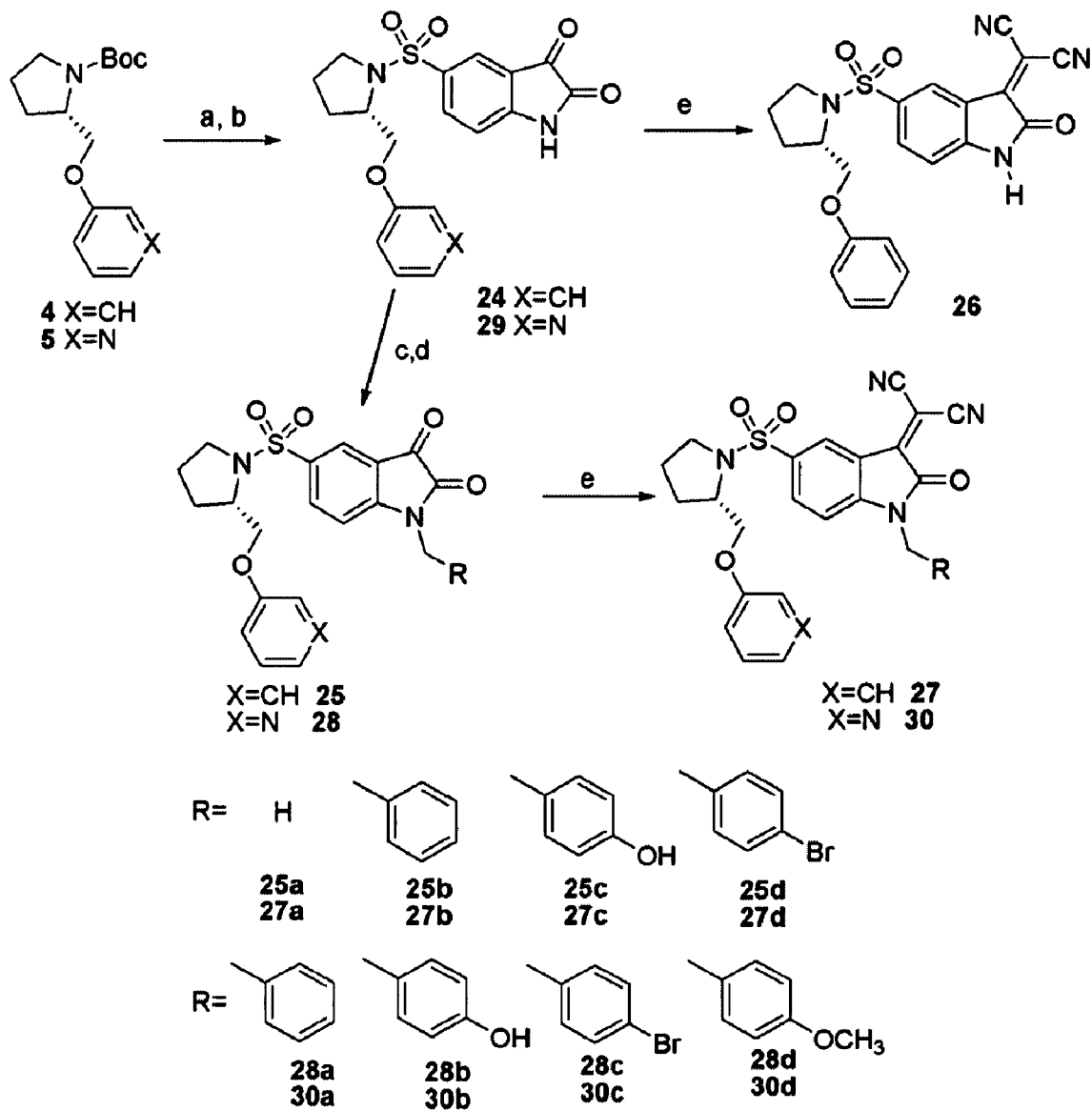
FIG. 19 illustrates Scheme 4 for synthesis of 5-(2-phenoxymethyl-pyrrolidine-1-sulfonyl)isatin and its IMA analogs.

The synthesis of 5-(2-phenoxymethyl-pyrrolidine-1-sulfonyl)isatin and its IMA analogs are shown in FIG. 19. The isatin analogs 24,25a-c$^{21}$ and 25d were reacted with malononitrile in methanol to give the IMA analogs, 26 and 27a-d, respectively. The 5-(2-pyridin-3-yl-oxymethyl)pyrrolidine-1-sulfonyl)isatin analogs 28a, 28c, and 28d, were prepared by using the same sequence of reactions described in the synthesis of 25d (Scheme 1). For the compound 28b, the isatin nitrogen of 29 was first alkylated with (4-bromomethyl-phenoxy)-tert-butyl-diphenyl-silane, then the protecting group tert-butyl-diphenyl-silane was removed with nBu$_4$NF in THF to afford 10b. The IMA analogs of the 5-(2-pyridin-3-yl-oxymethyl)pyrrolidine-1-sulfonyl)isatin, 12a-d, were prepared with the same methods of 11a-d.

The IC$_{50}$ values from the enzyme assays are summarized in Table 1. The results show that the phenoxymethyl and pyridin-3-yl-oxymethyl isatin analogs, 25d, 28b, and 28c, are potent and selective inhibitors for caspase-3/7 relative to caspases-1, -6, -8. The IMA analogs of phenoxymethyl isatin compounds 26 and 27a, where the isatin nitrogen of the indol ring is not alkylated or instead possesses a methyl group, have low potency for caspase-3 and -7 inhibition; these IC$_{50}$ values are 272 nM and 119.3 mM for caspase-3, and 1,585 nM and 785 mM for caspase-7, respectively. When the isatin nitrogen of the indol ring was alkylated with an aromatic group, the potency of IMA analogs 27b, 27c, and 27d, improved drastically for caspase-3/7 with IC$_{50}$ values of 27.8 nM, 31.8 nM, and 20.1 nM for caspase-3, and 51.7 nM, 126.0 nM, and 92.2 nM for caspase-7, respectively, while retaining their high selectivity. Also, all of these compounds have less activity for inhibition of caspase-1 (IC$_{50}$: 2,300-6,200 nM), caspase 6 (IC$_{50}$ 744-926 nM), and caspase-8 (IC$_{50}$>50,000 nM) upon addition of the aromatic group. Similarly, the IMA analogs of pyridin-3-yl-oxymethyl isatin, 30a, 30b, 30c and 30d, are potent and selective inhibitors for caspase-3 (IC$_{50}$: 7.6, 7.8, 5.1, and 7.8 nM) and caspase-7 (IC$_{50}$: 32.8, 28.6, 26.3, and 15.1 nM), and show weak inhibition of caspase-1 (IC$_{50}$: 2,700-3,200 nM), caspase-6 (IC$_{50}$: 515-770 nM), and caspase-8 (IC$_{50}$: >50,000 nM). The IMA analogs of pyridin-3-yl-oxymethyl isatin also display improved potency for inhibiting caspases-3/7 than the corresponding IMA analogs of phenoxymethyl isatin (Table 1, 27b, 27c, 27d, compare with 30a, 30h, 30c, respectively). It is interesting to note that all the IMA analogs have an increased potency of roughly 10-fold for caspase-6 when compared to their complementary isatin analogs (see Table 1).

Figure 8:
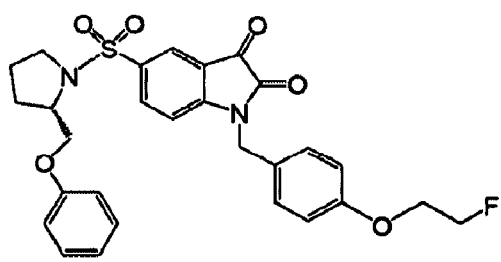
FIG. 8 illustrates some isatin analogs which can be used for PET imaging caspase-3 activation.
Figure 8:
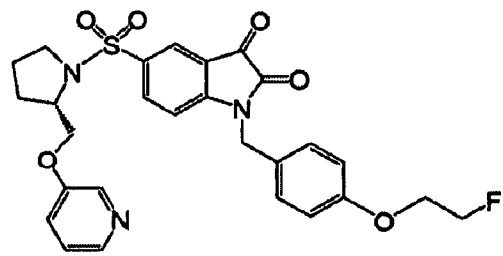
Figure 8:
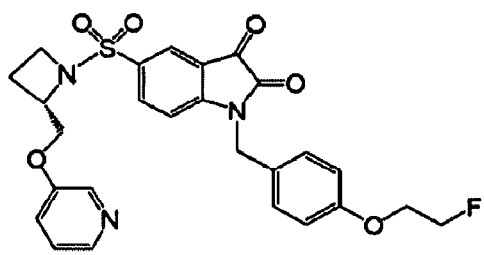
Figure 8:
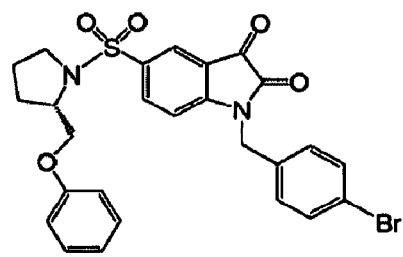
Figure 8:
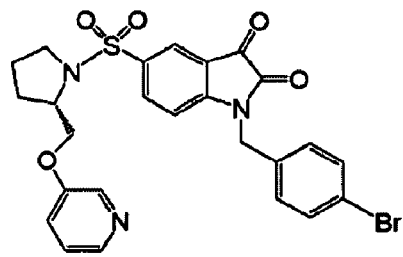

In various aspects, some isatin analogs which can be used for PET imaging caspase-3 activation (e.g., in apoptosis) include the compounds illustrated in FIG. 8. These compounds can function as inhibitors of caspase activity, as shown by the following in vitro assay results (Table 1).

Figure 20:
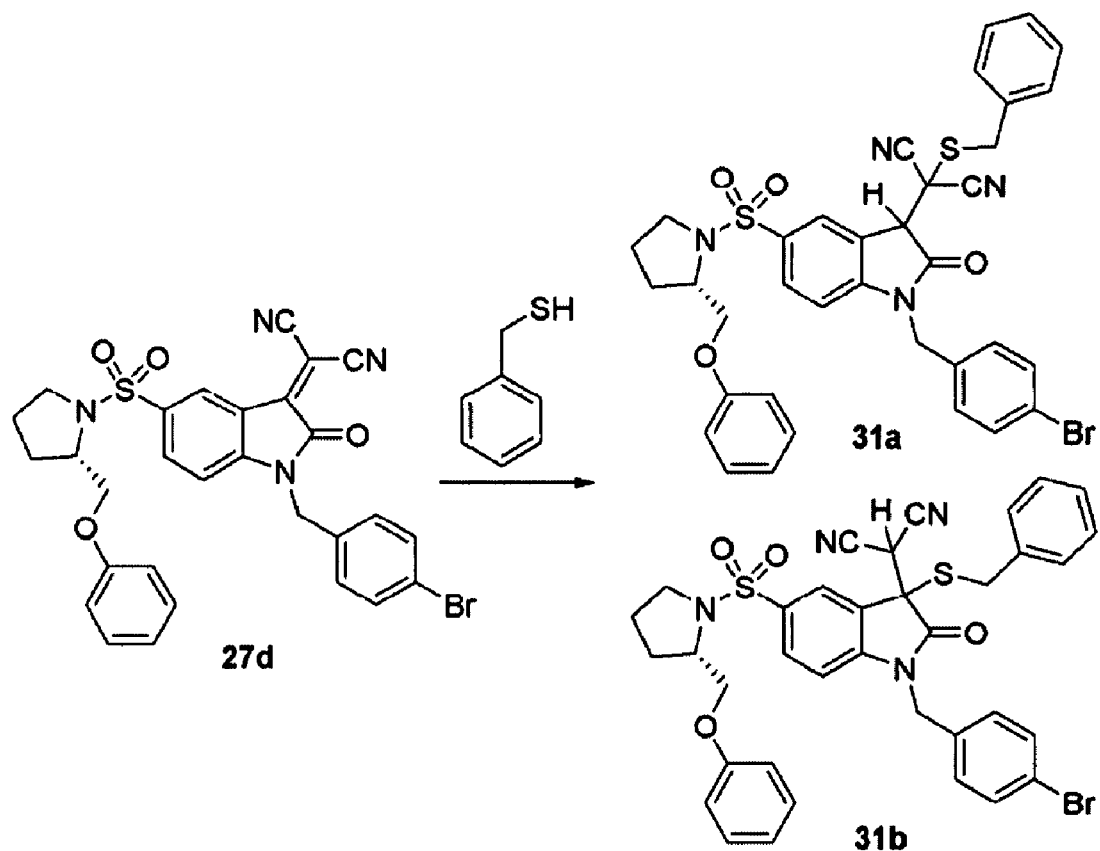
FIG. 20 illustrates Scheme 5 for synthesis of two possible Michael addition products.

In some embodiments, the inhibition mechanism was further investigated by using 27d and its reaction with benzylmercaptan as a model. There are two possible Michael addition products (31a or 31b) produced by attack of the thiol nucleophile of benzylmercaptan to 27d (FIG. 20). The products depend on the position of attack of the thiol group of benzylmercaptan on the carbon-carbon double bond of 27d (Scheme 5). Initially, we hoped to purify the Michael addition product in order to obtain a crystal structure by X-ray diffraction. Therefore, benzylmercaptan was reacted with 27d in CH$_2$Cl$_2$ and a white solid was obtained following evaporation of the CH$_2$Cl$_2$ and excess benzylmercaptan in vacuum. However, when the white solid was recrystallized from ethyl acetate, a purple solid was produced and NMR structural analysis revealed it was the starting material, 27d. This result shows that the Michael addition product is easily reversible and leads to the formation of the starting material. Hence, 27d is a reversible Michael acceptor inhibitor. This result is consistent with our inhibition studies of human caspase-3 with IMA inhibitors. Human caspase-3 activity is inhibited when incubated with caspase-3 and the IMA inhibitor, yet caspase-3 activity can be recovered when the IMA inhibitor is removed by gel filtration and washed with water. In an effort to better understand the chemical structure of the Michael addition product, a series of detailed NMR studies were carried out. The proton and carbon chemical shifts for the Michael addition product were assigned through two dimensional correlation spectroscopy (COSY, HMQC, and HMBC). The results show that the structure of the Michael addition product is 31b instead of 31a, thereby demonstrating that the thiol group of benzylmercaptan prefers to attack the indol ring carbon versus the exocyclic methylene group of 27d.

Figure 6:
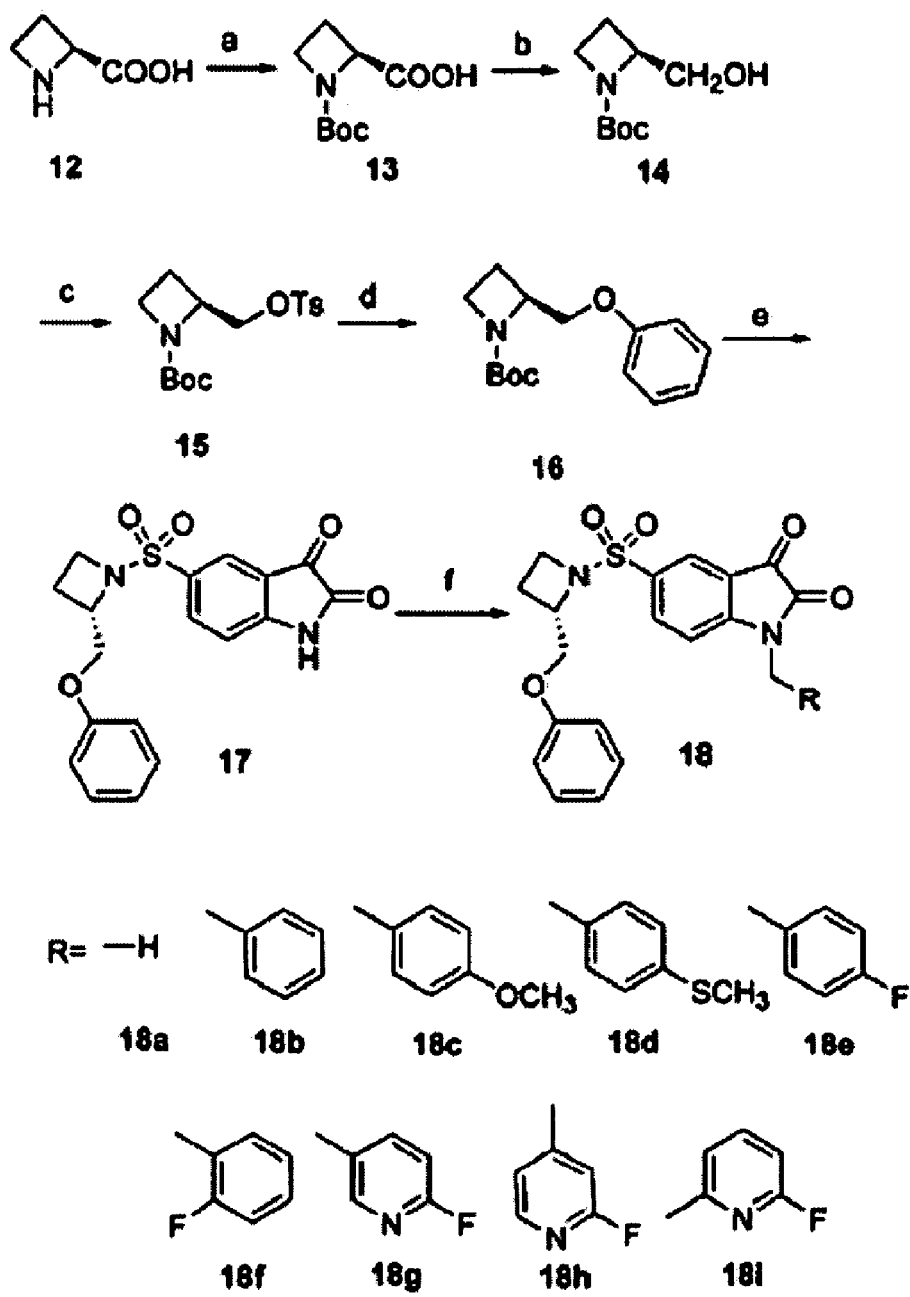
FIG. 6 illustrates scheme 2, for the synthesis of 5-(2-phenoxymethyl-azetidine-1-sulfonyl)isatin analogues.
Figure 7:
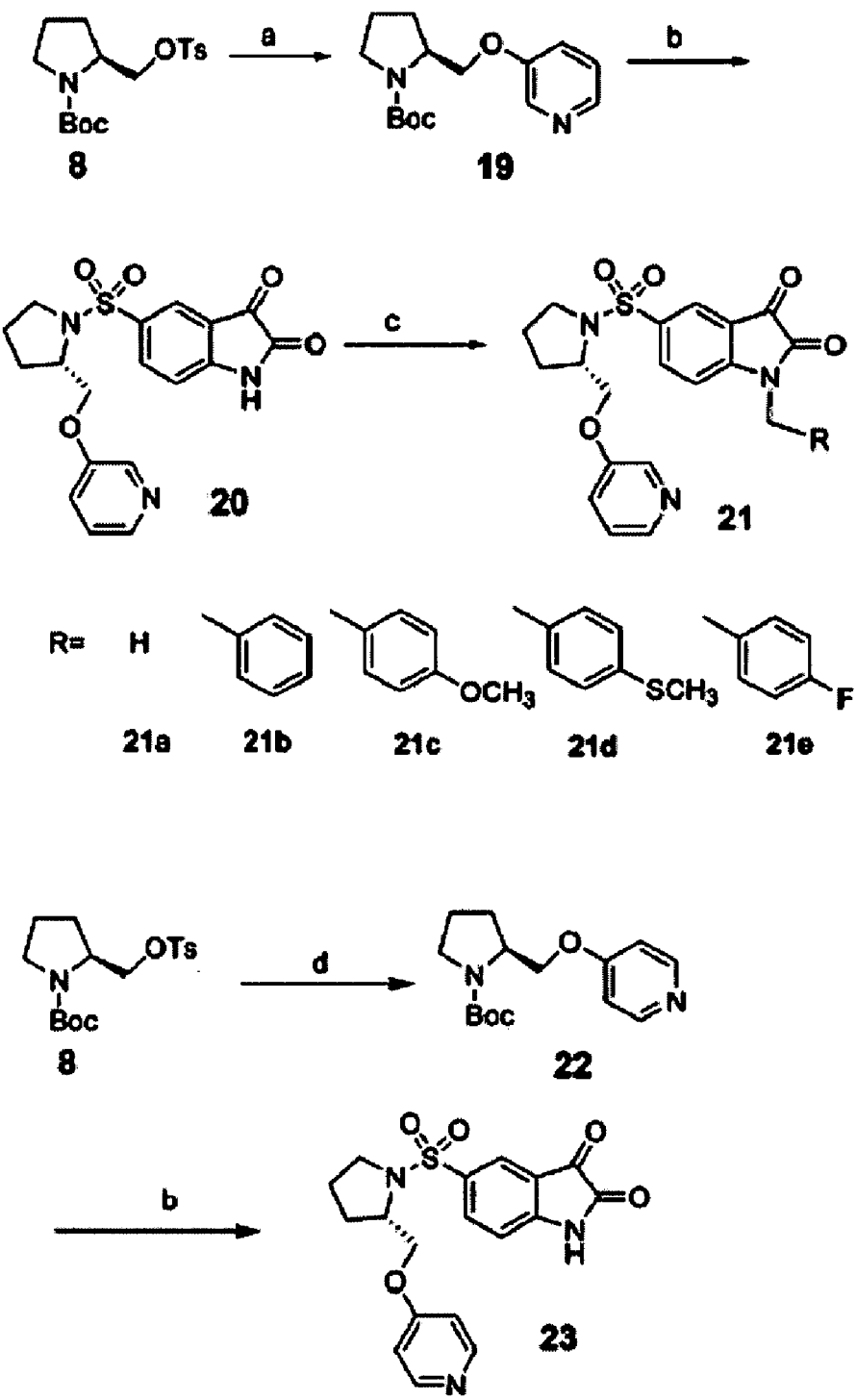
FIG. 7 illustrates scheme 3, for the synthesis of 5-(2-pyridin-3-yl-oxymethyl)pyrrolidine-1-sulfonyl)isatin analogues as well as a 4-pyridyl analogue.

The synthesis of 5-(2-phenoxymethyl-azetidine-1-sulfonyl) isatin analogues is shown in Scheme 2 (FIG. 6). The intermediate (S)—N-Boc-2-azetidinemethanol 14 was prepared from (S)-2-azetidinecarboxylic acid 12 according to the literature method (17). The hydroxy group of 14 was tosylated with p-toluenesulfonyl chloride in pyridine to afford compound 15, which was converted to the corresponding phenoxyl group as described above to give 16. Compound 16 was deprotected with TFA, and the secondary amine was coupled with 6 using triethylamine as the base to afford 1.7 in 63% yield. The nitrogen of 17 was alkylated by the same procedure as that of 10 to give compounds 18a-i. Similarly, the 5-(2-pyridin-3-yl-oxymethyl)pyrrolidine-1-sulfonyl) isatin analogues were prepared by using the same sequence of reactions described in the synthesis of 11a-i to afford compounds 21a-e (Scheme 3) (FIG. 7). The synthesis of the 4-pyridyl analogue 23 is also outlined in Scheme 3.

Figure 11:
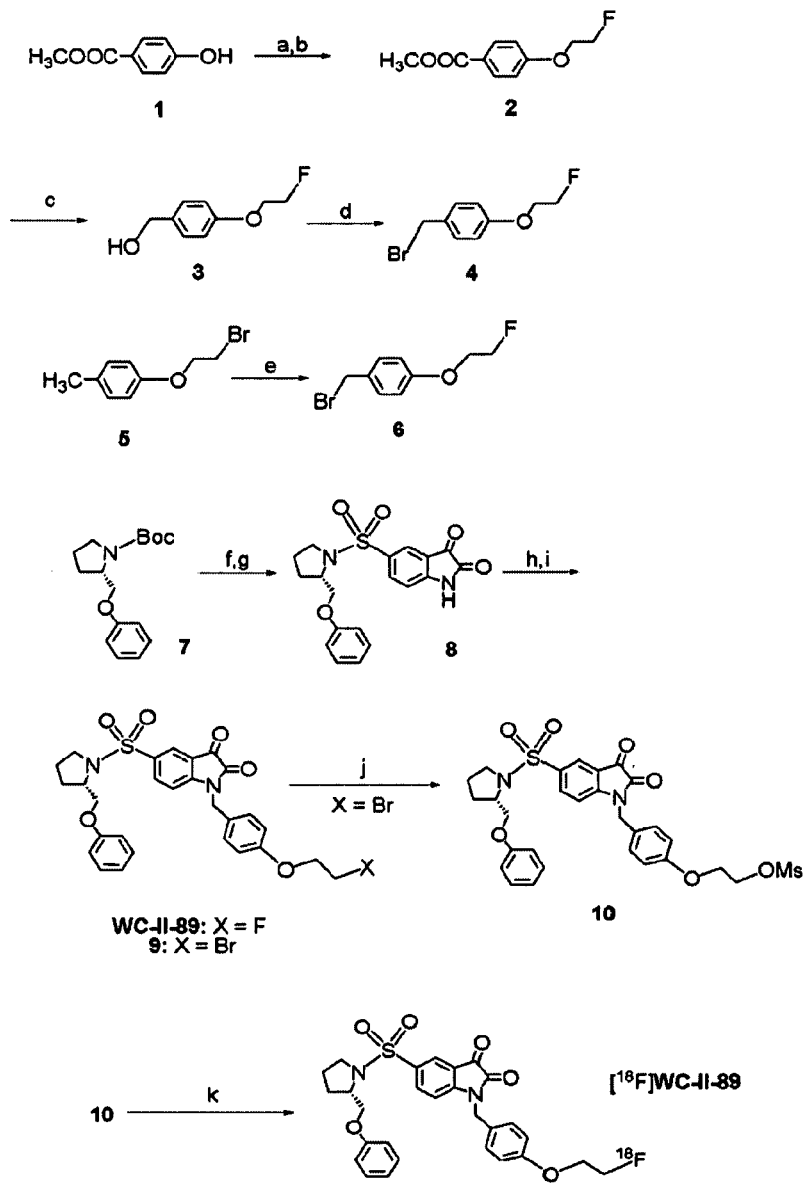
FIG. 11 illustrates a scheme for the synthesis of compound [$^{18}$F]WC-II-89. Compound 10 is converted to [$^{18}$F]WC-II-89 by the steps illustrated in FIG. 7.

The synthesis of WC-II-89 and its precursor for [$^{18}$F]-labeling, 10, is shown in the scheme illustrated in FIG. 8. In FIG. 11, O-alkylation of methyl 4-hydroxybenzoate 1 is achieved

TABLE 1

Inhibitor selectivity of some isatin analogs which can be used for PET imaging.

| compound | IC$_{50}$ (nM) | | | | |
|---|---|---|---|---|---|
| | Caspase 1 | Caspase 3 | Caspase 6 | Caspase 7 | Caspase 8 |
| WC-II-89 | >15,000 | 9.7 ± 1.3 | 3,725 ± 390 | 23.5 ± 3.5 | >50,000 |
| WC-II-100 | >20,000 | 3.1 ± 0.4 | 6,900 ± 850 | 11.3 ± 0.6 | >50,000 |
| WC-II-101 | >10,000 | 3.6 ± 0.5 | 8,700 ± 140 | 17.6 ± 0.4 | >50,000 |
| WC-II-126 | >15,000 | 9.9 ± 0.9 | 8,900 ± 424 | 34.8 ± 1.4 | >50,000 |
| WC-II-127 | >15,000 | 3.6 ± 0.5 | 5.025 ± 318 | 6.6 ± 0.1 | >50,000 |
| Ac-YVAD-CHO | 8.1 ± 2.1 | | | | |
| Ac-DEVD-CHO | | 4.8 ± 2.0 | | 8.5 ± 1.0 | |
| Ac-VEID-CHO | | | 60.5 ± 7.6 | | |
| Ac-IETD-CHO | | | | | 4.7 ± 0.9 |

Figure 9:
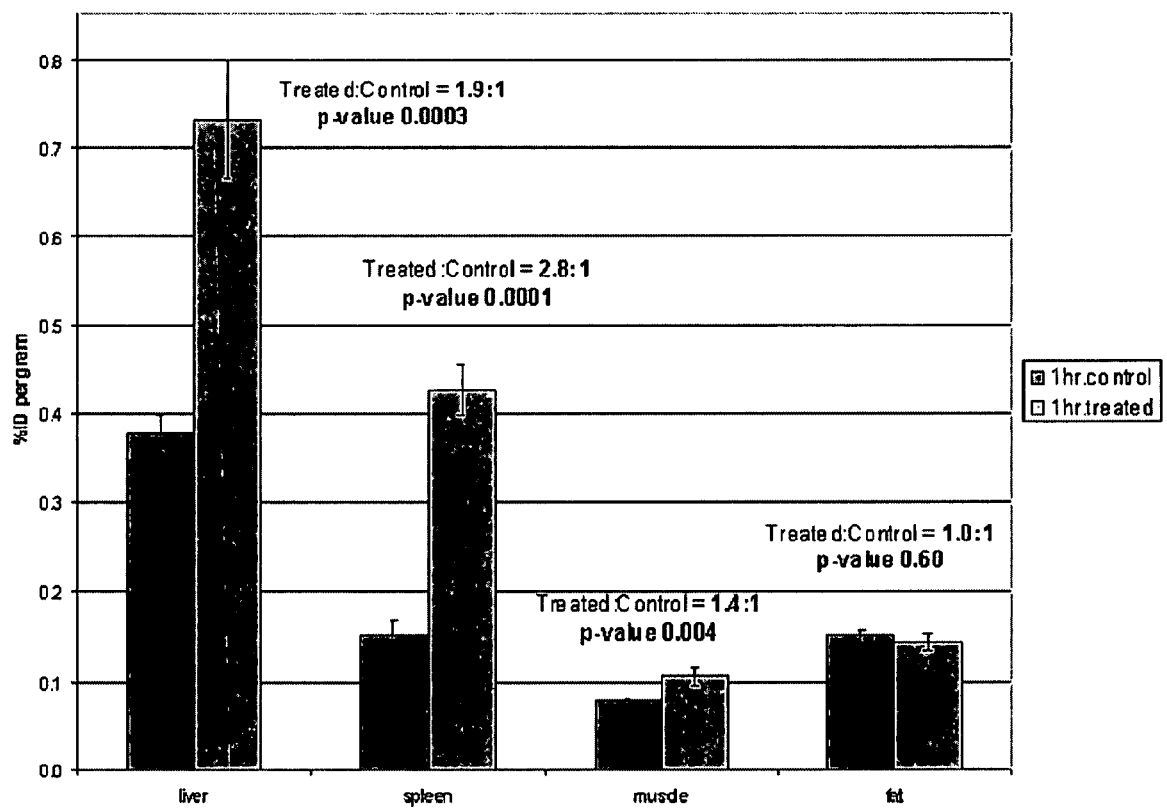
FIG. 9 illustrates selected biodistribution of [$^{18}$F]WC-II-89 in control and cycloheximide (5 mg/kg), 3 hour pre-treated male Sprague-Dawley rats (200-250 g). Note the higher uptake in the cycloheximide-treated animals, in particular the high uptake of the radiotracer in the spleen and liver.
Figure 10:
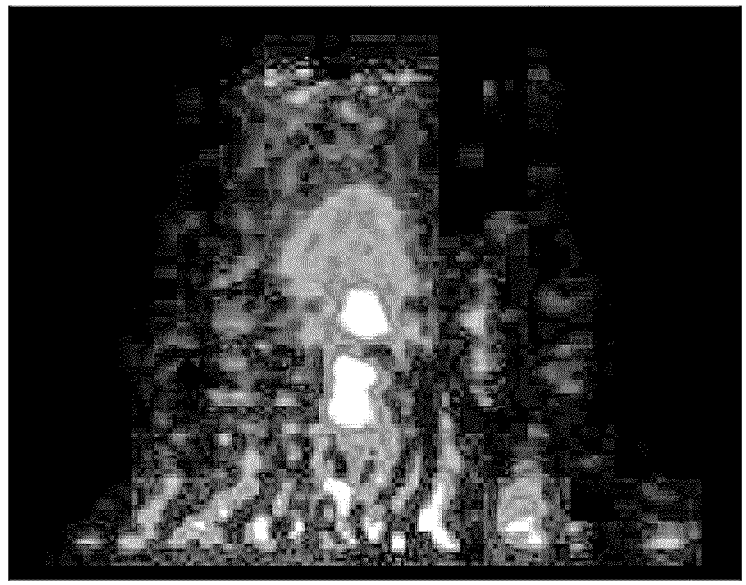
FIG. 10 illustrates microPET images of [$^{18}$F]WC-II-89 distribution in a control rat (left) and cycloheximide-treated rat (right). Images were summed from 10 to 60 minutes after i.v. injection of ~150 µCi of [$^{18}$F]WC-II-89.
Figure 10:
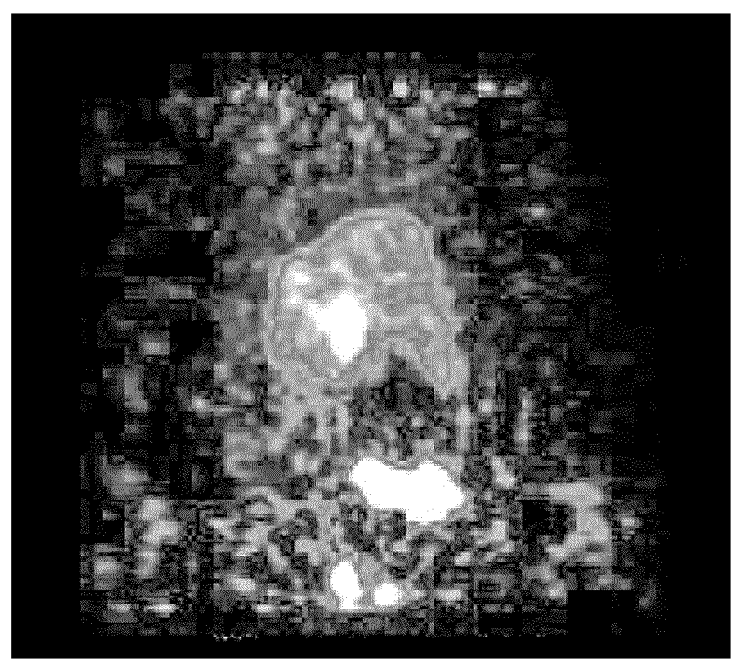

In some aspects of the present teachings, [$^{18}$F]WC-II-89 can serve as a probe for imaging activated caspase-3 in tissues undergoing apoptosis. The animal model used in these studies was cyclohexamide-induced apoptosis in Sprague-Dawley rats. The results are shown in FIG. 9 and FIG. 10.

by conversion to the corresponding sodium salt (sodium hydride in THF at 0° C.) followed by addition of 1-bromo-2-fluoroethane to give compound 2, which is reduced by LiAlH$_4$ in ether to afford the alcohol, 3. The hydroxyl group of 3 is then converted to the corresponding bromo analog 4 via treatment with CBr$_4$ and Ph$_3$P in CH$_2$Cl$_2$. 1-(2-Bromoethoxy)-4-(bromomethyl)benzene 6 is obtained by bromination of 5 with NBS in CCl$_4$. The N-Boc group of 7 is removed with TFA and the secondary amine is coupled with 5-chlorosulfonylisatin in THF using triethylamine as an acid scavenger to produce 5-(2-phenoxymethyl-pyrrolidine-sulfonyl)-1H-2,3-dione, 8. The isatin nitrogen is alkylated by treatment of 8 with sodium hydride in DMF at 0° C. followed by addition of 4 or 6 to give compounds WC-II-89 and 9, respectively. Compound 9 is then heated to reflux with silver methanesulfonate in acetonitrile to generate the precursor 10.

Figure 18:
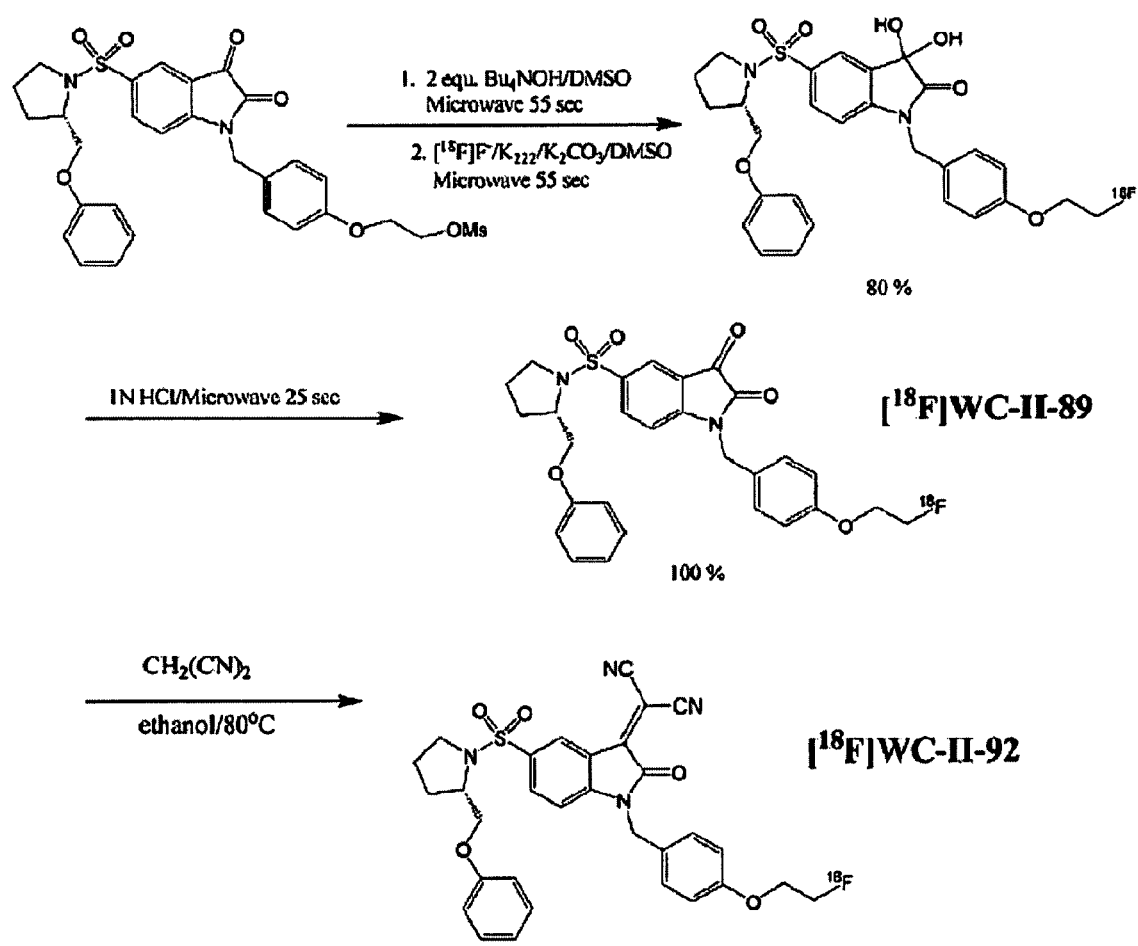
FIG. 18 illustrates synthesis of an $^{18}$F-labeled Isatin Michael Acceptor (MA).

Starting from 10, the [$^{18}$F]WC-II-89 was synthesized by the nucleophilic substitution of the mesylate group with [$^{18}$F] fluoride ion using the radiochemical procedure outlined in the Scheme (34). The incorporation yield was more than 70% and the synthesis time was less than 100 minutes. [$^{18}$F]WC-II-89 was confirmed by the co-elution with nonradioactive standard WC-II-89 on an analytical HPLC system. The radiochemical purity of [$^{18}$F]WC-II-89 was 99% and the specific activity was determined as ~1500 mCi/lµmol at the end of synthesis. HPLC conditions for purification of [$^{18}$F]WC-II-89 included the following: Alltech Ecosoil C$_{18}$ 250×10 mm, 10µ; 25% acetonitrile, 45% methanol, 30% 0.1 M ammonium formate buffer (pH=4.5); 5 mL/min, 251 nm; t$_R$=15 min. A synthesis of [$^{18}$F]WC-II-92 is set forth in FIG. 18.

Inhibition of recombinant human caspase-3 and other caspases by WC-II-89 was assessed using a fluorogenic product, 7-amino-4-methylcoumarin (7-AMC). The IC$_{50}$ values from the enzyme assays are shown in Table 1. WC-II-89 shows high potency for inhibiting caspase-3 and -7, with IC$_{50}$ values at least 150-fold higher versus the initiator caspases-1, -6, -8. This caspase-inhibitory profile indicates that WC-II-89 comprising $^{18}$F can serve as a radiotracer for imaging apoptosis using PET.

In Vivo Studies

All animal studies were performed in accordance with the regulations of the Washington University Institutional Animal Care and Use Committee. Mature male Sprague Dawley rats from Charles River Laboratories were briefly anesthetized with 1-2% isoflurane in oxygen. Each rat received 10-15 µCi of [$^{18}$F]WC-II-89 via the tail vein. Treated rats also received 5 mg/kg cycloheximide in saline via the tail vein three hours prior to radiotracer administration in order to induce caspase-mediated liver apoptosis. At set time-points following radiopharmaceutical injection, rats were again anesthetized and euthanized. Target and non-target organs were removed, weighed, and the radioactivity was counted using a Beckman Gamma 8000 well counter. Standard dilutions of the injected dose were counted along with the samples and uptake was calculated and reported as percent injected dose per gram (% ID/g).

The evaluation of [$^{18}$F]WC-II-89 as a radiotracer for imaging caspase-3 activation was determined using an animal model of chemically-induced apoptosis (35, 36). This model, which uses the protein synthesis inhibitor, cycloheximide (CHX), was previously used in the evaluation of radiolabeled annexin V analogs (37). Tissue morphology and TUNEL staining studies have shown that cycloheximide induces apoptosis in rat liver in both a dose-dependent and time-dependent manner. Within 3 hours of treatment with 1.5, 3, or 10 mg of cycloheximide per kilogram of body weight, apoptosis was induced in rat liver (35, 36). Therefore, we chose 3 hours treatment of 5 mg/kg to induce the maximum apoptosis in rat liver, expecting a high level of caspase-3 activation.

Mature male Sprague-Dawley rats (Charles River Laboratories, Inc., Wilmington, Mass.) were anesthetized with 1-2% isoflurane in oxygen and treated rats were injected via tail vein with five mg/kg CHX/saline solution to activate caspase-mediated apoptosis. Rats were euthanized three hours post-treatment and the organs of interest were immediately snap-frozen in liquid nitrogen, then stored at −80° C. until analysis. Whole organs were homogenized in ice cold T-PER® protein extraction buffer (Pierce Biotechnology, Rockford, Ill.) containing 5 mM DTT, 2 mM EDTA, and Complete® protease inhibitor cocktail tablets (Roche Diagnostics Co., Indianapolis, Ind.). The fully homogenized samples were then sonicated on ice, centrifuged at 4° C. at 14,000 g for fifteen minutes, and the protein-containing supernatant was collected. Forty micrograms of protein from each sample was analyzed using standard immunoblotting techniques. Caspase-3 was probed with anti-caspase-3 antibody (Cell Signaling Technology, Danvers, Mass.) at 1:1000 dilution and horseradish peroxidase-conjugated goat anti-rabbit IgG (Cell Signaling Technology, Danvers, Mass.) at 1:3000. Actin was resolved using anti-β-actin antibody (Cell Signaling Technology, Danvers, Mass.) at 1:1000 dilution and the same secondary antibody as mentioned above. SuperSignal® WestDura extended duration substrate(Pierce Biotechnology, Rockford, Ill.) was used for detection.

MicroPET imaging studies were performed using a Micro-PET Focus 220 and MicroPET Focus 120 scanner (Siemens/CTI, Knoxyille, Tenn.). A control and cycloheximide-treated (5 mg/kg, 3 hours pretreated) rat were anesthetized and a catheter inserted in the jugular vein. Each rat was then placed in the scanner and following a transmission scan, was injected with ~150 µCi of [$^{18}$F]WC-II-89 for a one hour dynamic imaging session. MicroPET images were reconstructed with OSEM-2D data analysis software package (Siemens/CTI, Knoxyille, Tenn.).

The biodistribution results of [$^{18}$F]WC-II-89 in normal and cycloheximide-treated male Sprague-Dawley rats are shown in Table 3 and FIG. 9. In general, the initial uptake was higher for CHX treated rats than control rats. However, the difference between control and treated rats was reduced with time with the exception of the liver and spleen. At one hour after injection (FIG. 9), the uptake in liver and spleen for the treated rats was 94% and 184% higher than the control animals at 1-hour post-i.v. injection of the radiotracer. The increase in uptake of [$^{18}$F]WC-II-89 in the cycloheximide-treated versus control animals is consistent with chemically-induced apoptosis and caspase-3 activation. Since the isatin analogs are competitive inhibitors of caspase-3, [$^{18}$F]WC-II-89 binds to the activated form of caspase-3 in tissues undergoing apoptosis, which explains the slower washout of radioactivity from the liver and spleens of the cycloheximide-treated animals. The results of the biodistribution study also reveal a very low uptake of radioactivity in bone, indicating that defluorination is not a concern with this radiotracer. The result of the biodistribution study shows that [$^{18}$F]WC-II-89 can serve as a PET radiotracer for imaging apoptosis.

TABLE 3

Biodistribution of [$^{18}$F]WC-II-89 in normal and cycloheximide-treated (5 mg/kg, 3 hr. pretreated) male Sprague-Dawley rats (200-250 g).

| organ | animal | % I.D./gram | | |
|---|---|---|---|---|
| | | 5 min. | 1 hr. | 2 hr. |
| blood | control | 2.70 ± 0.21 | 0.11 ± 0.01 | 0.06 ± 0.01 |
| | treated | 3.66 ± 0.40 | 0.16 ± 0.01 | 0.07 ± 0.00 |
| lung | control | 1.42 ± 0.34 | 0.18 ± 0.03 | 0.08 ± 0.01 |
| | treated | 2.08 ± 0.23 | 0.23 ± 0.03 | 0.11 ± 0.02 |

TABLE 3-continued

Biodistribution of [$^{18}$F]WC-II-89 in normal and cycloheximide-treated (5 mg/kg, 3 hr. pretreated) male Sprague-Dawley rats (200-250 g).

| organ | animal | % I.D./gram | | |
|---|---|---|---|---|
| | | 5 min. | 1 hr. | 2 hr. |
| liver | control | 3.13 ± 0.26 | 0.38 ± 0.06 | 0.16 ± 0.02 |
| | treated | 4.02 ± 0.45 | 0.73 ± 0.12 | 0.22 ± 0.03 |
| spleen | control | 1.14 ± 0.08 | 0.15 ± 0.05 | 0.06 ± 0.01 |
| | treated | 2.24 ± 0.41 | 0.43 ± 0.05 | 0.11 ± 0.03 |
| thymus | control | 0.23 ± 0.07 | 0.09 ± 0.01 | 0.04 ± 0.00 |
| | treated | 0.38 ± 0.10 | 0.12 ± 0.02 | 0.06 ± 0.01 |
| kidney | control | 1.25 ± 0.14 | 0.53 ± 0.07 | 0.18 ± 0.04 |
| | treated | 1.18 ± 0.08 | 0.55 ± 0.05 | 0.23 ± 0.05 |
| muscle | control | 0.14 ± 0.01 | 0.08 ± 0.01 | 0.03 ± 0.00 |
| | treated | 0.09 ± 0.00 | 0.10 ± 0.02 | 0.06 ± 0.00 |
| fat | control | 0.12 ± 0.02 | 0.15 ± 0.02 | 0.07 ± 0.01 |
| | treated | 0.09 ± 0.03 | 0.14 ± 0.01 | 0.09 ± 0.01 |
| bone | control | 0.44 ± 0.04 | 0.13 ± 0.02 | 0.15 ± 0.06 |
| | treated | 0.66 ± 0.06 | 0.12 ± 0.01 | 0.13 ± 0.03 |

Figure 12:
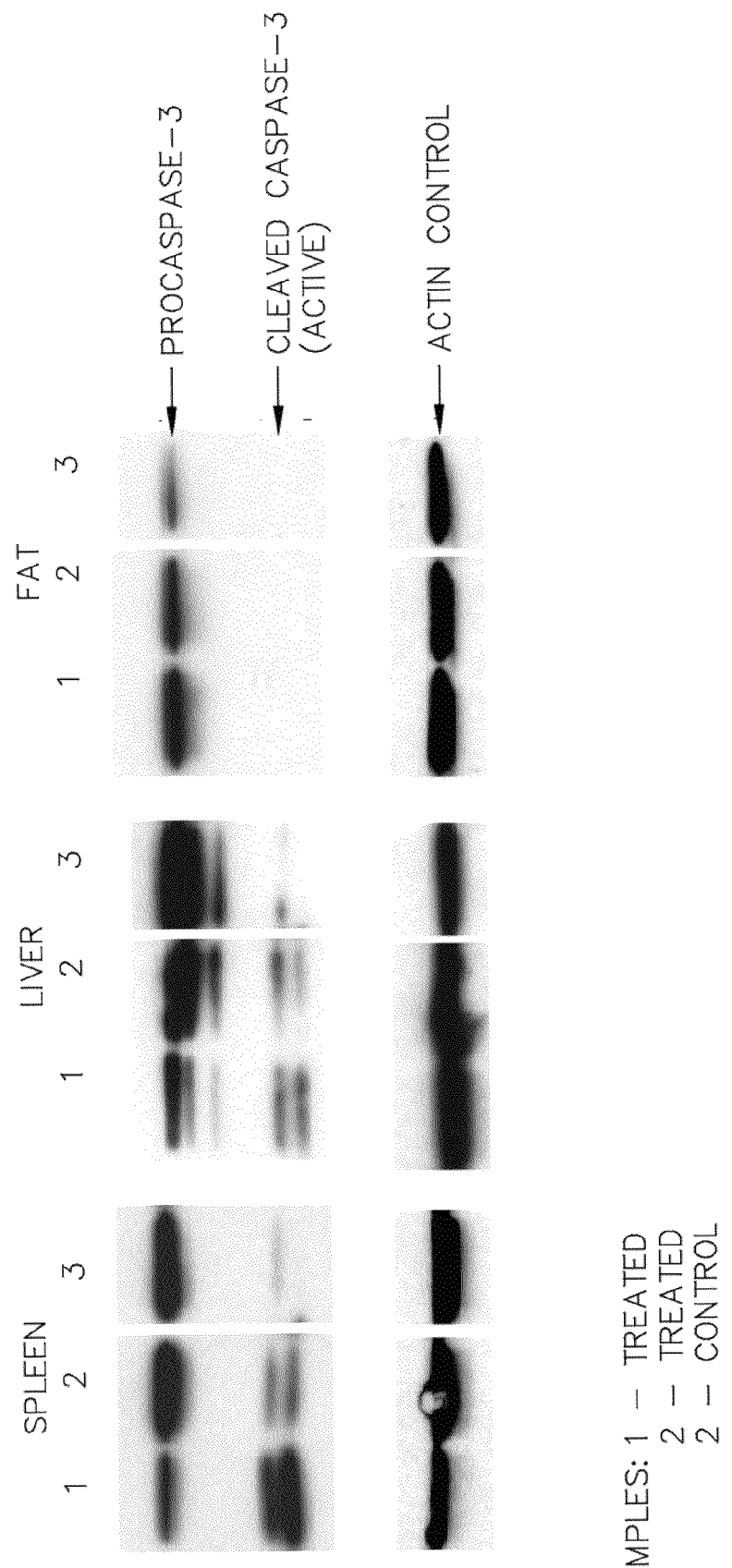
FIG. 12 illustrates a western blot study of control and treated (5 mg/kg, 3 hours pretreated) male Sprague-Dawley rats (200-250 g).

Western blot studies were carried out to measure caspase-3 levels in control and cycloheximide-treated rats in order to correlate caspase-3 activity to the biodistribution results. Western blot analysis of spleen, liver and fat for both control and treated rats are shown in FIG. 12. The level of cleaved caspase-3 in the spleen and liver of the treated rats is much higher than that of the control animals, which is consistent with cycloheximide-induced apoptosis. There was no cleaved caspase-3 in the Western blot of the fat tissues from both control and treated rats. The results of the Western blot studies correlate very well to the biodistribution data of liver, spleen and fat at one-hour post-i.v. injection of the radiotracer as shown in FIG. 9. The good correlation between caspase-3 activity and biodistribution of [$^{18}$F]WC-II-89 in the cycloheximide-treated rats establishes the basis for imaging apoptosis using [$^{18}$F]WC-II-89.

Figure 13:
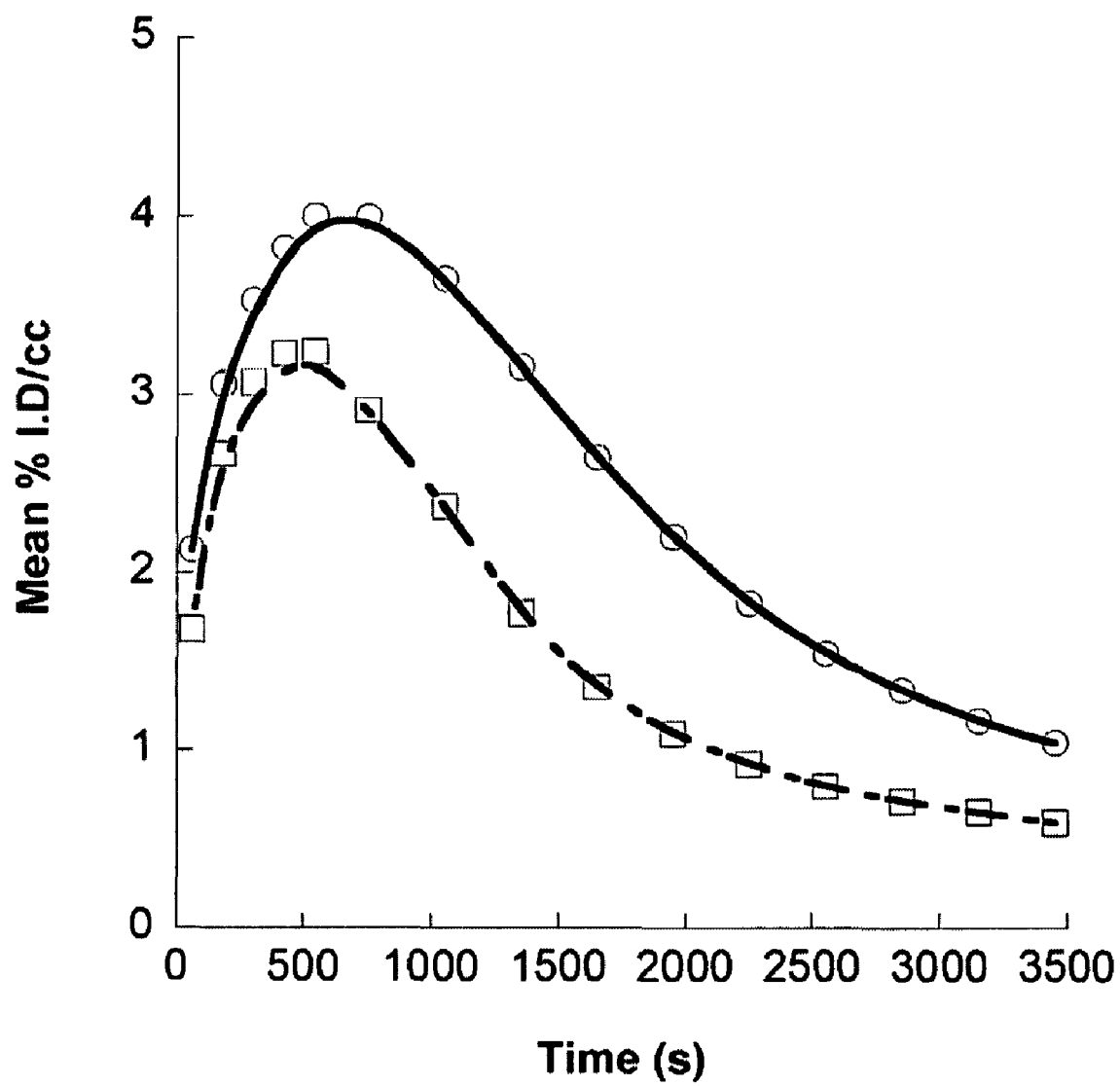
FIG. 13 illustrates tissue time-activity curves (mean percentage of injected dose per cube centimeter) of rat liver. Top curve: cycloheximide-treated rat; bottom curve: control rat.
Figure 14:
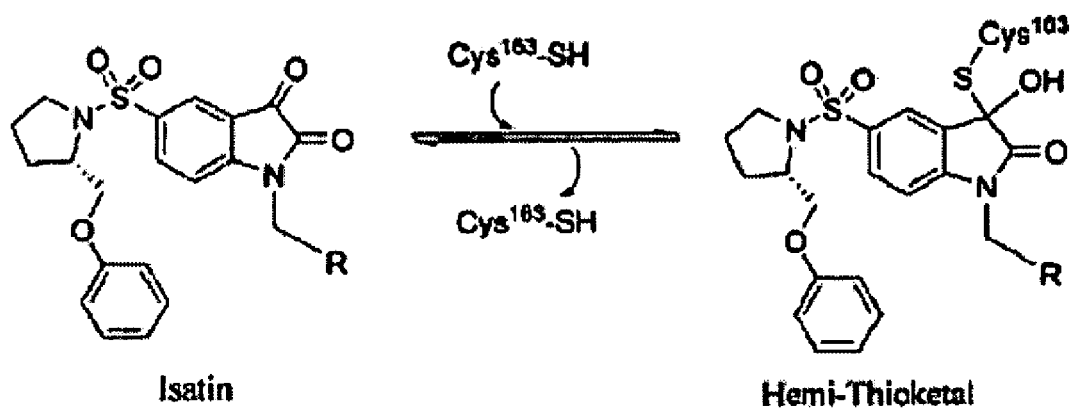
FIG. 14 illustrates binding of the lead compound for the development of caspase-3 based imaging agents to Cys$^{163}$.
Figure 15:
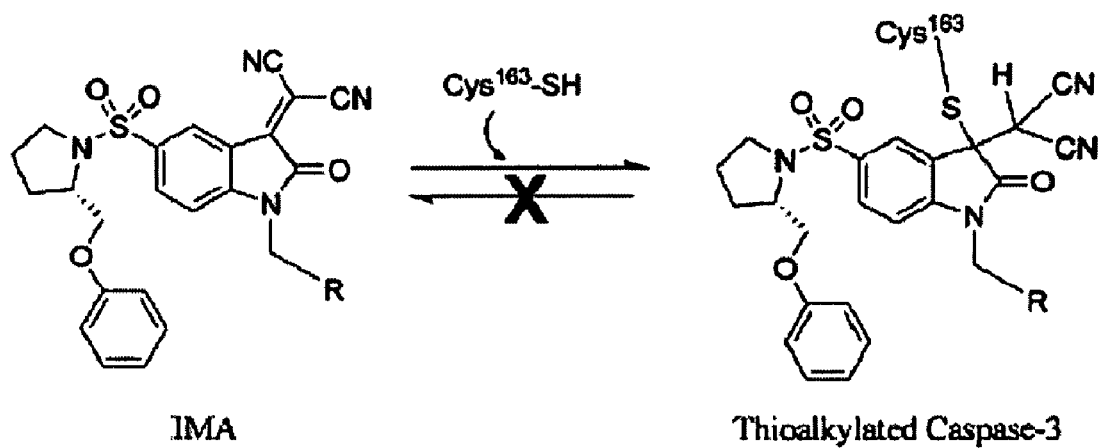
FIG. 15 illustrates hypothesized mechanism of action of the Isatin Michael Acceptors (IMAs) for inhibiting caspase-3/7 activity.
Figure 16:
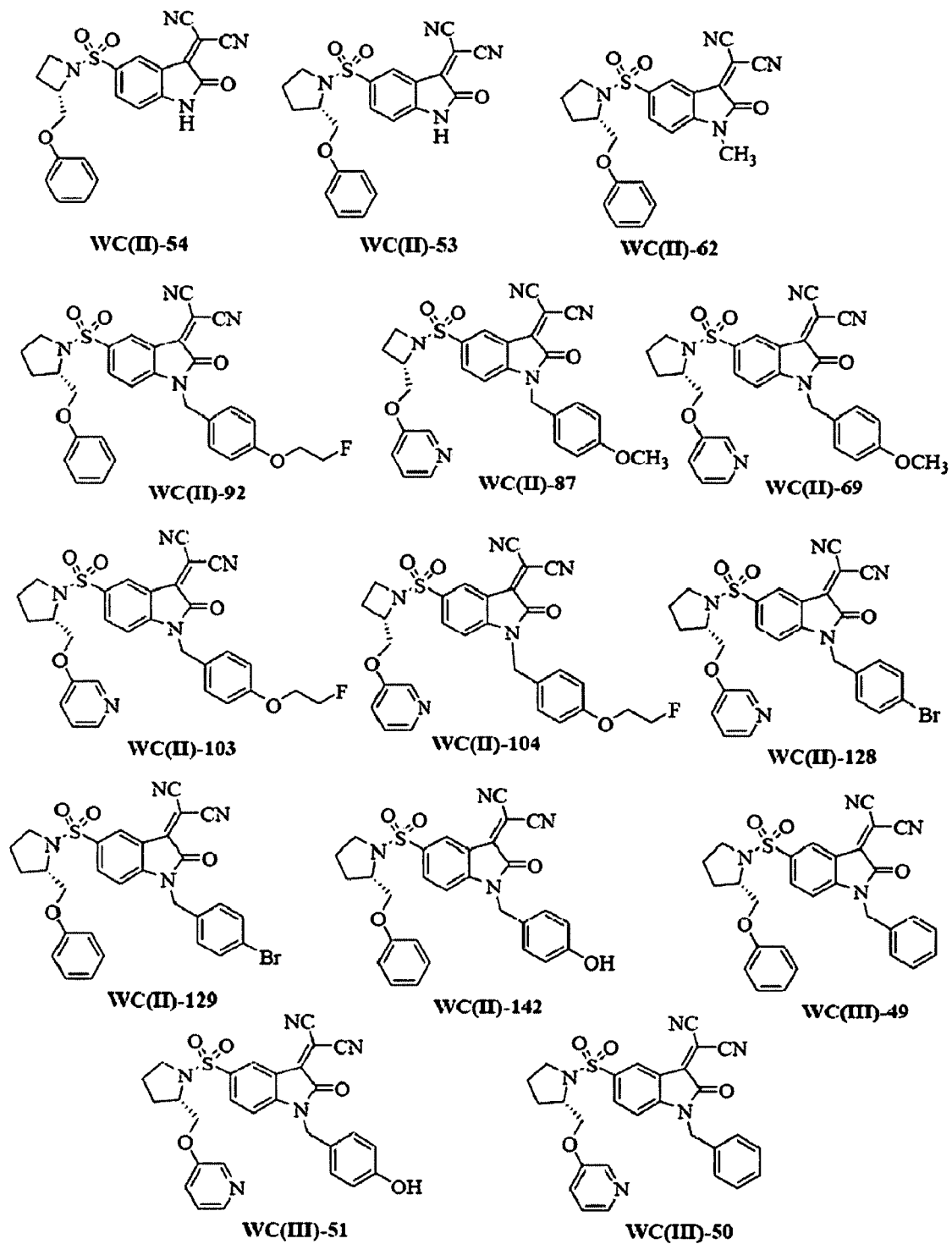
FIG. 16 illustrates structures of the IMA analogues for inhibiting caspase-3/7 activation in apoptosis.
Figure 17:
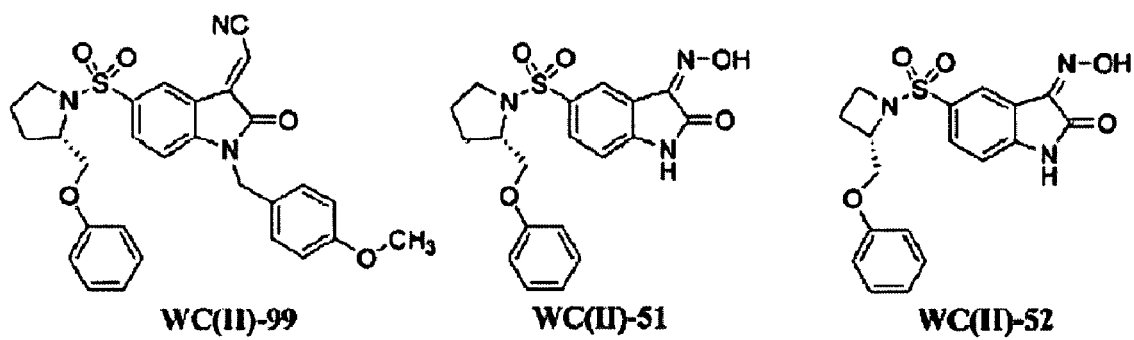
FIG. 17 illustrates structures of some compounds of low potency as caspase-3/7 inhibitors.

The microPET images of the liver region at 10-60 minutes post-i.v. injection of [$^{18}$F]WC-II-89 are shown in FIG. 10. The animal receiving a 3-hour pretreatment of cycloheximide displayed a higher uptake of [$^{18}$F]WC-II-89 in the liver versus the control animal, which was consistent with the results of the biodistribution study. FIG. 13 shows the tissue-time activity curves from the microPET imaging study. The higher peak accumulation of [$^{18}$F]WC-II-89 in the cycloheximide-treated rat liver versus the control animal is consistent with drug-induced caspase-3 activation. The normal rat liver also displayed a faster washout of radioactivity than the cycloheximide-treated liver, which corresponded to caspase-3 activation. This was also confirmed by Western blot analysis of the rat livers following completion of the microPET imaging study.

Enzyme Assays. Inhibition of recombinant human caspase-3 and other caspases by the isatin analogues was assessed using a fluorometric assay by measuring the accumulation of a fluorogenic product, 7-amino-4-methylcoumarin (7-AMC). All of the tested compounds inhibited caspase-3 and caspase-7 in a concentration-dependent manner with similar potency.

Enzyme Inhibition Assays. Recombinant human caspases (3, 6, 7, and 8) and their peptide-specific substrates (Ac-DEVDAMC, Ac-VEID-AMC, Ac-DEVD-AMC, and Ac-IETD-AMC, respectively) were purchased from Sigma-Aldrich (St. Louis, Mo.) with the exception of caspase 1 and its substrate (Ac-YVAD-AMC), which were obtained from BIOMOL Research Laboratories (Plymouth Meeting, Pa.). The enzymatic activity of caspases was determined by measuring the accumulation of the fluorogenic product 7-amino-4-methylcoumarin (AMC). All assays were prepared in 96-well format at a volume of 210 μL per well and consisted of 100 mM Na+ HEPES (pH 7.4), 10% sucrose, 100 mM NaCl, 0.1% CHAPS, 5 mM 2-mercaptoethanol, 2 mM EDTA, 10 μM Ac-YVAD-AMC (caspase 1); 20 mMNa$^+$ HEPES (pH 7.4), 10% sucrose, 100 mMNaCl, 0.1% CHAPS, 2 mM EDTA, 10 μM Ac-DEVD-AMC (caspase 3); 20 mM Na$^+$ HEPES (pH 7.4), 10% sucrose, 100 mM NaCl, 0.1% CHAPS, 2 mM EDTA, 10 μM Ac-VEID-AMC (caspase 6); 20 mM Na+ HEPES (pH 7.4), 100 mM NaCl, 10% sucrose, 0.1% CHAPS, 5 mM 2-mercaptoethanol, 2 mM EDTA, 10 μM Ac-DEVD-AMC (caspase 7); 20 mM Na+ HEPES (pH 7.4), 10% sucrose, 100 mM NaCl, 0.1% CHAPS, 2 mM EDTA, 10 μM Ac-IETD-AMC (caspase 8).

Recombinant caspases were first assayed to determine the optimal concentration for each experiment. Optimal concentrations were based in the linear range of the enzyme activation curves. Peptide inhibitors with known IC$_{50}$ values were tested together with the compounds as a control for each caspase assay. Peptide inhibitors, Ac-DEVD-CHO (caspase-3 and -7), Ac-VEID-CHO (caspase-6), and Ac-IETD-CHO (caspase-8) were purchased from Sigma-Aldrich (St. Louis, Mo.) with exception of caspase-I specific inhibitor (Ac-YVAD-CHO) which was acquired from BIOMOL Research Laboratories (Plymouth Meeting, Pa.). Peptide and nonpeptide inhibitors were dissolved in DMSO, and a 2 serial dilution was performed prior to screening in order to obtain desired concentrations. 10 μL was added to each well containing 100 μL caspase solution and allowed to incubate on ice for 30 min. A 100 μL substrate solution was added to each well, and plates were incubated for 1-2 h at 37° C. The final concentration of DMSO in all wells was 5% of the total volume. In caspase-1 and caspase-7 assays, 10 mM 2-mercaptoethanol was added to the substrate solution for full activation of the enzymes.

The amount of AMC released was determined by using a Victor3 microplate fluorometer (Perkin-Elmer Life Sciences, Boston, Mass.) at excitation and emission wavelengths 355 nm and 460 nm, respectively. Compounds were tested in duplicate, and IC$_{50}$ curves were calculated for all inhibitors assayed. Final IC$_{50}$s were the average of three independent experiments.

Enzyme Kinetic Studies. The inhibition profile for compound 21c was determined for caspase-3 in the assay buffer. The concentration of Ac-DEVD-AMC was varied from 6.25 to 100 μM, and the concentration of 21c was varied from 0 to 20 nM. The kinetic parameters of 21c were obtained by fitting initial-rate data to $$v = \frac{V_m S}{K_m\left(1 + \frac{1}{K_i}\right) + S} \quad (1)$$

where v is the observed velocity, S is the substrate concentration, Vm is the velocity at saturating substrate, Km is the Michaelis constant of the substrate, I is the inhibitor concentration, and Ki is the dissociation constant of the inhibitor from the E·I complex. The data were analyzed using GraFit 4.0 (Erithacus Software, Staines, U.K.)

The IC$_{50}$ values from the enzyme assays are summarized in Tables 1-3. Alkylation of the isatin nitrogen of 10 with a benzyl group (i.e., 2) or substituted benzyl group (i.e., 11c-e) resulted in a 10 to 20-fold increase in potency for inhibiting caspase-3, and a 9 to 37-fold increase in potency for inhibiting caspase-7. The isatin analogues were also evaluated for their inhibitory activity against a panel of three other caspases (caspases-1, -6, and -8). As shown in Table 4, they demonstrated high selectivity against caspase-3 and -7, with IC$_{50}$ values at least 100-fold higher versus caspases-1, -6, and -8.

TABLE 4

Inhibitor Selectivity of Pyrrolidine Isatin
Analogues for Caspases-1, -3, -6, -7, and -8

| Compound | IC$_{50}$ (nM) | | | | | Log P |
|---|---|---|---|---|---|---|
| | caspase-1 | caspase-3 | caspase-6 | caspase-7 | caspase-8 | |
| 10 | >10000 | 240.0 ± 10.0 | >5000 | 540.0 ± 56.6 | >50000 | 2.23 |
| 11a | >20000 | 119.2 ± 17.0 | >5000 | 310.0 ± 14.1 | >50000 | 2.27 |
| 2 | >10000 | 12.2 ± 0.3 | >5000 | 28.0 ± 0.7 | >50000 | 4.05 |
| 11b | >10000 | 14.5 ± 1.6 | >5000 | 21.8 ± 3.5 | >50000 | 3.96 |
| 11c | >50000 | 12.1 ± 2.1 | >5000 | 23.0 ± 1.4 | >50000 | 4.1 |
| 11d | >50000 | 12.4 ± 2.1 | >5000 | 41.0 ± 1.4 | >50000 | 4.54 |
| 11e | >50000 | 12.0 ± 1.5 | >5000 | 34.8 ± 0.4 | >50000 | 3.39 |
| 11f | >5000 | 13.5 ± 2.4 | >5000 | 44.0 ± 0.1 | >50000 | 3.31 |
| 11g | >50000 | 10.3 ± 1.5 | >5000 | 14.5 ± 0.9 | >50000 | 2.67 |
| 11h | >50000 | 21.3 ± 3.2 | >5000 | 58.0 ± 2.8 | >50000 | 2.67 |
| 11i | >50000 | 9.1 ± 1.8 | >5000 | 22.2 ± 4.0 | >50000 | 2.67 |

Reversibility Assay

In these experiments, Recombinant caspase 3 (2 ng/μl) was either left untreated or incubated with Z-DEVD-FMK (3 μM), a well known irreversible inhibitor of caspase 3, or 30d (3 μM) for 1 hour on ice. The caspase 3 activity was fully inhibited by z-DEVD-FMK (3 μM) or 30d (3 μM) under this condition. Then the mixtures were run through the gel filtration column (Bio-Spin 6 Tris columns from Bio-Rad Laboratories, Hercules, Calif.) to remove the free compounds according to the manufacture's instruction. Briefly, 50 μl of the incubation mixture was loaded on the top of the column. The column was then centrifuged at 1000×g for 4 min at 4° C. The resulting elutant was designated as elutant A (for no treatment sample), B (for Z-DEVD-FMK-treated sample) or C (for 30d-treated sample). The elutant was assayed for caspase 3 activity as described in enzyme inhibition assays above. Briefly, 40 μl of the elutant, 60 μl assay buffer and 100 μl substrate (10 μM Ac-DEVD-AMC) were incubated for 1 hour at 37° C. Amount of AMC released was determined using a Victor microplate fluorometer. The recovered caspase-3 activity after gel filtration (%) was calculated. The results show that elutant B exhibited little caspase 3 activity compared to elutant A, suggesting that Z-DEVD-FMK irreversibly binds to caspase 3 and thus can not be removed from caspase 3 by gel filtration column. The results also showed that elutant C remained full caspase 3 activity compared to elutant A, indicating that 30d reversibly binds to caspase 3 and thus can be removed by gel filtration column.

TABLE 5

Inhibitor Selectivity of the Azetidine Isatin Analogues
17, 18a-i for Caspases-1, -3, -6, -7, and -8

| Compound | IC$_{50}$ (nM) | | | | | Log P |
|---|---|---|---|---|---|---|
| | caspase-1 | caspase-3 | caspase-6 | caspase-7 | caspase-8 | |
| 17 | >10000 | 286.7 ± 24.7 | >5000 | 1350.0 ± 141.4 | >50000 | 1.66 |
| 18a | >10000 | 91.7 ± 7.6 | >5000 | 362.5 ± 3.5 | >50000 | 1.71 |
| 18b | >10000 | 9.7 ± 1.6 | >5000 | 29.5 ± 4.9 | >50000 | 3.49 |
| 18c | >50000 | 8.4 ± 1.2 | >5000 | 23.2 ± 3.0 | >50000 | 3.4 |
| 18d | >50000 | 11.3 ± 1.2 | >5000 | 26.7 ± 7.2 | >50000 | 3.97 |
| 18e | >10000 | 8.8 ± 1.4 | >5000 | 21.0 ± 5.6 | >50000 | 3.54 |
| 18f | >10000 | 9.4 ± 0.3 | >5000 | 26.0 ± 5.2 | >50000 | 3.54 |
| 18g | >50000 | 10.9 ± 1.4 | >5000 | 17.0 ± 3.0 | >50000 | 2.11 |
| 18h | >50000 | 29.2 ± 5.2 | >5000 | 135.0 ± 7.1 | >50000 | 2.11 |
| 18i | >10000 | 5.8 ± 1.0 | >5000 | 22.7 ± 3.1 | >50000 | 2.11 |

TABLE 6

Selectivity Profile of some Pyridine Analogues within the Caspase Family

| Compound | IC$_{50}$ (nM) | | | | | Log P |
|---|---|---|---|---|---|---|
| | caspase-1 | caspase-3 | caspase-6 | caspase-7 | caspase-8 | |
| 20 | >5000 | 58.3 ± 7.6 | >5000 | 214.9 ± 49.5 | >50000 | 1.17 |
| 21a | >10000 | 23.3 ± 3.1 | >5000 | 94.9 ± 21.6 | >50000 | 1.21 |
| 21b | >10000 | 5.2 ± 1.6 | >5000 | 14.1 ± 3.4 | >50000 | 2.99 |
| 21c | >10000 | 3.9 ± 0.9 | >5000 | 15.1 ± 1.2 | >50000 | 2.91 |
| 21d | >50000 | 4.4 ± 1.4 | >5000 | 23.3 ± 0.7 | >50000 | 3.48 |
| 21e | >10000 | 8.4 ± 2.0 | >5000 | 15.1 ± 0.1 | >50000 | 3.04 |
| 23 | >5000 | 20.4 ± 1.7 | >5000 | 142.3 ± 22.6 | >50000 | 1.04 |

The azetidine analogue 17 had a similar potency for inhibiting caspase-3 as that of the corresponding pyrrolidine analogue 10. However, compound 17 was >2-fold less potent for inhibiting caspase-7 relative to the corresponding pyrrolidine analogue, 10. Substitution of 17 with either a benzyl (i.e., 18b), a substituted benzyl (18c-f), or a pyridylmethyl group (18g-i) resulted in a 10 to 50-fold increase in potency against caspase-3 and a 10 to 80-fold increase in potency for inhibiting caspase-7 relative to 17 (Table 5). Again, these compounds exhibited at least 100-fold greater selectivity for caspase-3 and -7 versus caspases-1, -6, and -8.

Interestingly, a higher caspase-3 potency was achieved upon replacing the benzene ring of the 2-(phenoxymethyl) pyrrolidine moiety with a pyridine ring (Table 6). All pyridine-containing analogues had a lower $IC_{50}$ value for inhibiting caspase-3 than the corresponding benzene-containing congeners (eg., 11a vs 21a, 11d vs 21d). Compound 21c was found to be the most potent inhibitor of caspase-3, with $IC_{50}$ of 3.9 nM. These compounds demonstrated similar potency against caspase-3 and 7, but at least 100 fold less potent versus caspases-1, -6, and -8.

Figure 3:
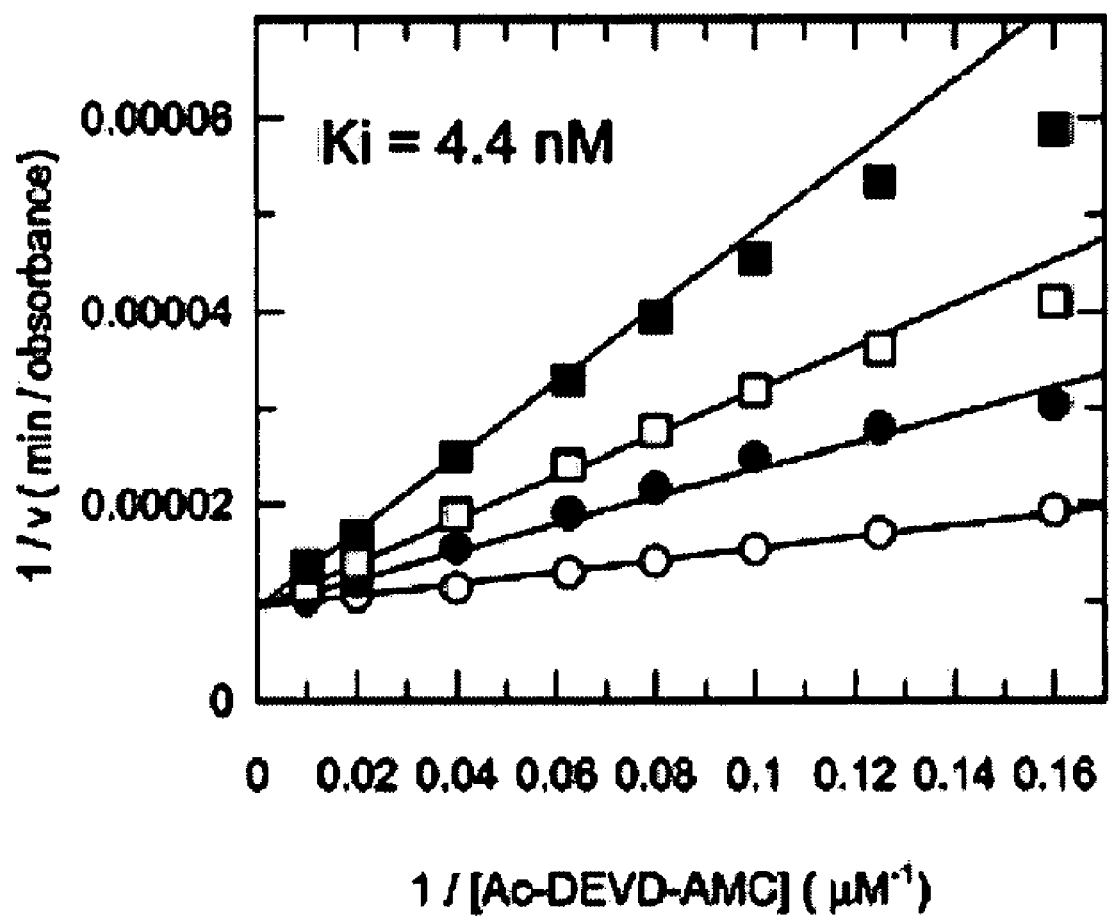
FIG. 3 illustrates competitive inhibition of caspase-3 by 21c. The concentration of 21c was 0 (○), 5 (●), 10 (□), and 20 nM (■).
Figure 4:
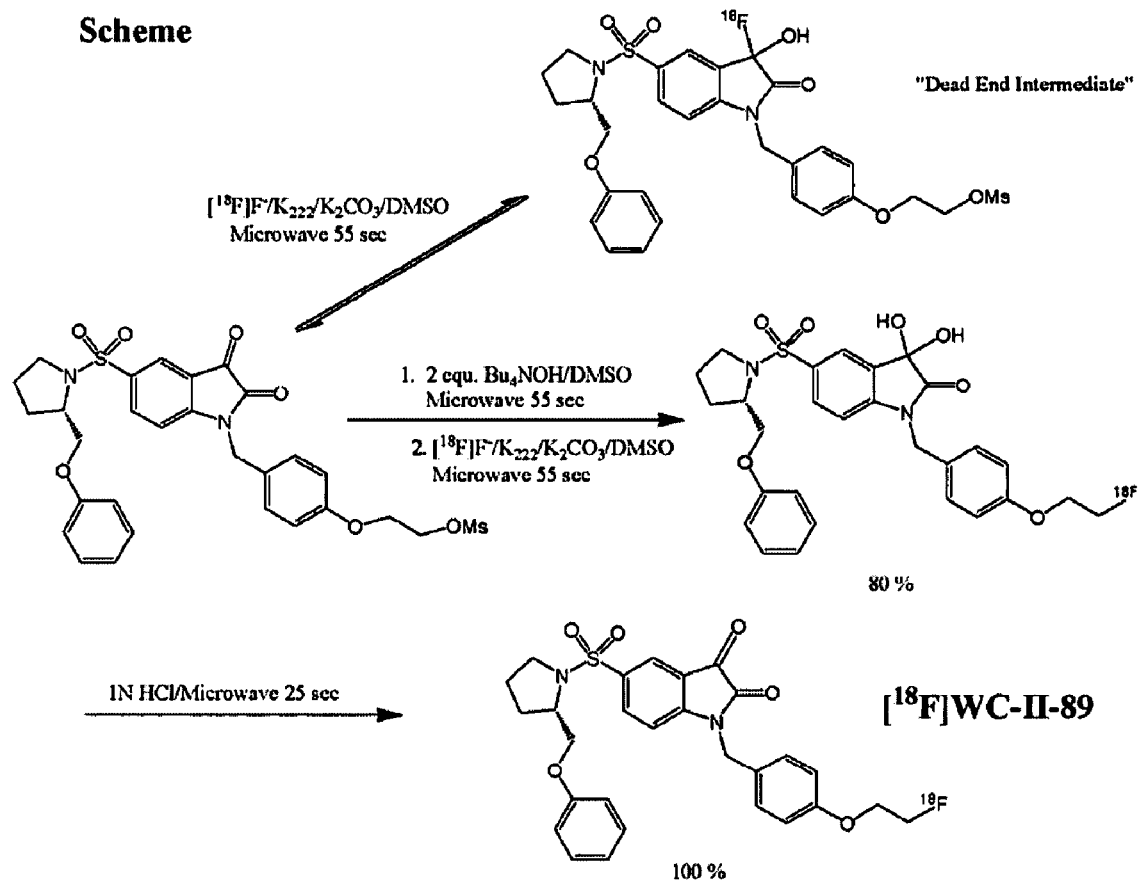
FIG. 4 illustrates a synthesis scheme for [$^{18}$F]WC-II-89.

Kinetic studies were also conducted in order to determine the mechanism of inhibition of caspase-3 activity by compound 21c. The kinetic pattern indicated that 21c displays competitive inhibition versus Ac-DEVD-AMC with a calculated Ki value of 4.4 nM (FIG. 3). These data are consistent with previous studies demonstrating that the isatin analogues bind to the catalytic site of activated caspase-3 (16)

Figure 1:
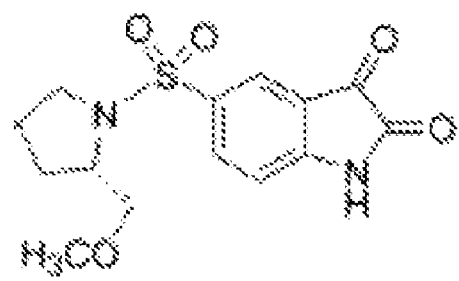
FIG. 1 illustrates structure of isatin sulfonamide analogues reported previously.
Figure 1:
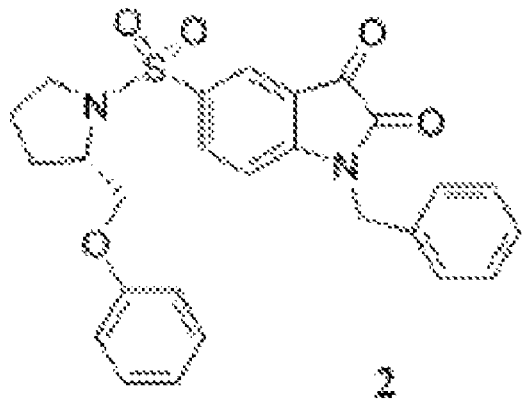
Figure 1:
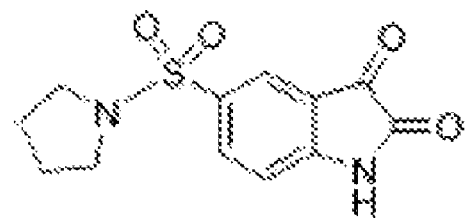
Figure 1:
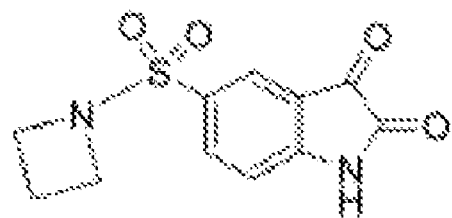
Figure 2:
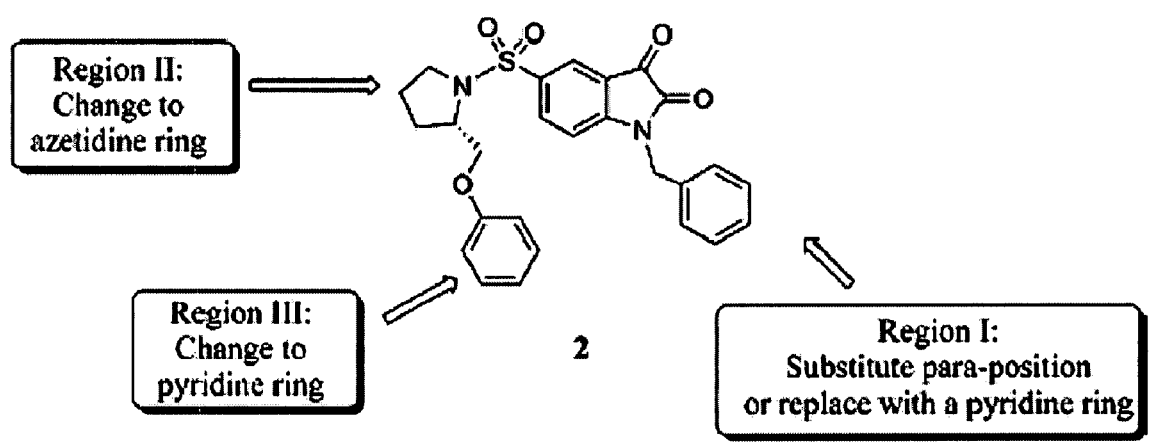
FIG. 2 illustrates a strategy used in the current structure-activity relationship study.

In some aspects, the present teachings include the absence of a substituent effect in the aromatic ring of the N-benzyl moiety of compound 2. The results outlined in Table 4 indicate that either substitution of the para position of 2 or replacement of the benzene ring with a pyridine ring results in little change in potency for inhibiting caspase-3 and caspase-7. These results are consistent with the earlier observations regarding the substitution of the isatin nitrogen with hydrophobic substituents (16). A second, and somewhat unexpected, observation was the similar potency between the pyrrolidine analogues 11b-i and the azetidine analogues 18b-i, given the difference in potency for inhibiting caspase-3 by compound 3 and compound 4 (FIG. 1). Another unexpected observation was the high potency of the pyridine analogues 21b-e relative to their phenyl congeners, 2 and 11b-d. These data suggest a possible hydrophilic interaction between the phenoxymethyl moiety and the S3 binding domain of caspase-3.

Substitution of the pyridine ring for a benzene ring in the phenoxymethyl moiety can also result in a dramatic reduction in the overall lipophilicity of the isatin analogues (18,19). For example, compound 2 has a calculated log P value of 4.05 whereas the corresponding pyridine analogue, 21b, has a calculated log P value of 2.99. Therefore, in some aspects, a pyridine analogue of the present teachings can have a higher potency for inhibiting activated caspase-3 in situations in which the compound crosses or interacts with an intact cell membrane.

Log P value of the IMA analogs are lower than the corresponding values of non-Michael acceptor isatin analogs (e.g., 25d vs. 27d, Log P 4.82 vs. 4.28; 28b vs. 30b, 2.25 vs. 1.77; and 28c vs. 30c, 3.76 vs. 3.22, respectively FIG. 19, table 7)). This lower Log P value of the IMA caspase-3 inhibitor increases the drug's ability to penetrate the cell in vivo and label the target.

TABLE 7

Selectivity profiles of some Isatin Michael Acceptors

| # | $IC_{50}$ (nM) | | | | | Log P |
|---|---|---|---|---|---|---|
| | Casp-1 | Casp-3 | Casp-6 | Casp-7 | Casp-8 | |
| 25d | >15000 | 9.85 ± 0.9 | 8900 ± 424 | 34.8 ± 1.4 | >50000 | 4.82 |
| 28b | >15000 | 3.9 ± 0.6 | 9550 ± 354 | 11.7 ± 1.0 | >50000 | 2.25 |
| 28c | >15000 | 3.6 ± 0.5 | 5025 ± 318 | 6.6 ± 0.1 | >50000 | 3.76 |
| 26 | 1830 ± 128 | 272 ± 24.7 | 407 ± 15 | 1585 ± 163 | >50000 | 1.07 |
| 27a | 2825 ± 248 | 119.3 ± 4.0 | 698 ± 94 | 785 ± 276 | >50000 | 1.71 |
| 27b | 6220 ± 1250 | 27.8 ± 2.5 | 918 ± 151 | 51.7 ± 6.2 | >50000 | 3.50 |
| 27c | 2300 ± 250 | 31.8 ± 6.2 | 744 ± 48 | 126.0 ± 19.3 | >50000 | 2.77 |
| 27d | 5700 ± 850 | 20.1 ± 1.3 | 840 ± 125 | 92.2 ± 11.8 | >50000 | 4.28 |
| 30a | 3250 ± 450 | 7.6 ± 1.1 | 823 ± 86 | 32.8 ± 4.9 | >50000 | 2.45 |
| 30b | 2720 ± 580 | 7.8 ± 1.9 | 650 ± 22 | 28.3 ± 5.4 | >50000 | 1.77 |
| 30c | 3400 ± 0 | 5.1 ± 0.7 | 515 ± 77 | 26.3 ± 0.8 | >50000 | 3.22 |
| 30d | 3900 ± 530 | 7.8 ± 1.5 | 610 ± 113 | 29.6 ± 1.4 | >50000 | 2.36 |

In summary, the present inventors disclose, in various aspects, the synthesis and activity of a series of isatin analogues having a high potency for inhibiting the executioner caspases, caspase-3, and caspase-7. In various configurations, the inventors discoveries extend the structure-activity relationships of this class of compounds and provide further insight into the development of non-peptide-based inhibitors of caspase-3 and caspase-7. In various aspects, the compounds described above can be useful probes for determining the effectiveness of inhibiting caspase-3 and caspase-7 for minimizing tissue damage in pathological conditions characterized by unregulated apoptosis.

EXAMPLES

Various aspects of the present teachings can be illustrated by the following non-limiting examples. The following examples are illustrative, and are not intended to limit the scope of the claims. The description of a composition or a method in an example does not imply that a described article or composition has, or has not, been produced, or that a described method has, or has not, been performed, except for results presented in past tense.

All reactions in the Examples were carried out under an inert nitrogen atmosphere with dry solvents using anhydrous conditions unless otherwise stated. Reagents and grade solvents were used without further purification. Flash column chromatography was conducted using Scientific Adsorbents, Inc. silica gel, 60a, "40 Micron Flash" (32-63 μm). Melting points were determined using MEL-TEMP 3.0 apparatus and uncorrected. $^1$H NMR spectra were recorded at 300 MHz on a Varian Mercury-VX spectrometer. All chemical shift values are reported in ppm (δ). Elemental analyses (C, H, N) were determined by Atlantic Microlab, Inc.

Example 1

2,3-Dioxo-2,3-dihydro-1H-indole-5-sulfonyl Chloride (6). (16) Phosphorus oxychloride (13.2 mL, 141.6 mmol) was added to a solution of 5-isatinsulfonic acid (5), sodium salt hydrate (8.0 g, 30.0 mmol) in tetramethylene sulfone (40 mL). The mixture was heated to 60° C. for 3 h, then cooled to 0° C. The reaction mixture was poured into 150 g of ice. The solid was filtered out and washed with cold water, then the solid was dissolved in ethyl acetate (100 mL), washed with water (50 mL×2) and saturated NaCl (50 mL), and dried over $Na_2SO_4$. The ethyl acetate was evaporated in reduced pressure to afford 6.12 g (83%) of 6 as a pale yellow solid, mp 188.2-190.1° C. $^1H$ NMR (300 MHz, DMSO) δ 11.1 (s, 1H), 7.82 (dd, J=8.4 Hz, J=1.8 Hz, 1H), 7.60 (s, 1H), 6.89 (d, J=8.1 Hz, 1H).

Example 2

((S)-1-(tert-Butoxycarbonyl)pyrrolidin-2-yl)methyl 4-Methylbenzesulfonate (8). A solution of 7 (5.03 g, 25.0 mmol) and pyridine (15 mL) in $CH_2Cl_2$ (50 mL) was reacted with p-toluenesulfonyl chloride (5.96 g, 31.2 mmol) at 0° C. The mixture was stirred overnight at room temperature, then $CH_2Cl_2$ (50 mL) was added. The solution was washed with water (50 mL×2), 10% citric acid (50 mL×2), and saturated NaCl (50 mL), and dried over $Na_2SO_4$. After evaporation of the $CH_2Cl_2$, the crude product was purified with hexanes-ethyl ether (1:1) to afford 8.9 g (100%) of 8 as a colorless oil. $^1H$ NMR (300 MHz, DMSO) δ 7.78 (d, J=8.4 Hz, 2H), 7.49 (d, J=8.1 Hz, 2H), 4.02 (m, 2H), 3.83 (m, 1H), 3.18 (m, 2H), 2.43 (s, 3H), 1.92 (m, 1H), 1.72 (m, 3H), 1.35 and 1.29 (s, 9H).

Example 3

(S)-tert-Butyl 2-(Phenoxymethyl)pyrrolidine-1-carboxylate (9). A solution of phenol (7.37 g, 78.4 mmol) in THF (100 mL) was reacted with 60% NaH (3.14 g, 78.4 mmol) at 0° C. in 20 min. The mixture was warmed to room temperature and stirred 20 min, then a solution of 8 (5.57 g, 15.7 mmol) in THF (25 mL) was added. The mixture was heated to reflux for 24 h. After evaporation of the THF, ether (200 mL) was added, washed with water (40 mL), 1 N NaOH (40 mL×3), and saturated NaCl (40 mL), and dried over $Na_2SO_4$. After evaporation of the ether, the crude product was purified with hexanes-ether (2:1) to afford 2.37 g (54%) of 9 as a colorless oil. $^1H$ NMR (300 MHz, DMSO) δ 7.28 (t, J=8.4 Hz, 2H), 6.95 (m, 3H), 4.04 (m, 2H), 3.87 (m, 1H), 3.27 (m, 2H), 1.93-1.80 (m, 4H), 1.41 (s, 9H).

Example 4

(S)-5-(2-Phenoxymethyl-pyrrolidine-1-sulfonyl)-1H-indole-2,3-dione (10). To a solution of 9 (1.46 g, 5.2 mmol) in $CH_2Cl_2$ (5 mL) was added trifluoroacetic acid (5 mL) at 0° C. The mixture was stirred at 0° C. for 15 min. After evaporation of the solvent in vacuo, $CH_2Cl_2$ (15 mL) and triethylamine (2 mL) were added, then a solution of 6 (1.44 g, 5.9 mmol) in THF (25 mL) was added at 0° C. The reaction mixture was stirred overnight at room temperature. The solvent was evaporated in vacuo, then ethyl acetate (150 mL) was added, washed with water (50 mL×2) and saturated NaCl (50 mL), and dried over $Na_2SO_4$. After evaporation of the ethyl acetate, the crude product was purified with ether to afford 1.7 g (84%) of 10 as a yellow solid, mp 204.5-205.9° C. $^1H$ NMR (300 MHz, $CDCl_3$) δ 8.94 (s, 1H), 7.77 (dd, J=8.25 Hz, J=2.1 Hz, 1H), 7.67 (s, 1H), 7.02 (t, J=8.7 Hz, 2H), 6.84 (d, J=8.1 Hz, 1H), 6.69 (t, J=7.2 Hz, 1H), 6.63 (d, J=7.8 Hz, 2H), 3.89 (m, 1H), 3.75-3.66 (m, 2H), 3.23 (m, 1H), 2.96 (m, 1H), 1.72 (m, 2H), 1.54-1.42 (m, 2H). LRMS (FAB) m/e: 387.1 (M+H, 100). Anal. Calcd for $C_{19}.N_2O_5S$: C, 59.06, H, 4.70; N, 7.25. Found: C, 58.99, H, 4.74, N, 7.11.

Example 5

(S)-1-Methyl-5-(2-phenoxymethyl-pyrrolidine-1-sulfonyl)-1H-indole-2,3-dione (11a). To a solution of 10 (193 mg, 0.5 mmol) in DMF (3 mL) was added 60% NaH (30 mg, 0.75 mmol) at room temperature. The mixture was stirred 15 min, then iodomethane (0.5 mL) was added. The mixture was stirred overnight at ambient temperature, then ether (75 mL) was added, washed with water (30 mL) and saturated NaCl (30 mL), and dried over $Na_2SO_4$. After evaporation of the solvent, the crude product was purified with ether to afford 85 mg (43%) of 11a as a yellow solid, mp 160.1-160.9° C. $^1H$ NMR (300 MHz, $CDCl_3$) δ 8.07 (dd, J=8.25 Hz, J=2.1 Hz, 1H), 8.01 (s, 11H), 7.25 (t, J=8.4 Hz, 2H), 6.92 (m, 3H), 6.81 (d, J=7.8 Hz, 2H), 4.15 (dd, J=9.0 Hz, J=2.7 Hz, 1H), 4.00 (m, 1H), 3.92 (m, 1H), 3.51 (m, 1H), 3.30 (m, 1H), 3.26 (s, 3H), 2.04 (m, 2H), 1.81 (m, 2H). Anal. Calcd for $C_{20}H_{20}N_2O_5S$: C, 59.99, H, 5.03; N, 7.00. Found: C, 59.80, H, 5.03; N, 6.91.

Example 6

(S)-1-Benzyl-5-(2-phenoxymethyl-pyrrolidine-1-sulfonyl)-1H-indole-2,3-dione (2) was prepared according to the same procedure for compound 11a, except using benzyl bromide, and purified with hexanes-ether (1:2) to afford 152 mg (64%) of 2 as a yellow solid, mp 97.2-99.1° C. $^1H$ NMR (300 MHz, $CDCl_3$) δ 8.01 (d, J=1.5 Hz, 1H), 7.94 (dd, J=8.4 Hz, J=1.8 Hz, 1H), 7.36 (m, 5H), 7.22 (m, 2H), 6.95-6.79 (m, 4H), 4.92 (s, 2H), 4.15 (dd, J=8.85 Hz, J=2.4 Hz, 1H), 3.97-3.87 (m, 2H), 3.49 (m, 1H), 3.23 (m, 1H), 2.01 (m, 2H), 1.78 (m, 2H). Anal. Calcd for $C_{26}H_{24}N_2O_5S$: C, 65.53, H, 5.08; N, 5.88. Found: C, 65.27, H, 5.32; N, 5.58.

Example 7

(S)-1-(4-Methoxybenzyl)-5-(2-phenoxymethyl-pyrrolidine-1-sulfonyl)-1H-indole-2,3-dione (11b) was prepared according to the same procedure for compound 11a, except using 4-methoxybenzyl chloride, and purified with hexanesether (1:3) to afford 175 mg (69%) of 11b as a yellow solid, mp 126.7-128.8° C. $^1H$ NMR (300 MHz, $CDCl_3$) δ 8.00 (s, 1H), 7.95 (dd, J=8.25 Hz, J=2.1 Hz, 1H), 7.28-7.21 (m, 4H), 6.96-6.80 (m, 6H), 4.86 (s, 2H), 4.18-4.11 (m, 1H), 3.97-3.88 (m, 2H), 3.80 (s, 3H), 3.50 (m, 1H), 3.23 (m, 1H), 2.02 (m, 2H), 1.78 (m, 2H). Anal. Calcd for $C_{27}H_2(N_2O_6S$: C, 64.02, H, 5.17; N, 5.53. Found: C, 64.76, H, 5.24; N, 5.06.

Example 8

(S)-1-(4-Fluorobenzyl)-5-(2-phenoxymethyl-pyrrolidine-1-sulfonyl)-1H-indole-2,3-dione (11c) was prepared according to the same procedure for compound 11a, except using 4-fluorobenzyl bromide, and purified with hexanes-ether (1:2) to afford 196 mg (79%) of 11c as an orange solid, mp 74.5-75.4° C. $^1H$ NMR (300 MHz, $CDCl_3$) δ 7.99 (s, 1H), 7.95 (dd, J=8.25 Hz, J=2.1 Hz, 1H), 7.34-7.19 (m, 4H), 7.06 (t, J=8.7 Hz, 2H), 6.92 (t, J=7.2 Hz, 1H), 6.87-6.79 (m, 3H), 4.89 (s, 2H), 4.13 (m, 1H), 3.93 (m, 2H), 3.47 (m, 1H), 3.23 (m, 1H), 2.01 (m, 2H), 1.78 (m, 2H). Anal. Calcd for $C_{26}H_{23}FN_2O_5S$: C, 63.15, H, 4.69; N, 5.66. Found: C, 63.05, H, 4.69; N, 5.60.

Example 9

(S)-1-(4-Methylthiobenzyl)-5-(2-phenoxymethyl-pyrrolidine-1-sulfonyl)-1H-indole-2,3-dione (11d) was prepared according to the same procedure for compound 11a, except using 4-methylthiobenzyl bromide, and purified with hexanes-ether (1:2) to afford 152 mg (64%) of 11d as a yellow solid, mp 175.4-176.8° C. $^1$H NMR (300 MHz, CDCl$_3$) δ 8.05 (s, 1H), 7.99 (d, J=10.5 Hz, 1H), 7.27 (m, 6H), 6.96 (t, J=7.2 Hz, 1H), 6.86 (t, J=8.1 Hz, 3H), 4.90 (s, 2H), 4.19 (d, J=8.7 Hz, 1H), 3.96 (m, 2H), 3.53 (m, 1H), 3.25 (m, 1H), 2.50 (s, 3H), 2.05 (m, 2H), 1.82 (m, 2H). Anal. Calcd for C$_{27}$H$_{26}$N$_2$O$_5$S$_2$: C, 62.05, H, 5.01; N, 5.36. Found: C, 61.81, H, 4.95; N, 5.34.

Enzyme Assays. Inhibition of recombinant human caspase-3 and other caspases by the isatin analogues was assessed using a fluorometric assay by measuring the accumulation of a fluorogenic product, 7-amino-4-methylcoumarin (7-AMC): All of the tested compounds inhibited caspase-3 and caspase-7 in a concentration-dependent manner with similar potency.

Example 11

(S)-1-(4-Hydroxybenzyl)-5-(2-phenoxymethyl-pyrrolidine-1-sulfonyl)-1H-indole-2,3-dione (11f). To a solution of 11e (53 mg, 0.1 mmol) in methanol (3 mL) and water (1 mL) was added NaOH (4.4 mg, 0.11 mmol) at ambient temperature. The mixture was stirred overnight, then acidified with 1 M HCl to pH of 4 and extracted with ethyl acetate (50 mL). The ethyl acetate was washed with NaCl (30 mL) and dried over Na$_2$SO$_4$. After evaporation of the solvent, the crude product was purified with ether to afford 36 mg (73%) of 11f as a yellow solid, mp 170.5-172.4° C. $^1$H NMR (300 MHz, CDCl$_3$) δ 8.01 (s, 1H), 7.97 (dd, J=8.25 Hz, J=2.1 Hz, 1H), 7.24-7.19 (m, 4H), 6.96-6.80 (m, 6H), 4.85 (s, 2H), 4.16 (m, 1H), 3.98-3.88 (m, 2H), 3.49 (m, 1H), 3.21 (m, 1H), 2.03 (m, 2H), 1.80 (m, 2H). Anal. Calcd for C$_{26}$H$_{24}$N$_2$O$_6$S.0.25H$_2$O: C, 62.83, H, 4.97; N, 5.64. Found: C, 62.87, H, 4.74; N, 5.69.

Example 12

(S)-1-(6-Fluoropyridin-3-yl-methyl)-5-(2-phenoxymethylpyrrolidine-1-sulfonyl)-1H-indole-2,3-dione (11g) was prepared according to the same procedure for compound 11a, except using 5-(bromomethyl)-2-fluoropyridine,21 and purified with ether to afford 94 mg (76%) of 11g as yellow solid, mp 113.3-11.4.7° C. $^1$H NMR (300 MHz, CDCl$_3$) δ 8.28 (s, 1H), 8.03 (m, 2H), 7.82 (m 1H), 7.27-7.20 (m, 2H), 7.00-6.79 (m, 5H), 4.92 (s, 2H), 4.13 (m, 1H), 3.95 (m, 2H), 3.50 (m, 1H), 3.26 (m, 1H), 2.05 (m, 2H), 1.80 (m, 2H). Anal. Calcd for C$_{25}$H$_{22}$FN$_3$O$_5$S: C, 60.60, H, 4.47, N, 8.48. Found: C, 60.60, H, 4.59, N, 8.33.

Example 13

(S)-1-(2-Fluoro-pyridin-4-yl-methyl)-5-(2-phenoxymethyl-pyrrolidine-1-sulfonyl)-1H-indole-2,3-dione (11h) was prepared according to the same procedure for compound 11a, except using 4-(bromomethyl)-2-fluoropyridine,21 and purified with ether to afford 41 mg (33%) of 11h as a yellow solid, mp 180.1-181.9° C. $^1$H NMR (300 MHz, CDCl$_3$) δ 8.25 (d, J=5.4 Hz, 1H), 8.07 (s, 1H), 8.00 (d, J=8.4 Hz, 1H), 7.23 (m, 2H), 7.12 (d, J=4.2 Hz, 1H), 6.96-6.73 (m, 5H), 4.94 (s, 2H), 4.13 (m, 1H), 4.00-3.89 (m, 2H), 3.49 (m, 1H), 3.28 (m, 1H), 2.04 (m, 2H), 1.82 (m, 2H). Anal. Calcd for C$_{25}$H$_{22}$FN$_3$O$_5$S: C, 60.60, H, 4.47; N, 8.48. Found: C, 60.32, H, 4.34; N, 8.35.

Example 14

(S)-1-(6-Fluoro-pyridin-2-yl-methyl)-5-(2-phenoxymethyl-pyrrolidine-1-sulfonyl)-1H-indole-2,3-dione (11i) was prepared according to the same procedure for compound 11a, except using 6-(bromomethyl)-2-fluoropyridine,21 and purified with ether to afford 57 mg (46%) of 11i as a yellow solid, mp 128.6-129.4° C. $^1$H NMR (300 MHz, CDCl$_3$) δ 8.02 (m, 2H), 7.82 (m, 1H), 7.28-7.10 (m, 4H), 6.92 (m, 2H), 6.85 (m, 2H), 4.96 (s, 2H), 4.14 (m, 1H), 3.94 (m, 2H), 3.51 (m, 1H), 3.23 (m, 1H), 2.03 (m, 2H), 1.79 (m, 2H). Anal. Calcd for C$_{25}$H$_{22}$FN$_3$O$_5$S.0.25H$_2$O: C, 60.05, H, 4.54; N, 8.40. Found: C, 60.06, H, 4.49; N, 8.24.

Example 15

(S)-1-(tert-Butoxycarbonyl)azetidine-2-carboxylic Acid (13). To a solution of (S)-2-azetidinecarboxylic acid 12 (1.0 g, 10.0 mmol) and di-tert-butyl dicarbonate (2.83 g, 12.5 mmol) in ethanol (20 mL) and water (10 mL) was added NaOH (420 mg, 10.5 mmol) at 0° C. The mixture was stirred overnight at ambient temperature. After evaporation of the ethanol, water (20 mL) was added, then acidified with diluted HCl to a pH of 3 and extracted with ethyl acetate (50 mL×3). The combined ethyl acetate was washed with water (30 mL) and saturated NaCl (30 mL), and dried over Na$_2$SO$_4$. After evaporation of the ethyl acetate to afford 1.98 g (100%) of 13 as a white solid. $^1$H NMR (300 MHz, CDCl$_3$) δ 4.79 (m, 1H), 3.93 (m, 2H), 2.46 (m, 2H), 1.48 (s, 9H).

Example 16

(S)-tert-Butyl 2-(Hydroxymethyl)azetidine-1-carboxylate (14).17 To a solution of 13 (0.94 g, 4.7 mmol) in THF (10 mL) was added slowly a 1 M BH3 in THF (21.0 mL) at 0° C. The mixture was stirred 2 days at ambient temperature, then cold water (20 mL) was added at 0° C. After evaporation of the THF in vacuo, an 10% aqueous solution of citric acid (15 mL) was added and extracted with ethyl acetate (50 mL×2). The combined ethyl acetate was washed with saturated NaHCO$_3$ (30 mL) and NaCl (30 mL), and dried over Na$_2$SO$_4$. Evaporation of the ethyl acetate in vacuo afforded 0.86 g (100%) of 14 as a colorless oil. $^1$H NMR (300 MHz, CDCl$_3$) δ 4.40 (m, 1), 3.85-3.70 (m, 3H), 2.13 (m, 1H), 1.90 (m, 1H), 1.42 (s, 9H).

Example 17

((S)-1-(tert-Butoxycarbonyl)azetidine-2-yl)methyl 4-methylbenzenesulfonate (15) was prepared according to the same procedure for compound 8, except using compound 14, and purified with hexanes-ether (1:1) to afford 1.34 g (86%) of 15 as a colorless oil. $^1$H NMR (300 MHz, CDCl$_3$) δ 7.79 (d, J=8.7 Hz, 2H), 7.34 (d, J=8.1 Hz, 2H), 4.33-4.24 (m, 2H), 4.10 (m, 1H), 3.78 (m 2H), 2.44 (s, 3H), 2.21 (m, 2H), 1.36 (s, 9H).

Example 18

(S)-tert-Butyl 2-(phenoxymethyl)azetidine-1-carboxylate (16) was prepared according to the same procedure for compound 9, except using compound 15, and purified with hexanes-ether (2:1) to afford 0.81 g (79%) of 16 as a colorless oil. $^1$H NMR (300 MHz, CDCl$_3$) δ CDCl$_3$ 7.30 (m, 2H), 6.94 (m, 3H), 4.53 (m, 1H), 4.26 (m, 1H), 4.12 (m, 1H), 3.93 (m, 2H), 2.33 (m, 2H), 1.43 (s, 9H).

Example 19

(S)-5-(2-Phenoxymethyl-azetidine-1-sulfonyl)-1H-indole-2,3-dione (17) was prepared according to the same procedure for compound 10, except using compound 16, and purified with ether to afford 715 mg (63%) of 17 as a yellow solid, mp 173.2-174.5° C. $^1$H NMR (300 MHz, DMSO) δ 11.48 (s, 1H), 7.98 (dd, J=8.25 Hz, J=2.1 Hz, 1H), 7.77 (s, 1H), 7.27 (m, 2H), 7.10 (d, J=8.1 Hz, 1H), 6.91 (d, J=7.8 Hz, 3H), 4.20-4.02 (m, 3H), 3.70 (m, 1H), 3.55 (m, 1H), 2.22 (m, 1H), 2.02 (m, 1H). LRMS (FAB) m/e: 373.0 (M+H, 100). Anal. Calcd for $C_{18}H_{16}N_2O_5S \cdot 0.5H_2O$: C, 56.68, H, 4.49; N, 7.34. Found: C, 56.96, H, 4.39; N, 7.30.

Example 20

(S)-1-Methyl-5-(2-phenoxymethyl-azetidine-1-sulfonyl)-1H-indole-2,3-dione (18a) was prepared according to the same procedure for compound 11a, except using compound 17, and purified with ether to afford 46 mg (48%) of 18a as an orange solid, mp 173.5-174.9° C. $^1$H NMR (300 MHz, CDCl$_3$) δ 8.04 (m, 2H), 7.24 (m, 2H), 6.94 (m, 2H), 6.79 (m, 2H), 4.46 (m, 1H), 4.10 (m, 2H), 3.86 (m, 2H), 3.25 (m, 3H), 2.30 (m, 2H). Anal. Calcd for $C_{19}.N_2O_5S$: C, 59.06, H, 4.70, N, 7.25. Found: C, 58.98, H, 4.75; N, 7.19.

Example 21

(S)-1-Benzyl-5-(2-phenoxymethyl-azetidine-1-sulfonyl)-1H-indole-2,3-dione (18b) was prepared according to the same procedure for compound 11a, except using compound 17 and benzyl bromide, and purified with hexanes-ether (1:2) to afford 92 mg (80%) of 18b as an orange solid, mp 157.1-158.9° C. $^1$H NMR (300 MHz, CDCl$_3$) δ 8.05 (d, J=2.1 Hz, 1H), 7.95 (dd, J=8.25 Hz, J=2.1 Hz, 1H), 7.34 (m, 5H), 7.22 (m, 2H), 6.94 (m, 1H), 6.87-6.78 (m, 3H), 4.93 (s, 2H), 4.46 (m, 1H), 4.10 (m, 2H), 2.82 (m, 2H), 2.32 (m 2H). Anal. Calcd for $C_{25}H_{22}N_2O_5S$: C, 64.92, H, 4.79; N, 6.06. Found: C, 64.82, H, 4.79; N, 7.97.

Example 22

(S)-1-(4-Methoxybenzyl)-5-(2-phenoxymethyl-azetidine-1-sulfonyl)-1H-indole-2,3-dione (18c) was prepared according to the same procedure for compound 11a, except using compound 17 and 4-methoxybenzyl chloride, and purified with hexanes-ether (1:2) to afford 62 mg (50%) of 18c as an orange solid, mp 159.8-161.5° C. $^1$H NMR (300 MHz, CDCl$_3$) δ 8.04 (s, 1H), 7.96 (dd, J=8.25 Hz, J=2.1 Hz, 1H), 7.25 (m, 4H), 6.97-6.87 (m, 4H), 6.80 (d, J=7.8 Hz, 2H), 4.87 (s, 2H), 4.45 (m, 2H), 4.11 (m, 2H), 3.84 (m, 2H), 3.81 (s, 3H), 2.32 (m, 2H). Anal. Calcd for $C26H_{24}N_2O_6S$: C, 63.40, H, 4.91; N, 5.69. Found: C, 63.65, H, 4.93; N, 5.59.

Example 23

(S)-1-(4-Methylthiobenzyl)-5-(2-phenoxymethyl-azetidine-1-sulfonyl)-1H-indole-2,3-dione (18d) was prepared according to the same procedure for compound 11a, except using compound 17 and 4-methylthiobenzyl bromide, and purified with hexanes-ether (1:2) to afford 57 mg (45%) of 18d as an orange solid, mp 167.6-169.2° C. $^1$H NMR (300 MHz, CDCl$_3$) δ 8.05 (d, J=1.5 Hz, 1H), 7.96 (dd, J=8.4 Hz, J=1.8 Hz, 1H), 7.25 (m, 6H), 6.95 (t, J=7.2 Hz, 1H), 6.86-6.78 (m, 3H), 4.89 (s, 2H), 4.46 (m, 1H), 4.11 (m, 2H), 3.82 (m, 2H), 2.49 (s, 3H), 2.39-2.25 (m, 2H). Anal. Calcd for $C_{26}H_{24}N_2O_5S_2$: C, 61.40, H, 4.76; N, 5.51. Found: C, 60.99, H, 4.71; N, 5.36.

Example 24

(S)-1-(4-Fluorobenzyl)-5-(2-phenoxymethyl-azetidine-1-sulfonyl)-1H-indole-2,3-dione (18e) was prepared according to the same procedure for compound 11a, except using compound 17 and 4-fluorobenzyl bromide, and purified with hexanes-ether (1:2) to afford 85 mg (71%) of 18e as an orange solid, mp 164.6-165.7° C. $^1$H NMR (300 MHz, CDCl$_3$) δ 8.05 (d, J=1.8 Hz, 1H), 7.97 (dd, J=8.4 Hz, J=2.1 Hz, 1H), 7.34-7.20 (m, 4H), 7.07 (t, J=8.7 Hz, 2H), 6.94 (t, J=7.2 Hz, 1H), 6.86-6.77 (m, 3H), 4.90 (s, 2H), 4.47 (m, 1H), 4.10 (m, 2H), 3.85 (m, 2H), 2.36-2.22 (m, 2H). Anal. Calcd for $C_{25}H_{21}FN_2O_5S$: C, 62.49, H, 4.41; N, 5.83. Found: C, 62.27, H, 4.48; N, 5.69.

Example 25

(S)-1-(2-Fluorobenzyl)-5-(2-phenoxymethyl-azetidine-1-sulfonyl)-1H-indole-2,3-dione (18f) was prepared according to the same procedure for compound 11a, except using compound 17 and 2-fluorobenzyl bromide, and purified with solid, mp 147.1-148.0° C. $^1$H NMR (300 MHz, CDCl$_3$) δ 8.05 (d, J=1.8 Hz, 1H), 8.00 (dd, J=8.25 Hz, J=2.1 Hz, 1H), 7.35 (m, 2H), 7.24-7.11 (m, 3H), 7.02-6.78 (m, 5H), 4.98 (s, 2H), 4.47 (m, 1H), 4.11 (m, 2H), 3.85 (m, 2H), 2.35-2.25 (m, 2H). Anal. Calcd for $C_{25}H_{21}FN_2O_5S$: C, 62.49, H, 4.41; N, 5.83. Found: C, 62.25, H, 4.47; N, 5.68.

Example 26

(S)-1-(6-Fluoropyridin-3-ylmethyl)-5-(2-phenoxymethylazetidine-1-sulfonyl)-1H-indole-2,3-dione (18g) was prepared according to the same procedure for compound 11a, except using compound 17 and 5-(bromomethyl)-2-fluoropyridine, and purified with ether to afford 74 mg (62%) of 18g as an orange solid, mp 176.8-178.3° C. $^1$H NMR (300 MHz, CDCl$_3$) δ 8.27 (d, J=2.4 Hz, 1H), 8.07 (d, J=2.1 Hz, 1H), 8.01 (dd, J=8.25 Hz, J=2.1 Hz, 1H), 7.79 (td, J=8.1 Hz, J=2.4 Hz, 1H), 7.22 (m, 2H), 7.00-6.77 (m, 5H), 4.92 (s, 2H), 4.49 (m, 1H), 4.09 (m, 2H), 3.85 (m, 2H), 2.35-2.23 (m, 2H). Anal. Calcd for $C_{24}H_{20}FN_3O_5S$: C, 59.87, H, 4.19; N, 8.73. Found: C, 59.81, H, 4.16; N, 8.62.

Example 27

(S)-1-(2-Fluoropyridin-4-yl-methyl)-5-(2-phenoxymethylazetidine-1-sulfonyl)-1H-indole-2,3-dione (18h) was prepared according to the same procedure for compound 11a, except using compound 17 and 4-(bromomethyl)-2-fluoropyridine, and purified with ether to afford 36 mg (30%) of 18h as an orange solid, mp 159.0-159.9° C. $^1$H NMR (300 MHz, CDCl$_3$) δ 8.23 (d, J=5.1 Hz, 1H), 8.08 (s, 1. H), 7.98 (dd, J=8.7 Hz, J=2.1 Hz, 1H), 7.22 (m, 2H), 7.10 (d, J=5.4 Hz, 1H), 6.93 (t, J=7.5 Hz, 1H), 6.84-6.72 (m, 4H), 4.93 (s, 2H), 4.49 (m, 1H), 4.07 (m, 2H), 3.91-3.81 (m, 2H), 2.35-2.22 (m, 2H). Anal. Calcd for $C_{24}.FN_3O_5S \cdot 0.5H_2O$: C, 58.77, H, 4.32; N, 8.57. Found: C, 58.69, H, 4.45; N, 8.26.

Example 28

(S)-1-(6-Fluoropyridin-2-yl-methyl)-5-(2-phenoxymethylazetidine-1-sulfonyl)-1H-indole-2,3-dione (18i) was prepared according to the same procedure for compound 11a, except using compound 17 and 6-(bromomethyl)-2-fluoropyridine, and purified with ether to afford 62 mg (52%) of 18i as an orange solid, mp 144.7-146.1° C. $^1$H NMR (300 MHz, CDCl$_3$) δ 8.03 (s, 1H), 8.00 (dd, J=8.25 Hz, J=2.1 Hz, 1H), 7.82 (m, 1H), 7.27-7.11 (m, 4H), 6.92 (m, 2H), 6.79 (m, 2H). Anal. Calcd for $C_{24}H_{20}FN_3O_5S$: C, 59.87, H, 4.19; N, 8.73. Found: C, 59.59, H, 4.27; N, 8.48.

Example 29

2-(Pyridin-3-yl-oxymethyl)-pyrrolidine-1-carboxylic acid tert-butyl ester (19) was prepared according to the same procedure for compound 9, except using 3-hydroxypyridine. The crude product was purified with ether to afford 1.70 g (61%) of 19 as a colorless oil. $^1$H NMR (300 MHz, CDCl$_3$) δ 8.32 (s, 1H), 8.21 (s, 1H), 7.21 (m, 2H), 4.16 (m, 2H), 3.99-3.86 (m, 1H), 3.38 (m, 2H), 2.05-1.84 (m, 4H), 1.47 (s, 9H).

Example 30

5-(2-(Pyridin-3-yl-oxymethyl)-pyrrolidine-1-sulfonyl)-1H-indole-2,3-dione (20) was prepared according to the same procedure for compound 10, except using compound 19, and the crude product was recrystallized from ethyl acetate to afford 1.75 g (82%) of 20 as a yellow solid, mp 215.9-217.8° C. $^1$H NMR (300 MHz, DMSO) δ 11.42 (s, 1H), 8.26 (d, J=3.0 Hz, 1H), 8.16 (d, J=4.5 Hz, 1H), 8.02 (d, J=8.4 Hz, 1H), 7.78 (s, 1H), 7.38 (m, 1H), 7.33 (m, 1H), 7.05 (d, J=8.4 Hz, 1H), 4.15-4.02 (m, 2H), 3.90 (m, 1H), 3.34 (m, 1H), 3.12 (m, 1H), 1.87 (m, 2H), 1.67-1.54 (m, 2H). LCMS m/e: 387.8 (M+H). Anal. Calcd for $C_{18}H_{17}N_3O_5S.0.5H_2O$: C, 54.54, H, 4.58; N, 10.60. Found: C, 54.56, H, 4.70; N, 10.04.

Example 31

1-Methyl-5-(2-(pyridin-3-yl-oxymethyl)-pyrrolidine-1-sulfonyl)-1H-indole-2,3-dione (21a) was prepared according to the same procedure for compound 11a, except using compound 20, and the crude product was purified with ethyl acetate to afford 55 mg (55%) of 21a as a yellow solid, mp 142.1-143.4° C. $^1$H NMR (300 MHz, CDCl$_3$) δ 8.24 (d, J=2.7, 1H), 8.22 (dd, J=3.9 Hz, J=2.1 Hz, 1H), 8.08 (dd, J=8.4, J=2.1 Hz, 1H), 7.26 (s, 1H), 7.21 (m, 2H), 7.00 (d, J=8.4 Hz, 1H), 4.22 (m, 1H), 3.98 (m, 2H), 3.53 (m, 1H), 3.30 (s, 3H), 3.22 (m, 2H), 2.03 (m, 2H), 1.80 (m, 2H). LCMS m/e: 401.84 (M+H). Anal. Calcd for $C_{19}H_{19}N_3O_5S$: C, 56.85, H, 4.77; N, 10.47. Found: C, 56.48, H, 4.87; N, 10.19.

Example 32

1-Benzyl-5-(2-(pyridin-3-yl-oxymethyl)-pyrrolidine-1-sulfonyl)-1H-indole-2,3-dione (21b) was prepared according to the same procedure for compound 11a, except using compound 20 and benzyl bromide, and the crude product was purified with ether to afford 61 mg (51%) of 21b as a yellow solid, mp 79.6-80.7° C. $^1$H NMR (300 MHz, CDCl$_3$) δ 8.25 (s, 1H), 8.22 (t, J=2.7 Hz, 1H), 8.04 (d, J=2.1 Hz, 1H), 7.98 (dd, J=8.4 Hz, J=2.1 Hz, 1H), 7.36 (m, 5H), 7.22 (m, 2H), 6.91 (d, J=8.8 Hz, 1H), 4.97 (s, 2H), 4.25 (m, 1H), 3.99-3.94 (m, 2H), 3.55-3.48 (m, 1H), 3.21-3.15 (m, 1H), 2.10-1.97 (m, 2H), 1.84-1.75 (m, 2H). LRMS (FAB) m/e: 484.1 (M+Li, 100); HRMS (FAB) m/e calcd for $C_{25}H_{23}N_3O_5SLi$ (M+Li) 484.1518, found 484.1539.

Example 33

1-(4-Methoxybenzyl)-5-(2-(pyridin-3-yl-oxymethyl)-pyrrolidine-1-sulfonyl)-1H-indole-2,3-dione (21c) was prepared according to the same procedure for compound 11a, except using 20 and 4-methoxybenzyl chloride. The crude product was purified with ether to afford 45 mg (36%) of 21c as a yellow solid, mp 156.7-158.4° C. $^1$H NMR (300 MHz, CDCl$_3$) δ 8.26 (s, 1H), 8.23 (t, J=2.7 Hz, 1H), 8.03 (d, J=1.5 Hz, 1H), 7.98 (dd, J=8.25 Hz, J=2.1 Hz, 1H), 7.28 (d, J=8.7 Hz, 2H), 7.22 (t, J=2.1 Hz, 2H), 6.94 (d, J=8.1 Hz, 1H), 6.90 (d, J=8.7 Hz, 2H), 4.90 (s, 2H), 4.24 (m, 1H), 4.01-3.90 (m, 2H), 3.81 (s, 3H), 3.55-3.49 (m, 1H), 3.20-3.15 (m, 1H), 2.05 (m, 2H), 1.78 (m, 2H). LCMS m/e:507.9 (M+H). Anal. Calcd for $C_{26}H_{25}N_3O_6S$: C, 61.53, H, 4.96; N, 8.28. Found: C, 61.27, H, 4.95; N, 8.17.

Example 34

1-(4-Methylthiobenzyl)-5-(2-(pyridin-3-yl-oxymethyl)-pyrrolidine-1-sulfonyl)-1H-indole-2,3-dione (21d) was prepared according to the same procedure for compound 11a, except using 20 and 4-methylsulfanylbenzyl bromide. The crude product was purified with ether to afford 57 mg (44%) of 21d as a yellow solid, mp 81.5-83.1° C. $^1$H NMR (300 MHz, CDCl$_3$) δ 8.25-8.21 (m, 2H), 8.03 (d, J=1.8 Hz, 1H), 7.24 (s, 3H), 7.21 (m, 1H), 6.89 (d, J=8.4 Hz, 1H), 4.91 (s, 2H), 4.23 (m, 1H), 4.00-3.89 (m, 2H), 3.51 (m, 1H), 3.14 (m, 1H), 2.47 (s, 3H), 2.02 (m, 2H), 1.78 (m, 2H). LRMS (FAB) m/e: 530.1 (M+Li, 100); HRMS (FAB) m/e calcd for $C_{26}H_{25}N_3O_5S_2Li$ (M+Li) 530.1396, found 530.1397.

Example 35

1-(4-Fluorobenzyl)-5-(2-(pyridin-3-yl-oxymethyl)-pyrrolidine-1-sulfonyl)-1H-indole-2,3-dione (21e) was prepared according to the same procedure for compound 11a, except using 20 and 4-fluorobenzyl bromide. The crude product was purified with ether to afford 35 mg (28%) of 21e as a yellow solid, mp 77.1-78.3° C. $^1$H NMR (300 MHz, CDCl$_3$) δ 8.25 (m, 2H), 8.05 (s, 1H), 8.03-7.99 (m, 1H), 7.36-7.32 (m, 2H), 7.23 (m, 2H), 7.09 (t, J=8.7 Hz, 2H), 6.90 (d, J=8.7 Hz, 1H), 4.94 (s, 2H), 4.25 (d, J=6.0 Hz, 1H), 3.98 (m, 2H), 3.52 (m, 1H), 3.19 (m, 1H), 2.05 (m, 2H), 1.80 (m, 2H). LRMS (FAB) m/e: 502.1 (M+Li, 100); HRMS (FAB) m/e calcd for $C_{25}H_{22}FN_3O_5SLi$ (M+Li) 502.1424, found 502.1420.

Example 36

2-(Pyridin-4-yl-oxymethyl)-pyrrolidine-1-carboxylic acid tert-butyl ester (22) was prepared according to the same procedure for compound 9, except using 4-hydroxypyridine. The crude product was purified with ethyl acetate to afford 1.31 g (47%) of 22 as a colorless oil. $^1$H NMR (300 MHz, CDCl$_3$) δ 8.42 (m, 2H), 6.87 (m, 2H), 4.15 (m, 3H), 3.43 (m, 2H), 1.98 (m, 4H), 1.50 (s, 9H).

Example 37

5-(2-(Pyridin-4-yl-oxymethyl)-pyrrolidine-1-sulfonyl)-1H-indole-2,3-dione (23) was prepared according to the same procedure for compound 10, except using compound 22, purified with ethyl acetate to afford 1.17 g (55%) of 23 as a yellow solid, mp 204.2-205.3° C. $^1$H NMR (300 MHz, CDCl$_3$) δ 11.44 (s, 1H), 8.37 (d, J=5.7 Hz, 2H), 8.03 (dd, J=8.4 Hz, J=2.1 Hz, 1H), 7.79 (s, 1H), 7.06 (d, J=8.4 Hz, 1H), 6.96 (d, J=6.0 Hz, 2H), 4.17-4.05 (m, 2H), 3.90 (m, 1H), 3.32 (m, 1H), 3.10 (m, 1H), 1.85 (m, 2H), 1.60 (m, 2H). LCMS m/e: 387.9 (M+H). Anal. Calcd for $C_{18}H17N_3O_5S.0.75H_2O$: C, 53.92, H, 4.65; N, 10.48. Found: C, 54.14, H, 4.39; N, 10.35.

Example 38

1-[4-(2-Fluoroethoxy)-benzyl]-5-(2-phenoxymethyl-pyrrolidine-1-sulfonyl)-1H-indole-2,3-dione (WC-II-89). A solution of 8 (97 mg, 0.25 mmol) in DMF (3 mL) was added 60% NaH (10 mg, 0.25 mmol) at 0° C. The mixture was stirred 5 min, then 4 (250 mg) was added. The mixture was stirred 10 min. at 0° C., ethyl acetate (50 mL) was added, washed with water (30 mL), NaCl (30 mL) and dried over Na$_2$SO$_4$. After evaporation of the ethyl acetate, the crude product was purified with ether to afford 74 mg (55%) of WC(II)-89 as a yellow solid, mp 164.0-164.8° C. $^1$H NMR (300 MHz, CDCl$_3$) δ 8.01 (s, 1H), 7.95 (d, J=8.1 Hz, 1H), 7.28-7.21 (m, 4H), 6.95-6.80 (m, 6H), 4.86 (s, 2H), 4.75 (dt, J=47.4 Hz, J=4.2 Hz, 2H), 4.20 (dt, J=28.5 Hz, J=4.2 Hz, 2H), 4.15 (m, 1H), 3.92 (m, 2H), 3.49 (m, 1H), 3.22 (m, 1H), 2.02 (m, 2H), 1.78 (m, 2H). Anal. Calcd for $C_{28}H_{27}FN_2O_6S$: C, 62.44, H, 5.05; N, 5.20. Found: C, 62.50, H, 5.11, N, 5.12.

Example 39

1-[4-(2-Bromoethoxy)-benzyl]-5-(2-phenoxymethyl-pyrrolidine-1-sulfonyl)-1H-indole-2,3-dione (9) was prepared according to the same procedure for compound WC-II-89 (Example 38) except using compound 6, purified with hexane-ether (1:2) to afford 587 mg (68%) of 9 as a yellow solid, mp 164.1-164.9° C. $^1$H NMR (300 MHz, CDCl$_3$) δ 8.05 (s, 1H), 8.01 (dd, J=8.1 Hz, J=2.1 Hz, 1H), 7.32-7.25 (m, 4H), 6.70-6.84 (m, 6H), 4.91 (s, 2H), 4.32 (t, J=6.0 Hz, 2H), 4.20 (m, 1H), 3.97 (m, 2H), 3.67 (t, J=6.3 Hz, 2H), 3.55 (m, 1H), 3.26 (m, 1H), 2.07 (m, 2H), 1.83 (m, 2H). Anal. Calcd for C$_{28}$H$_{27}$BrN$_2$O$_6$S.0.25H$_2$O: C, 55.68, H, 4.59; N, 4.64. Found: C, 55.66, 4.28, N, 4.54.

Example 40

Methanesulfonic acid 2-{4-[2,3-dioxo-5-(2-phenoxymethyl-pyrrolidine-1-sulfonyl)-2,3-dihydro-indol-1-ylmethyl]-phenoxy}-ethyl ester (10). A solution of 9 (300 mg, 0.5 mmol) and AgOMs (1.01 g, 5.0 mmol) in CH$_3$CN (10 mL) was heated to reflux overnight. After evaporation of the solvent, the crude product was purified with ether to afford 228 mg (74%) of 10 as a yellow solid, mp 151.8-152.6° C. $^1$H NMR (300 MHz, CDCl$_3$) δ 8.05 (s, 1H), 8.01 (dd, J=8.1 Hz, J=1.8 Hz, 1H), 7.33-7.25 (m, 4H), 7.00-6.84 (m, 6H), 4.90 (s, 2H), 4.60 (t, J=4.8 Hz, 2H), 4.27 (t, J=4.8 Hz, 2H), 4.20 (m, 1H), 3.97 (m, 2H), 3.54 (m, 1H), 3.26 (m, 1H), 3.11 (s, 3H), 2.06 (m, 2H), 1.83 (m, 2H). Anal. Calcd for C$_{29}$H$_{30}$N$_2$O$_9$S$_2$: C, 56.66, H, 4.92; N, 4.56. Found: C, 56.74, H, 4.88, N. 4.67. HPLC conditions for purification of [$^{18}$F]WC-II-89: Alltech Ecosoil C18 250×10 mm, 10μ; 25% acetonitrile, 45% methanol, 30% 0.1 M ammonium formate buffer (pH=4.5); 5 mL/min, 251 nm; t$_R$=15 min.

Example 41

1-(4-Bromo-benzyl)-5-(2-Phenoxymethyl-pyrrolidine-1-sulfonyl)-1H-indole-2,3-dione (25d, see FIG. 19) 60% NaH (10 mg, 0.25 mmol) was added to a solution of compound 24 (16, 41) (97 mg, 0.25 mmol) in DMF (3 mL) at 0° C. The mixture was stirred 15 min. at 0° C., then 4-bromobenzyl bromide (125 mg, 0.5 mmol) was added. The mixture was stirred 1 h at room temperature, ethyl acetate (50 mL) was added, washed with water (30 mL), saturated NaCl (30 mL) and dried over Na$_2$SO$_4$. After evaporation of the solvent, the crude product was purified with hexane-CH$_2$Cl$_2$-ether (1:1:1) to afford 108 mg (78%) of 25d as a yellow solid, mp 112.1-113.4° C. $^1$H NMR (300 MHz, CDCl$_3$) δ 8.02 (s, 1H), 7.96 (d, J=8.1 Hz, 1H), 7.50 (d, J=8.4 Hz, 2H), 7.20 (m, 5H), 6.92 (t, J=7.8 Hz, 1H), 6.80 (d, J=8.1 Hz, 2H), 4.87 (s, 2H), 4.15 (m, 1H), 3.93 (m, 2H), 3.49 (m, 1H), 3.23 (m, 1H), 2.02 (m, 2H), 1.79 (m, 2H).

Example 42

1-(4-Hydroxy-benzyl)-5-[2-(pyridin-3-yl-oxymethyl)-pyrrolidine-1-sulfonyl]-1H-indole-2,3-dione (28b) 1-[4-(tert-Butyl-diphenyl-silanyloxy)-benzyl]-5-[2-(pyridin-3-yloxymethyl)-pyrrolidine-1-sulfonyl]-1H-indole-2,3-dione (150 mg, 0.2 mmol) and nBu$_4$NF (53 mg, 0.2 mmol) in THF (6 mL) and water (2 mL) was stirred for 2 h, ethyl acetate (50 mL) was added, washed with water (30 mL), saturated NaCl (30 mL) and dried over Na$_2$SO$_4$. The crude product was purified with ether-ethyl acetate (1:1) to afford 65 mg (66%) of 28b as a yellow solid, mp 126.7-128.8° C. $^1$H NMR (300 MHz, CDCl$_3$) δ 8.21 (m, 2H), 8.01 (s, 10H), 7.95 (d, J=8.1 Hz, 1H), 7.26 (m, 2H), 7.19 (d, J=8.4 Hz, 2H), 6.90 (d, J=8.7 Hz, 1H), 6.84 (d, J=8.4 Hz, 2H), 4.87 (s, 2H), 4.19 (m, 1H), 3.95 (m, 2H), 3.48 (m, 2H), 3.19 (m, 1H), 2.00 (m, 2H), 1.79 (m, 2H).

Example 43

1-(4-Bromo-benzyl)-5-[2-(pyridin-3-yl-oxymethyl)-pyrrolidine-1-sulfonyl]-1H-indole-2,3-dione (28c) was prepared according to the same procedure for compound 25d except using 29 and 4-bromobenzyl bromide, purified with CH$_2$Cl$_2$-ethyl acetate (1:1) to afford 53 mg (38%) of 28c as a yellow solid, mp 92.1-93.3° C. $^1$H NMR (300 MHz, CDCl$_3$) δ 8.24 (m, 2H), 8.04 (s, 1H), 7.98 (d, J=8.1 Hz, 1H), 7.51 (d, J=8.1 Hz, 2H), 7.23 (m, 4H), 6.86 (d, J=8.4 Hz, 1H), 4.90 (s, 2H), 4.23 (m, 1H), 3.97 (m, 2H), 3.50 (m, 1H), 3.17 (m, 1H), 2.02 (m, 2H), 1.78 (m, 2H).

Example 44

2-[2-Oxo-5-(2-phenoxymethyl-pyrrolidine-1-sulfonyl)-1,2-dihydro-indol-3-yl-idene]-malononitrile (26) A solution of 24 (97 mg, 0.25 mmol) and malononitrile (18 mg, 0.27 mmol) in methanol (4 mL) was heated to reflux for 1 h, then cooled to room temperature. The solid was filtered out and dried in vacuum to afford 93 mg (86%) of 26 as a red solid, mp 245.7-248.4° C. $^1$H NMR (300 MHz, DMSO) δ 11.66 (s, 1H), 8.23 (s, 1H), 8.02 (d, J=8.7 Hz, 1H), 7.25 (t, J=8.7 Hz, 2H), 7.09 (d, J=8.7 Hz, 1H), 6.90 (m, 3H), 4.05 (m, 1H), 3.92 (m, 2H), 3.39 (m, 1H), 3.15 (m, 1H), 1.90 (m, 2H), 1.72 (m, 2H).

Example 45

2-[1-Methyl-2-oxo-5-(2-phenoxymethyl-pyrrolidine-1-sulfonyl)-1,2-dihydro-indol-3-yl-idene]-malononitrile (27a) was prepared according to the same procedure for compound 26 except using 25a (16, 41) to afford 39 mg (87%) of 27a as a red solid, mp 217.5° C. (decomp). 1H NMR (300 MHz, CDCl$_3$) δ 8.47 (s, 1H), 8.06 (dd, J=8.6 Hz, J=1.8 Hz, 1H), 7.21 (t, J=7.8 Hz, 2H), 6.93 (t, J=7.5 Hz, 1H), 6.89 (d, J=8.7 Hz, 1H), 6.73 (d, J=7.8 Hz, 2H), 4.11 (m, 1H), 4.08 (m, 1H), 4.00 (m, 1H), 3.49 (m, 2H), 3.26 (s, 3H), 2.11-1.88 (m, 4H).

Example 46

2-[1-Benzyl-2-oxo-5-(2-phenoxymethyl-pyrrolidine-1-sulfonyl)-1,2-dihydroindol-3-yl-idene]-malononitrile (27b) was prepared according to the same procedure for compound 26 except using 25b, (41) to afford 92 mg (88%) of 27b as a purple solid, mp 196.6° C. (decomp). $^1$H NMR (300 MHz, CDCl$_3$) δ 8.43 (s, 1H), 7.93 (dd, J=8.6 Hz, J=1.8 Hz, 1H), 7.39-7.29 (m, 5H), 7.14 (t, J=7.2 Hz, 2H), 6.89 (t, J=7.2 Hz, 1H), 6.83 (d, J=8.7 Hz, 1H), 6.68 (d, J=7.8 Hz, 2H), 4.90 (s, 2H), 4.05 (m, 2H), 3.97 (m, 1H), 3.45 (m, 2H), 2.07-1.85 (m 4H).

Example 47

2-[1-(Hydroxy-benzyl-2-oxo-5-(2-phenoxymethyl-pyrrolidine-1-sulfonyl)-1,2-dihydro-indol-3-yl-idene]-malononitrile (27c) was prepared according to the same procedure for compound 26 except using 25c (41), to afford 68 mg (84%) of 27c as a purple solid, mp 174.9° C. (decomp). $^1$H NMR (300 MHz, DMSO) δ 9.51 (s, 1H), 8.30 (s, 1H), 8.10 (dd, J=8.6 Hz, J=1.8 Hz, 1H), 7.32-7.20 (m, 5H), 6.95-6.84 (m, 3H), 6.76 (d, J=8.7 Hz, 2H), 4.87 (s, 2H), 4.09 (m, 1H), 3.97 (m, 2H), 3.40 (m, 1H), 3.20 (m, 1H), 1.90 (m, 2H), 1.71 (m, 2H).

Example 48

2-[1-(4-Bromo-benzyl)-2-oxo-5-(2-phenoxymethyl-pyrrolidine-1-sulfonyl)-1,2-dihydro-indol-3-yl-idene]-malononitrile (27d) was prepared according to the same procedure for compound 26 except using 25d, to afford 52 mg (86%) of 27d as a purple solid, mp 237.0° C. (decomp). $^1$H NMR (300 MHz, CDCl$_3$) δ 8.46 (s, 1H), 7.95 (d, J=8.1 Hz, 1H), 7.51 (d, J=8.4 Hz, 2H), 7.20-7.13 (m, 4H), 6.90 (t, J=7.5 Hz, 1H), 6.79 (d, J=8.4 Hz, 1H), 6.68 (d, J=7.8 Hz, 2H), 4.84 (m, 2H), 4.06 (m, 2H), 3.97 (m, 1H), 3.46 (m, 2H), 2.08-1.86 (m, 4H).

Example 49

2-{1-Benzyl-2-oxo-5-[2-(pyridine-3-yloxymethyl)-pyrrolidine-1-sulfonyl]-1,2-dihydro-indol-3-yl-idene}-malononitrile (30a) was prepared according to the same procedure for compound 26 except using 28a (41), to afford 59 mg (75%) of 30a as a purple solid, mp 216.5° C. (decomp). $^1$H NMR (300 MHz, CDCl$_3$) δ 8.53 (s, 1H), 8.23 (m, 2H), 7.98 (dd, J=8.4 Hz, J=1.8 Hz, 1H), 7.42-7.35 (m, 5H), 7.20 (m, 2H), 6.91 (d, J=8.7 Hz, 1H), 4.98 (s, 2H), 4.23 (m, 1H), 4.05 (m, 2H), 3.55 (m, 1H), 3.33 (m, 1H), 2.08 (m, 2H), 1.90 (m, 2H).

Example 50

2-{1-(4-Hydroxy-benzyl)-2-oxo-5-[2-(pyridine-3-yloxymethyl)-pyrrolidine-1-sulfonyl]-1,2-dihydro-indol-3-yl-idene}-malononitrile (30b) was prepared according to the same procedure for compound 26 except using 28b, to afford 46 mg (85%) of 30b as a purple solid, mp 203.3° C. (decomp). $^1$H NMR (300 MHz, DMSO) δ 9.50 (s, 1H), 8.31 (s, 1H), 8.25 (d, J=2.7 Hz, 1H), 8.17 (dd, J=4.5 Hz, J=1.5 Hz, 1H), 8.10 (d, J=8.1 Hz, 1H), 7.34 (m, 3H), 7.24 (d, J=8.4 Hz, 2H), 6.76 (d, J=8.7 Hz, 2H), 4.88 (s, 2H), 4.16 (m, 1H), 4.08 (m, 1H), 3.96 (m, 1H), 3.41 (m, 1H), 3.18 (m, 1H), 1.91 (m, 2H), 1.71 (m, 2H).

Example 51

2-{1-(4-Bromo-benzyl)-2-oxo-5-[2-(pyndine-3-yloxymethyl)-pyrrolidine-1-sulfonyl]-1,2-dihydro-indol-3-yl-idene}-malononitrile (30c) was prepared according to the same procedure for compound 26 except using 28c, to afford 16 mg (45%) of 30c as a purple solid, mp 232.3° C. (decomp). $^1$H NMR (300 MHz, CDCl$_3$) δ 8.50 (s, 1H), 8.21 (m, 1H), 8.16 (s, 1H), 7.96 (d, J=8.4 Hz, 1H), 7.51 (d, J=8.1 Hz, 2H), 7.20 (m, 4H), 6.84 (d, J=8.7 Hz, 1H), 4.89 (m, 2H), 4.20 (m, 1H), 4.02 (m, 2H), 2.05-1.78 (m, 4H).

Example 52

2-{1-(4-Methoxy-benzyl)-2-oxo-5-[2-(pyridin-3-yloxymethyl)-pyrrolidine-1-sulfonyl]-1,2-dihydro-indol-3-yl-idene}-malononitrile (30d) was prepared according to the same procedure for compound 26 except using 28d (41), to afford 91 mg (82%) of 30d as a purple solid, mp 132.4° C. (decomp). $^1$H NMR (300 MHz, CDCl$_3$) δ 8.47 (s, 1H), 8.20 (m, 2H), 7.95 (dd, J=8.4 Hz, J=1.8 Hz, 1H), 7.26 (d, J=8.7 Hz, 2H), 7.19 (m, 2H), 6.92 (d, J=8.4 Hz, 1H), 6.89 (d, J=8.7 Hz, 2H), 4.88 (s, 2H), 4.21 (m, 1H), 4.02 (m, 2H), 3.80 (s, 3H), 3.50 (m, 1H), 3.29 (m, 1H), 2.05 (m, 2H), 1.86 (m, 2H).

Example 53

1-[4-(tert-Butyl-diphenyl-silanyloxy)-benzyl]-5-[2-(pyridin-3-yl-oxymethyl)-pyrrolidine-1-sulfonyl]-1H-indole-2,3-dione was prepared according to the same procedure for compound 25d except using 29 (41) and 4-(tert-Butyl-diphenyl-silanyloxy)-benzyl bromide, purified with ether-ethyl acetate (1:1) to afford 332 mg (59%) as a yellow solid, $^1$H NMR (300 MHz, CDCl$_3$) δ 8.25 (s, 1H), 8.22 (m, 1H), 8.00 (s, 1H), 7.93 (d, J=8.1 Hz, 1H), 7.67 (m, 4H), 7.45-7.32 (m, 6H), 7.22 (m, 2H), 7.05 (d, J=8.7 Hz, 2H), 6.83 (d, J=8.1 Hz, 1H), 6.74 (d, J=9.0 Hz, 2H), 4.80 (s, 2H), 4.24 (m, 1H), 3.95 (m, 2H), 3.51 (m, 1H), 3.14 (m, 1H), 2.02 (m, 2H), 1.78 (m, 2H), 1.08 (s, 9H). Anal. Calcd for C$_{41}$H$_{41}$N$_3$O$_6$SSi: C, 67.28, H, 5.65; N, 5.74. Found: C, 66.84, H, 5.69; N, 5.62.

Example 54

This example provides, in Table 8, Elemental analysis of the Michael Acceptor Isatin analogues disclosed herein.

TABLE 8

Elemental analysis of Isatin Michael Acceptor analogues.

| Compound | Formula | Calcd | | | Found | | |
|---|---|---|---|---|---|---|---|
| | | C | H | N | C | H | N |
| 9d | C$_{26}$H$_{23}$BrN$_2$O$_5$S | 56.22 | 4.17 | 5.04 | 55.96 | 4.25 | 4.81 |
| 10b | C$_{25}$H$_{23}$N$_3$O$_6$S•0.25H$_2$O | 60.29 | 4.76 | 8.44 | 60.19 | 5.11 | 8.01 |
| 10c | C$_{25}$H$_{22}$BrN$_3$O$_5$S | 53.96 | 3.99 | 7.55 | 53.36 | 4.11 | 7.36 |
| 8 | C$_{22}$H$_{18}$N$_4$O$_4$S | 60.82 | 4.18 | 12.9 | 60.75 | 4.14 | 12.68 |
| 11a | C$_{23}$H$_{20}$N$_4$O$_4$S | 61.59 | 4.49 | 12.49 | 61.43 | 4.46 | 12.39 |
| 11b | C$_{29}$H$_{24}$N$_4$O$_4$S | 66.4 | 4.61 | 10.68 | 66.15 | 4.56 | 10.58 |
| 11c | C$_{29}$H$_{24}$N$_4$O$_5$S•0.5H$_2$O | 63.38 | 4.58 | 10.19 | 63.53 | 4.69 | 10.09 |
| 11d | C$_{29}$H$_{23}$BrN$_4$O$_4$S | 57.72 | 3.84 | 9.28 | 57.49 | 3.81 | 9.2 |
| 12a | C$_{28}$H$_{23}$N$_5$O$_4$S•0.5H$_2$O | 62.91 | 4.53 | 13.1 | 63.1 | 4.26 | 12.96 |
| 12b | C$_{28}$H$_{23}$N$_5$O$_5$S•0.25H$_2$O | 61.58 | 4.34 | 12.82 | 61.78 | 4.15 | 12.68 |
| 12c | C$_{28}$H$_{22}$BrN$_5$O$_4$S | 55.64 | 3.67 | 11.59 | 55.37 | 3.65 | 11.4 |
| 12d | C$_{29}$H$_{25}$N$_5$O$_5$S•0.5H$_2$O | 61.69 | 4.64 | 12.4 | 61.73 | 4.52 | 11.96 |

Example 55

This example illustrates a 2-dimensional NMR study of an Isatin Michael Acceptor of the present teachings.

In a NMR tube compound 27d (18.1 mg, 0.03 mmol) was dissolved in CDCl$_3$ (0.75 mL) prior to addition of benzylmercaptan (18.6 mg, 0.15 mmol). The mixture was maintained for 24 h at room temperature prior to be NMR analysis.

NMR spectra were recorded on a Varian Inc. (Palo Alto, Calif., USA) Ionva-500. Proton and carbon chemical shifts were measured in ppm downfield from an internal TMS standard. Proton spectra were obtained using a 5,200 Hz spectral width collected with 64 K data points with 5.0 s preacquisition delays.

A two-dimensional COSY spectrum was collected into a 512×2,048 data matrix with 4 scans per t$_1$ value. The time domain data were zero filled to yield a 2,048×2,048 data matrix and Fourier transformed using a sine-bell weighting function in both the t$_2$ and t$_1$ dimensions.

A gradient based proton-detected heteronuclear multiple quantum coherence (gHMQC and gHMBC) spectrum was recorded. The 90° $^1$H pulse width was 8.0 μs and the 90° $^{13}$C pulse width was 14 μs. The proton spectral width was set to 4,750 Hz and the carbon spectral width was set to 21563 Hz. A 500×2,000 data matrix with 4 scans per t$_1$ value was collected. Gaussian and sine bell weighing functions were used in weighting the t$_2$ and the t$_1$ dimensions, respectively. After two-dimensional Fourier transformation, the spectra resulted in 512×2,048 data points, which were phase and baseline corrected in both dimensions.

Figure 21:
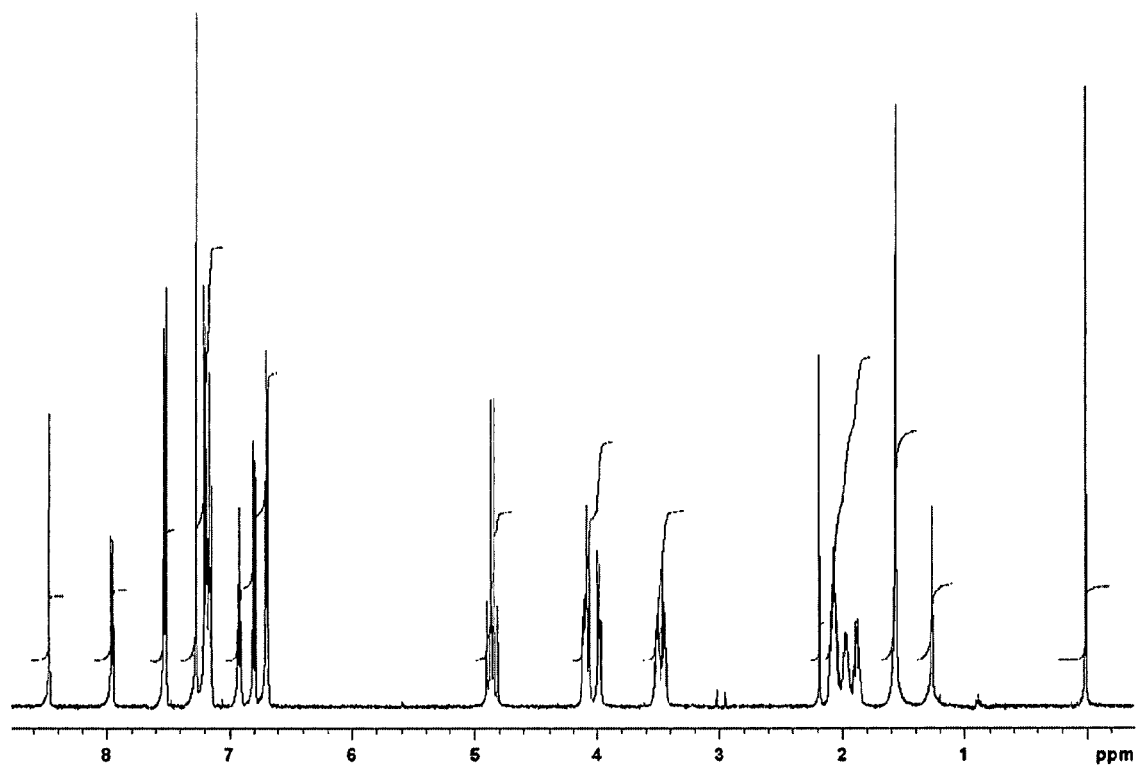
FIG. 21 illustrates an $^1$H NMR spectrum of compound 27d.
Figure 22:
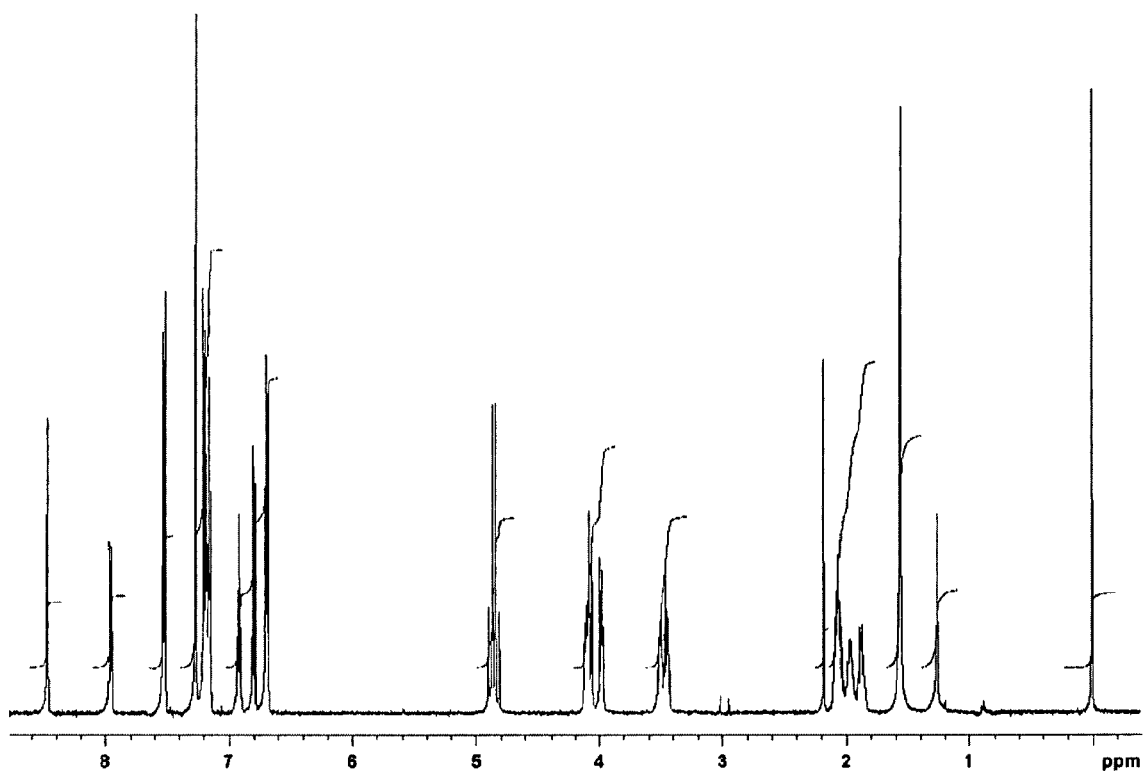
FIG. 22 illustrates an $^1$H NMR spectrum of the Michael addition product of 27d with benzylmercaptan.
Figure 23:
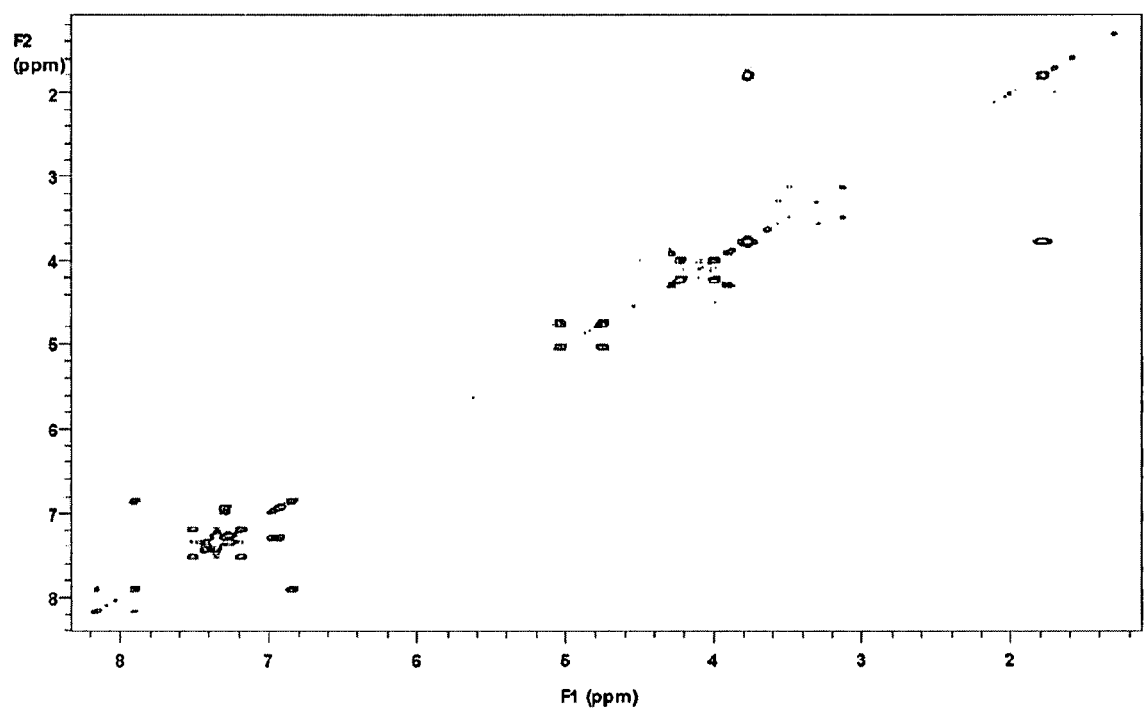
FIG. 23 illustrates a COSY spectrum of the Michael addition product of 27d with benzylmercaptan.
Figure 24:
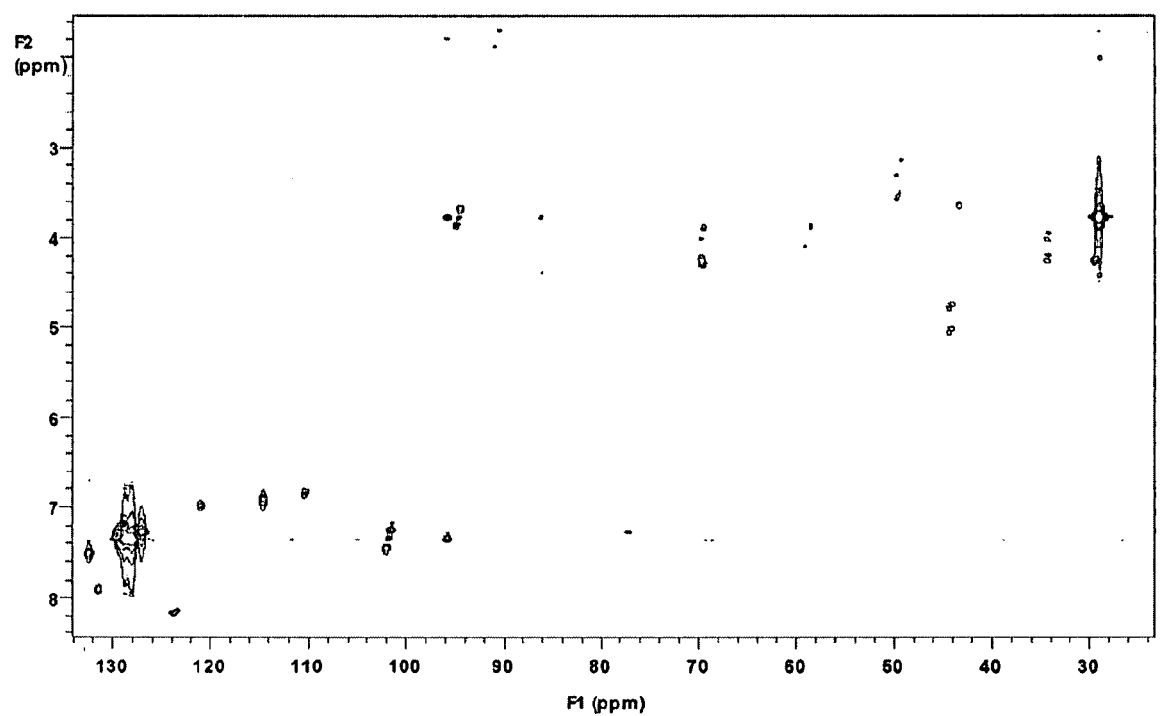
FIG. 24 illustrates an HMQC spectrum of the Michael addition product of 27d with benzylmercaptan.
Figure 25:
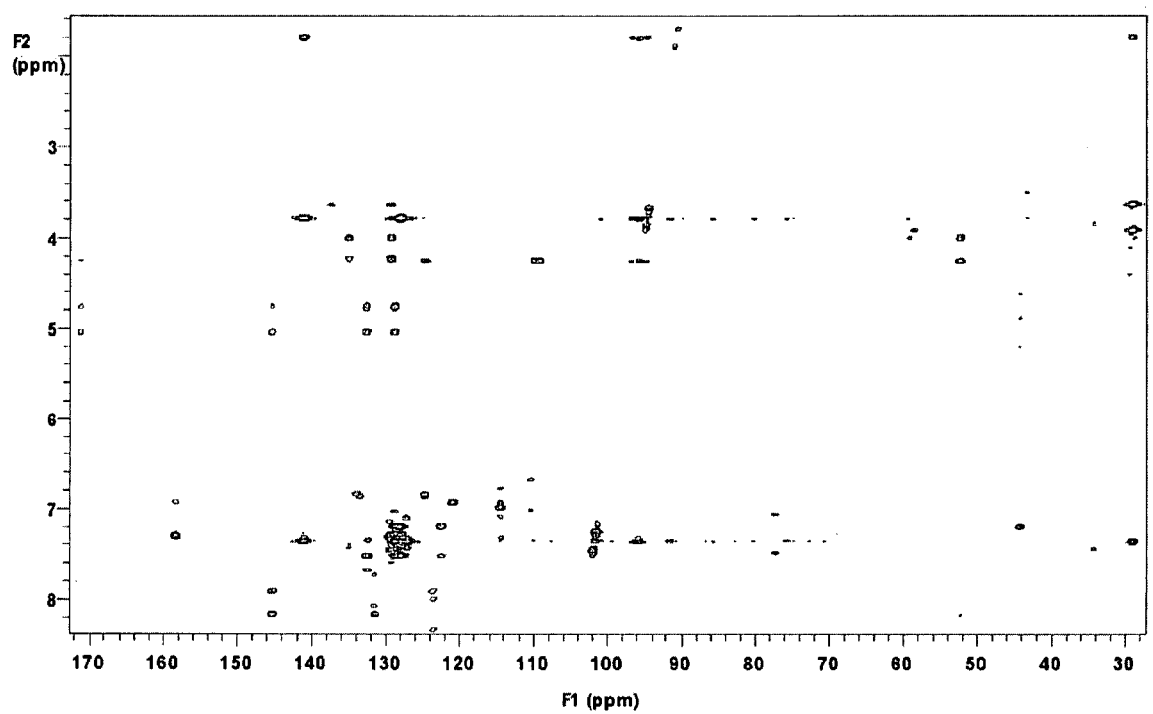
FIG. 25 illustrates an HMBC spectrum of the Michael addition product of 27d with benzylmercaptan.
Figure 26:
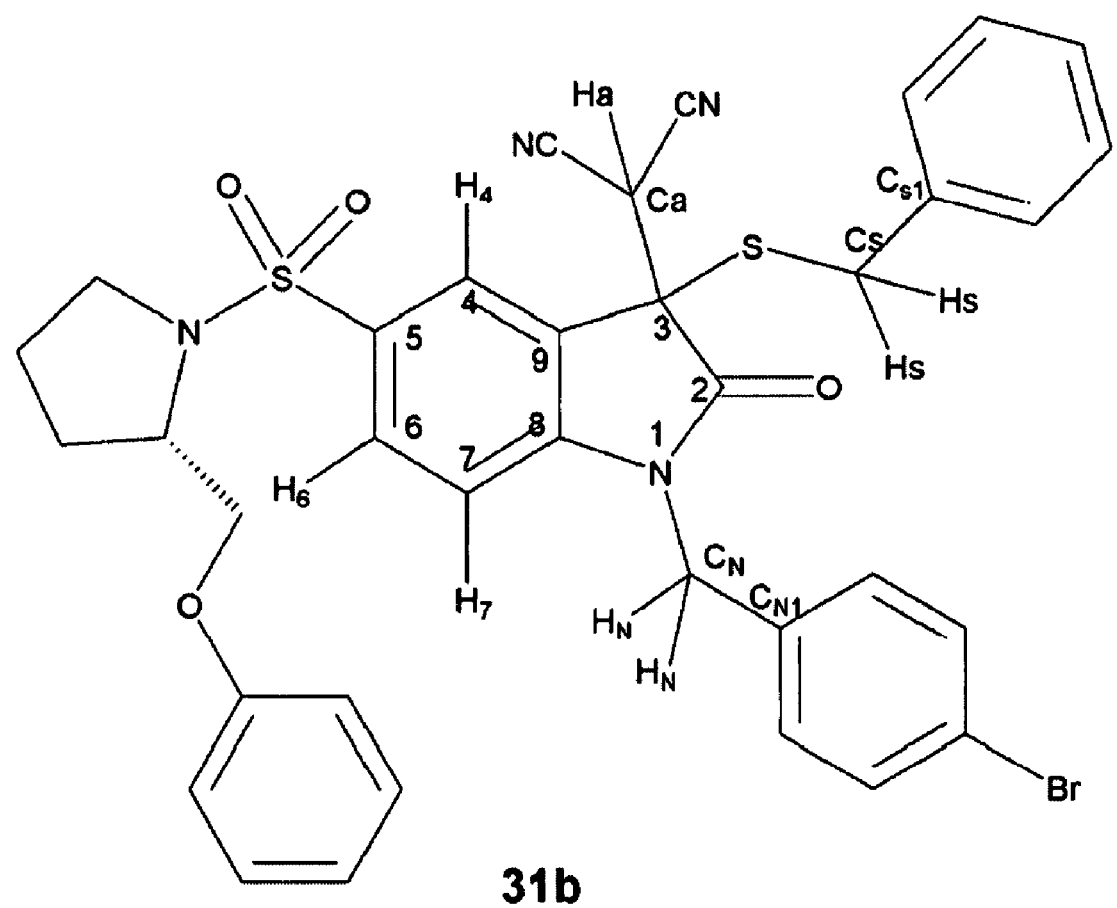
FIG. 26 illustrates a structure assignment of the Michael Addition Product 31b.

The ¹H spectra of starting material 27d and the Michael addition product were shown in FIGS. 21 and 22. The COSY, HMQC, and HMBC spectra of the Michael addition product were shown in FIGS. 23-25. The $^1$H and $^{13}$C assigned for the Michael addition product 31b were shown in FIG. 26.

All publications and patent applications cited in this specification are herein incorporated by reference as if each individual publication or patent application were specifically and individually indicated to be incorporated by reference. Although the foregoing teachings have been described in some detail by way of illustration and example for purposes of clarity of understanding, it will be readily apparent to those of ordinary skill in the art in light of the teachings that certain changes and modifications may be made thereto without departing from the spirit or scope of the appended claims.

REFERENCES

1. Jacobson, M. D.; Weil, M.; Raff, M. C. Programmed Cell Death in Animal Development. *Cell* 1997, 88, 347-354.
2. Reed, J. C. Apoptosis-based Therapies. *Nature Rev. Drug Discovery* 2002, 1, 111-121.
3. Rodriguez, I.; Matsuura, K.; Ody, C.; Nagata, S.; Vassalli, P. Systemic injection of a tripeptide inhibits the intracellular activation of CPP32-like proteases in vivo and fully protects mice against Fas-mediated fulminant liver destruction and death. *J. Exp. Med.* 1996, 184, 2067-2072.
4. O'Brien, T.; Lee, D. Prospects for caspase inhibitors. *Mini Rev. Med. Chem.* 2004, 4, 153-165.
5. Denault, J.-B.; Salvesen, G. S. Capsases: keys in the ignition of cell death. *Chem. Rev.* 2002, 102, 4489-4499.
6. Garcia-Calvo, M.; Peterson, E. P.; Leiting, B.; Ruel, R.; Nicholson, D. W.; Thornberry, N. A. Inhibition of human caspases by peptide-based and macromolecular inhibitors. *J. Biol. Chem.* 1998, 273, 32608-32613.
7. Hotchkiss, R. S.; Chang, K. C.; Swanson, P. E.; Tinsley, K. W.; Hui, J. J.; Klender, P.; Xanthoudakis, S.; Roy, S.; Black, C.; Grimm, E.; Aspiotis, R.; Han, Y.; Nicholson, D. W.; Karl, I. E. Caspase inhibitors improve survival in sepsis: a critical role of the lymphocyte. *Nature Immunol.* 2000, 1, 496-501.
8. Choong, I. C.; Lew, W.; Lee, D.; Pham, P.; Burdett, M. T.; Lam, J. W.; Wiesmann, C.; Luong, T. N.; Fahr, B.; DeLano, W. L.; McDowell, R. S.; Allen, D. A.; Erlanson, D. A.; Gordon, E. M.; O'Brien, T. Identification of potent and selective small-molecule inhibitors of caspase-3 through the use of extended tethering and structure-based drug design. *J. Med. Chem.* 2002, 45, 5005-5022.
9. Linton, S. D.; Karanewsky, D. S.; Ternansky, R. J.; Wu, J. C.; Pham, B.; Kodandapani, L.; Smidt, R.; Diaz, J.-L.; Fritz, L. C.; Tomaselli, K. J. Acyl peptides as reversible caspase inhibitors. Part 1: Initial lead optimization. *Bioorg. Med. Chem. Lett.* 2002, 12, 2969-2971.
10. Linton, S. D.; Karanewsky, D. S.; Temansky, R. J.; Chen, N.; Guo, X.; Jahangiri, K. G.; Kalish, V. J.; Meduna, S. P.; Robinson, E. D.; Ullman, B. R.; Wu, J. C.; Pham, B.; Kodandapani, L.; Smidt, R.; Diaz, J.-L.; Fritz, L. C.; von Krosigk, U.; Roggo, S.; Schmitz, A.; Tomaselli, K. J. Acyl peptides as reversible caspase inhibitors. Part 2: Further optimization. *Bioorg. Med. Chem. Lett.* 2002, 12, 2969-2971.
11. Han, Y.; Giroux, A.; Grimm, E. L.; Aspiotis, R.; Francoeur, S.; Bayl), C. I.; Mckay, D. J.; Roy, S.; Xanthoudakis, S.; Vallancourt, J. P.; Rasper, D. M.; Tam, J.; Tawa, P.; Thornberry, N. A.; Paterson, E. P.; Garcia-Calvo, M.; Becker, J. W.; Rotonda, J.; Nicholson, D. W.; Zamboni, R. J. Discovery of novel aspartyl ketone dipeptides as potent and selective caspase-3 inhibitors. *Bioorg. Med. Chem. Lett.* 2004, 14, 805-808.
12. Becker, J. W.; Rotonda, J.; Soisson, S. M.; Aspiotis, R.; Bayl), C.; Francoeur, S.; Gallant, M.; Garcia-Calvo, M.; Giroux, A.; Grimm, E.; Han, Y.; McKay, D.; Nicholson, D. W.; Peterson, E.; Renaud, J.; Roy, S.; Thornberry, N.; Zamboni, R. Reducing the peptidyl features of caspase-3 inhibitors: a structural analysis. *J. Med. Chem.* 2004, 47, 2466-2474.
13. Han, B. H., et al., *J. Biol. Chem.* 277, 30128-31036, 2002.
14. Lee, D. et al., *J. Biol. Chem.* 275, 16007-16104, 2000.
15. Chapman, J. G.; Magee, W. P.; Stukenbrok, H. A.; Beckius, G. E.; Milici, A. J.; Tracey, W. R. A novel nonpeptidic caspase 3/7 inhibitor, (S)-(+)-5-[1-(2-methoxymethylpyrrolidinyl)sulfonyl]-isatin reduces myocardial ischemic injury. *Eur. J. Pharmacol.* 2002, 456, 59-68.
16. Lee, D., et al., *J. Med. Chem.* 44, 2015-2026, 2001.
17. Abreo, M. A.; Lin, N.; Garvey, D. S.; Gunn, D. E.; Hettinger, A.; Wasicak, J. T.; Paulik, P. A.; Martin, Y. C.; Dannelly-Roberts, D. L.; Anderson, D. J.; Sullivan, J. P.; Williams, M.; Arneric, S. P.; Holladay, M. W. Novel 3-pyridyl ethers with subnanomolar affinity for central nicotinic acetylcholine receptors. *J. Med. Chem.* 1996, 39, 817-825.
18. Wildman, S. A.; Crippen, G. M. Prediction of Physicochemical Parameters by Atomic Contributions. *J. Chem. Inf. Comput. Sci.* 1999, 39, 868-873.
19. Stanton, D. T.; Jurs, P. C. Development and Use of Charged Partial Surface Area Structural Descriptors in Computer-Assisted Quantitative Structure-Property Relationship Studies. *Anal. Chem.* 1990, 62, 2323-2329.
20. Wallace, A. C.; Laskowski, R. A.; Thornton, J. M. LIGPLOT: A Program to generate schematic diagrams of protein-ligand interactions. *Protein Eng.* 1995, 8, 127-124.
21. Sullivan, P. T.; Sullivan, C. B.; Norton, S. J. R-Fluoro- and R-hydroxypyridylalanines. *J. Med. Chem.* 1971, 14, 211-214.
22. Berman, H. M.; Westbrook, J.; Feng, Z.; Gilliland, G.; Bhat, T. N. et al. The Protein Data Bank. *Nucleic Acids Res.* 2000, 28, 235-242.
23. *Molecular Operating Environment (MOE)*; 2004.03 ed.; Chemical Computing Group: Montreal, Canada.
24. Mohamadi, F.; Richards, N. G. J.; Guida, W. C.; Liskamp, R.; Lipton, M. et al. Macromodel—an Integrated Software System for Modeling Organic and Bioorganic Molecules Using Molecular Mechanics. *J. Comput. Chem.* 1990, 11, 440.
25. Jones, G.; Willett, P.; Glen, R. C.; Leach, A. R.; Taylor, R. Development and Validation of a Genetic Algorithm for Flexible Docking. *J. Mol. Biol.* 1997, 267, 727-748.
26. White, E. *Gene Dev.* 1996, 10, 1.
27. Ashkenazi, A.; Dixit, V. M. *Science* 1998, 281, 1305.
28. Evan, G.; Littlewood, T. *Science* 1998, 281, 1317.
29. Green, D. R.; Reed, J. C. *Science* 1998, 281, 1309.
30. Thornberry, N. A.; Lazebnik, Y. *Science* 1998, 281, 1312.
31. Dive, C.; Hickman, J. A. *Br. J. Cancer* 1991, 64, 192.
32. Review see Lahorte, C. M. M.; Vanderheyden, J.; Steinmetz, N.; Van De Wiele, C.; Dierckx, R. A.; Slegers, G. *Eur. J. Nucl. Med. Mol. Imaging* 2004, 31, 887.
33. Neuss, M.; Crow, M. T.; Chesley and Lakatta, E. G. *Cardiovascular Drugs and therapy*, 2001, 15, 507.
34. Yoo, J.; Dence, C. S.; Sharp, T. L.; Katzenellenbogen, J. A.; Welch, M. J. *J. Med. Chem.* 2005, 48, 6366.
35. Ledda-Columbano, G. M.; Coni, P.; Faa, G.; Manenti, G.; Columbano, A. *Am. J. Pathol.* 1992, 140, 545.
36. Higami, Y.; Tanaka, K.; Tsuchiya, T.; Shimokawa, I. *Mutation Res.* 2000, 457, 105.
37. Yagle, K. J.; Eary, J. F.; Tait, J. T.; Grierson, J. R.; Link, J. M. Lewellen, B.; Gibson, D. F.; Krohn, K. A. *J. Nucl. Med.* 2005, 46, 658.

38. Faust A.; Wagner S.; Keul P.; Schober O.; Levkau B.; Schaefers M.; Kopka K. *J. Label Compd. Radiopharm.* 2005, 48, S260 (abstract).
39. Powers, J. C., et al., *Chemical Reviews* (Washington, D.C., United States) 2002, 102(12), 4639-4750.
40. Ekici, O. D., et al., J. Med. Chem 47, 1889-1892, 2000.
41. Chu, W., et al., *Journal of Medicinal Chemistry* 48, 7637-7647, 2005.

What is claimed is:
1. An isatin analogue of structure

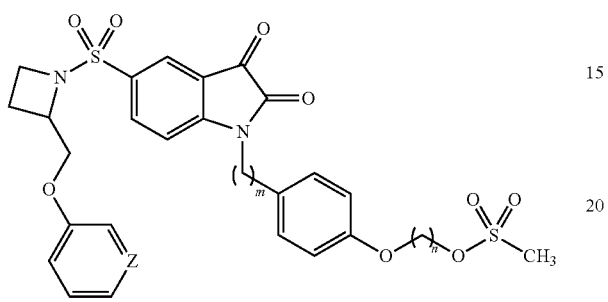

wherein Z is N or CH, m is an integer from 1 to 20 and n is an integer from 1 to 20.

2. An isatin analogue in accordance with claim 1, wherein Z is CH, m=1 and

3. An isatin analogue of structure

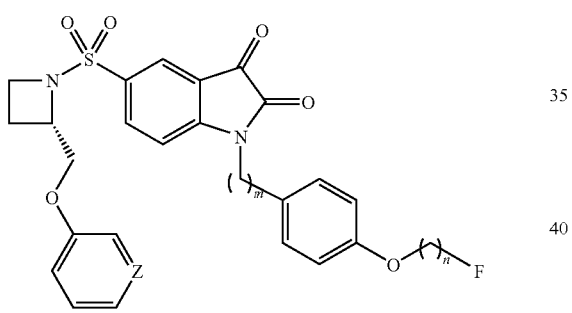

wherein Z is N or CH, m is an integer from 1 to 20 and n is an integer from 1 to 20.

4. An isatin analogue in accordance with claim 3, wherein Z is CH, m=1 and

5. An isatin analogue in accordance with claim 3, wherein the F is an F18.

6. An Isatin Michael Acceptor (IMA) selected from the group consisting of

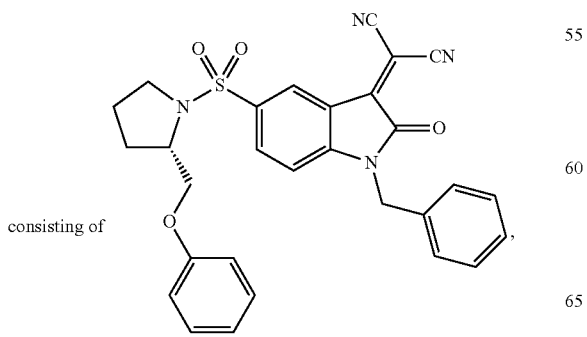

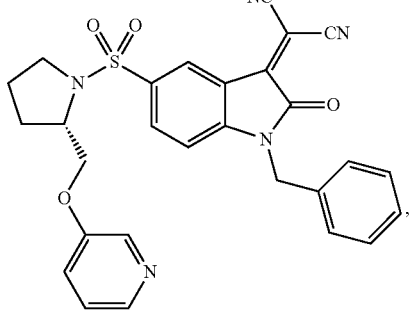

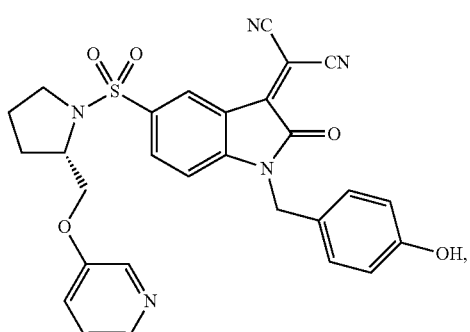

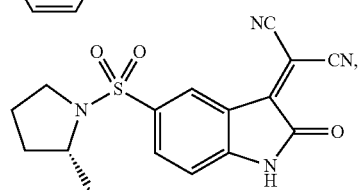

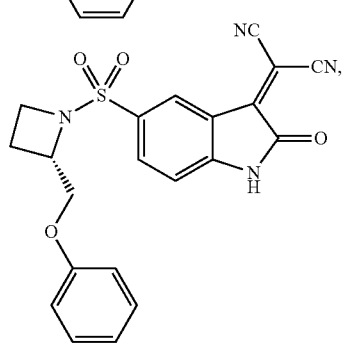

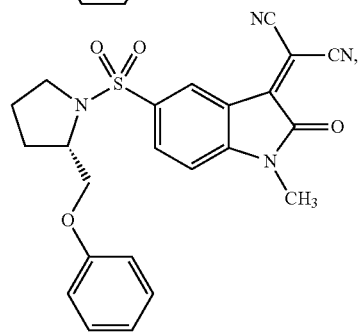

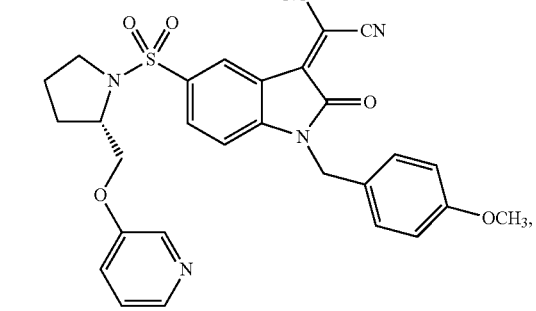
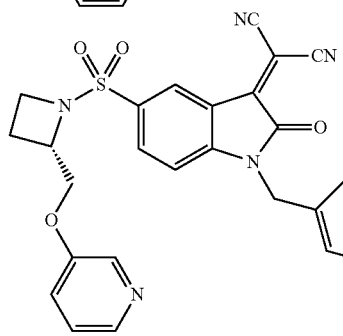
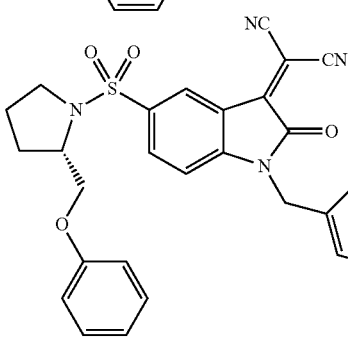
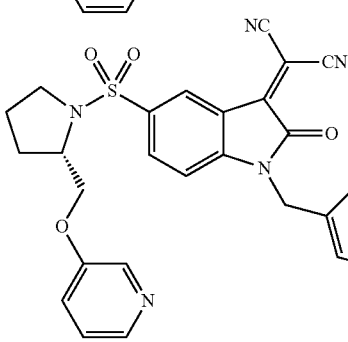
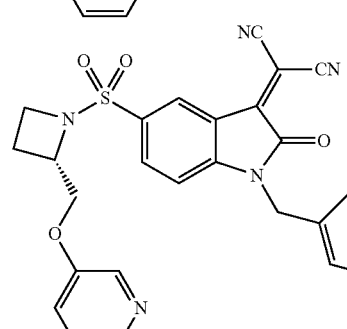
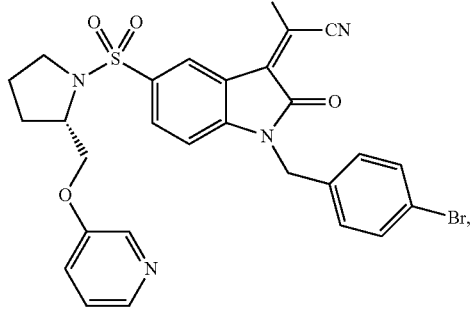
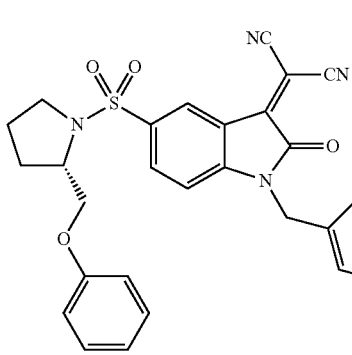
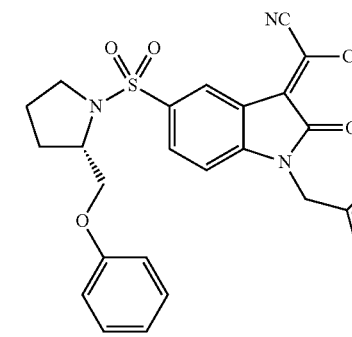
7. An IMA in accordance with claim 6, selected from the group consisting of
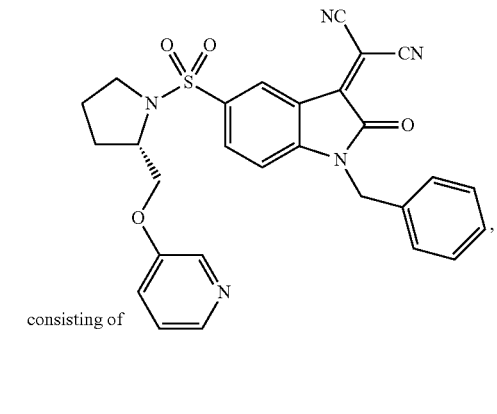
* * * * *